(12) United States Patent
Derrien et al.

(10) Patent No.: US 6,727,059 B1
(45) Date of Patent: Apr. 27, 2004

(54) METHOD FOR CONTROLLING THE FIDELITY AND PROCESSIVITY OF REVERSE TRANSCRIPTASE BY INCORPORATION AND POLYMERIZATION OF NUCLEOTIDE ANALOGS ACCEPTED AS SUBSTRATES FOR THE REVERSE TRANSCRIPTION REACTION WITHOUT BLOCKING ITS ELONGATION

(75) Inventors: Valérie Derrien, Paris (FR); Claude Reiss, Les Molieres (FR)

(73) Assignee: Centre National de la Recherche Scientifique (CNRS), Paris Cedex (FR)

( * ) Notice: Subject to any disclaimer, the term of this patent is extended or adjusted under 35 U.S.C. 154(b) by 0 days.

(21) Appl. No.: 09/926,492
(22) PCT Filed: May 10, 2000
(86) PCT No.: PCT/FR00/01260
§ 371 (c)(1),
(2), (4) Date: Jan. 28, 2002
(87) PCT Pub. No.: WO00/67698
PCT Pub. Date: Nov. 16, 2000

(51) Int. Cl.[7] .............................. C12Q 1/70; C12Q 1/68; C12N 5/06
(52) U.S. Cl. ................................. 435/5; 435/6; 435/339
(58) Field of Search .................................. 435/5, 6, 339

(56) References Cited

FOREIGN PATENT DOCUMENTS

WO 96/40166 12/1996

OTHER PUBLICATIONS

Martinez et al.; Reverse Trancriptase and Substrate Dependence of the RNA Hypermutagenesis Reaction; Nucleic Acids Research; vol. 23, No. 14, 1995, pp. 2573–2578.

McIntosh et al.; HIV and human endogenous retroviruses: a hypothesis with therapeutic implications; ACTA Biochimica Polonica, (1996), vol. 43, N. 4, pp. 583–592.

Tong et al.; Nucleotide–Induced Stable Complex Formation by HIV—1 Reverse Transcriptase; Biochemistry (1997), 36(19), pp. 5749–5757.

Ostrander et al.; Properties of herpes simplex virus type 1 and type 2 DNA polymerase; Biochim. Biophys. ACTA (1980), 609(2) pp. 232–245.

Loakes et al.: Antiviral Activity of Bicyclic Pyrimidine Nucleosides; Antiviral Chemistry & Chemotherapy, vol. 6, No. 6, 1995, pp. 371–378.

Hill et al.; Comparative mutagenicities of N6–methoxy–2, 6–diaminopurine and N6–methoxyaminopurine, 2'–deoxyribonucleosides and their 5'–triphosphates; Nucleic Acids Res., vol. 26, No. 5, 1998, PP 1144–1149.

Kowalzick et al.; Differential Incorporation of Thymidylate Analogs into DNA by DNA Polymerase Alpha and by DNA Polymerases Specified by 2 Herpes Simplex Viruses; J Gen Virol, (1982) 62 (Part 1), PP 29–38.

De Clercq; Development of resistance of human immunodeficiency virus (HIV) to anti–HIV agents: how to prevent the problem?; Int. J. Antimicrob. Agents (1997), 9(1), pp. 21–36.

(List continued on next page.)

Primary Examiner—Hankyel T. Park
(74) Attorney, Agent, or Firm—Jacobson Holman PLLC

(57) ABSTRACT

The invention concerns the use of nucleotide analogues, defined as molecules acceptable as substrate of the reverse-transcription response and enabling the addition of at least one supplementary nucleotide to the polynucleotide chain during synthesis to affect and/or take over control of the fidelity and execution of the reverse transcription. The invention also concerns a pharmaceutical composition containing said nucleotide analogues.

30 Claims, 29 Drawing Sheets

```
          pbs primer
5'GTCCCTGTTCGGGCGCCAAGGCCTGTCGGTCCGCTAGAACTAGCAATTGTGCTGATATTGAAAGAGCAG
3'CAGGGACAAGCCCGCGGTTCCGGACAGCCAGGCGATCTTGATCGTTAACACGACTATAACTTTCTCGTC TTTTTATCTCTCCTTTCTCCATCATCATTTCCCCGCTACTACTATTGGTATTACTAGCATGCCATGG
AAAAAATAGAGAGGAAAGAGGTAGTAGTAAAGGGGCGATGATGATAACCATAATGATCGTACGGTACC CCAGGCAGGCCAACGCGTGAATTAGCCCTTCCAG 3' (SEQ ID NO:1)
GGTCCGTCCGGTTGCGCACTTAATCGGGAAGGTC 5' (SEQ ID NO:2)
            ppt primer
```

OTHER PUBLICATIONS

Morris–Jones et al; Antiretroviral therapies in HIV–1 infection; Expert Opin. Invest. Drugs (1997); 6(8), pp. 1049–1061.

Patick et al., Activities of the human immunodeficiency virus type 1 (HIV–1) protease inhibitor nelfinavir mesylate in combination with reverse transcriptase and protease inhibitors against acute HIV–1 infection in vitro; Antimicrob. Agents Chemother.; (1997) 41(10); pp. 2159–2164.

Debyser et al.; Antiviral therapy for HIV infection; EOS—RIV. Immunol. Immunofarmacol. (1996) 16(2), pp. 48–52.

De Clercq et al.; Knocking Out Human Immunodeficiency Virus Through Non–Nucleoside Reverse Transcriptase Inhibitors Used as Single Agents or in Combinations: a Paradigm for the Cure of AIDS?; Farmaco, IT, Societa Chimica Italiana, Pavia, vol. 50, No. 11, 1995; pp. 735–747.

Granier et al., HIV infections: Contribution of antiretroviral combinations! Infections a VIH: L'Apport des Combinaisons Antiretrovirales; Presse Medicale, (1998), 27/13, pp. 622–623.

Ji et al.; Fidelity of HIV–1 Reverse Transcriptase Copying a Hypervariable Region of the HIV–1 env Gene; Virology 199, (1994), pp. 323–330.

pbs primer
5' GTCCCTGTTCGGGGCGCCAAGGCCTGTCGGTCCGCTAGAACTAGCAATTGTGCTGATATTGAAAGAGCAG
3' CAGGGACAAGCCCCGCGGTTCCGGACAGCCAGGCGATCTTGATCGTTAACACGACTATAACTTTCTCGTC TTTTTTATCTCTCCTTTCTCCATCATCATTCCCCGCTACTACTATTGGTATTACTAGCATGCCATGG (SEQ ID NO:1)
AAAAAATAGAGAGGAAAGAGGTAGTAGTAAAGGGGCGATGATGATAACCATAATGATCGTACGGTACC (SEQ ID NO:2)

CCAGGCAGGCCAACCCGTGAATTAGCCCCTTCCAG 3'
GGTCCGTTCCGGTTGCGCACTTAATCGGGAAGGTC 5'
                                    ppt primer

FIG. 1.1

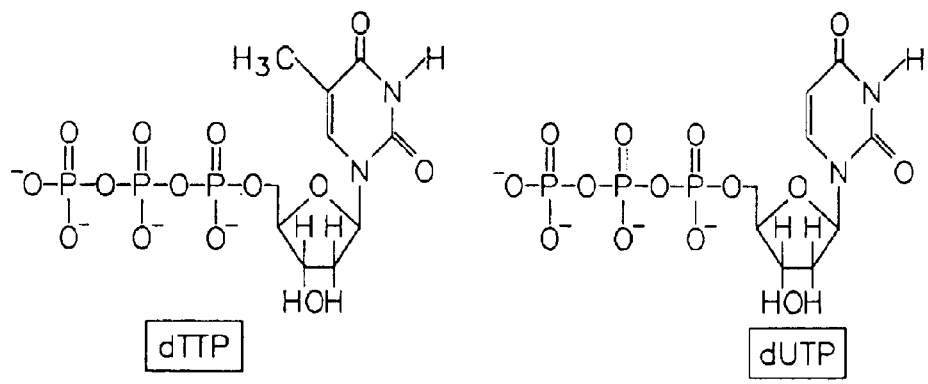
FIG. 1.2
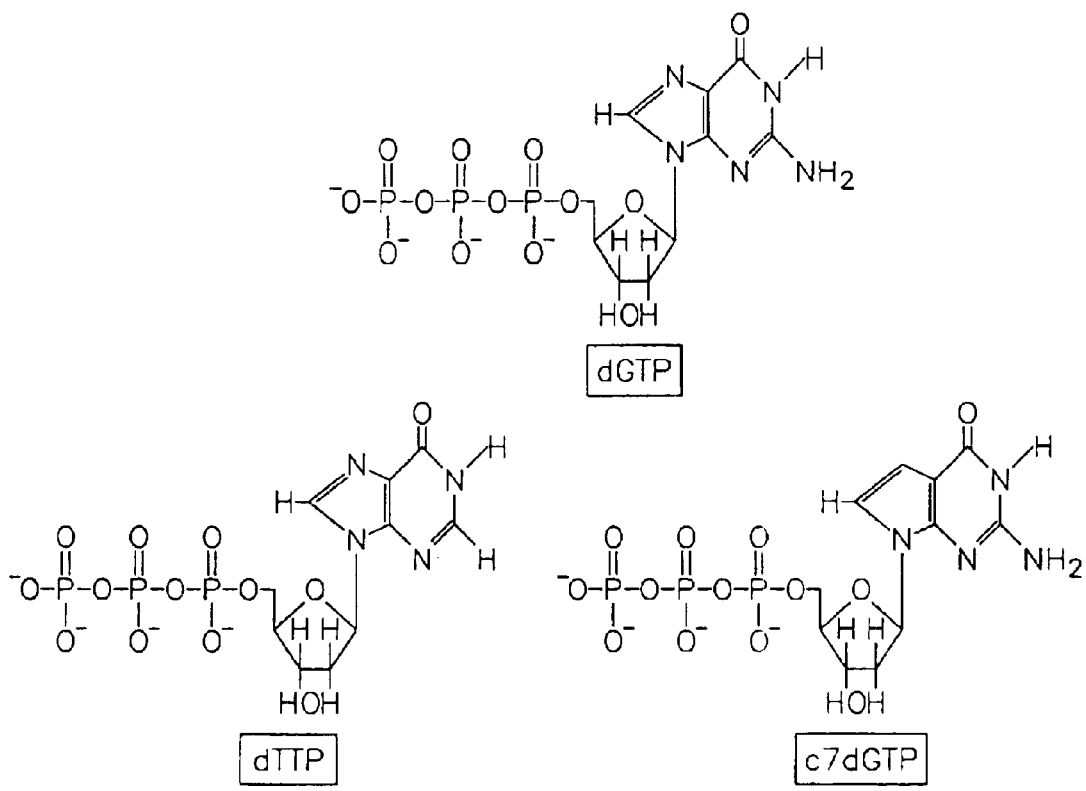
FIG. 1.3

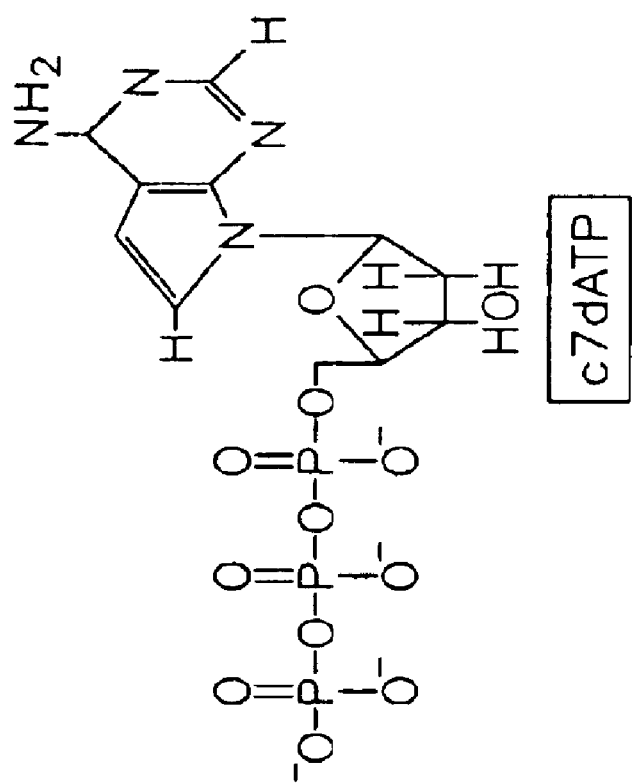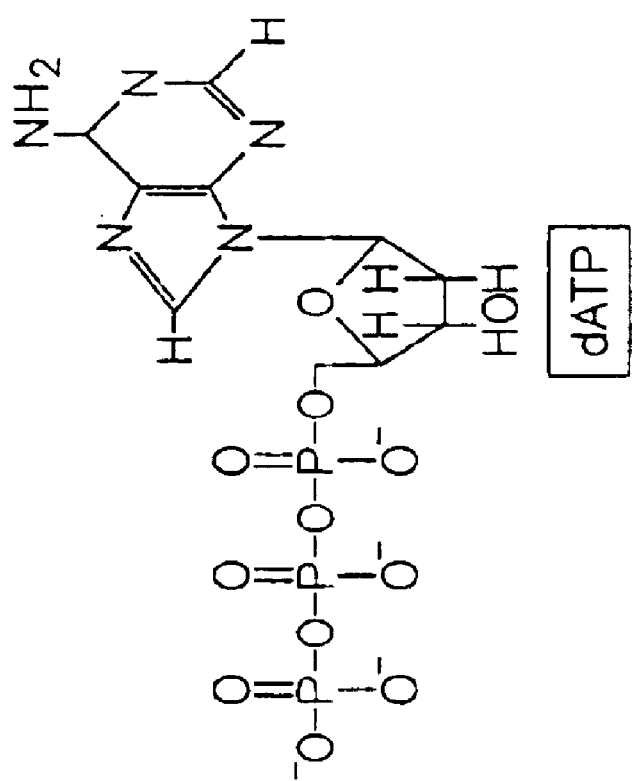
FIG. 1.4

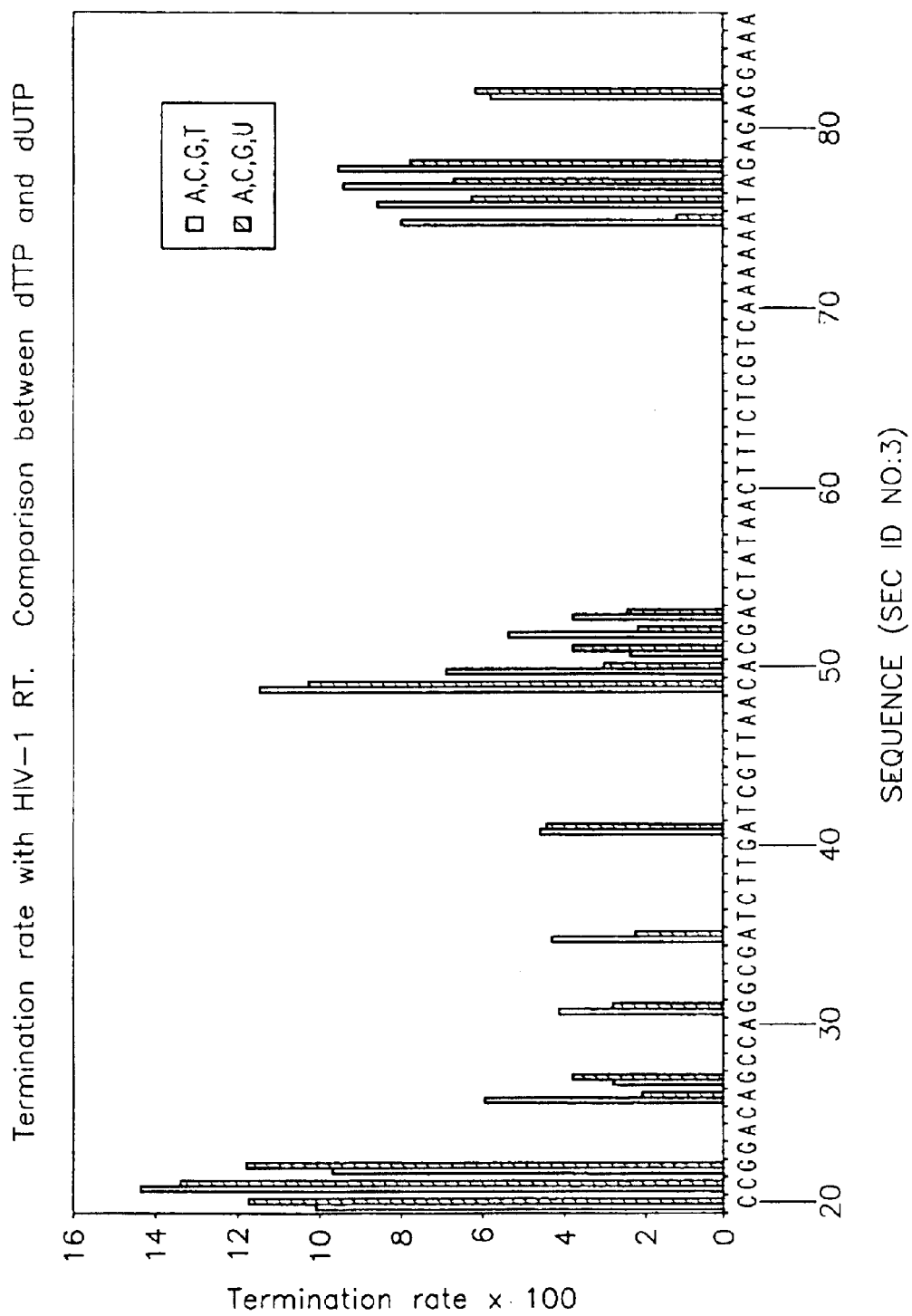
FIG. 2.1

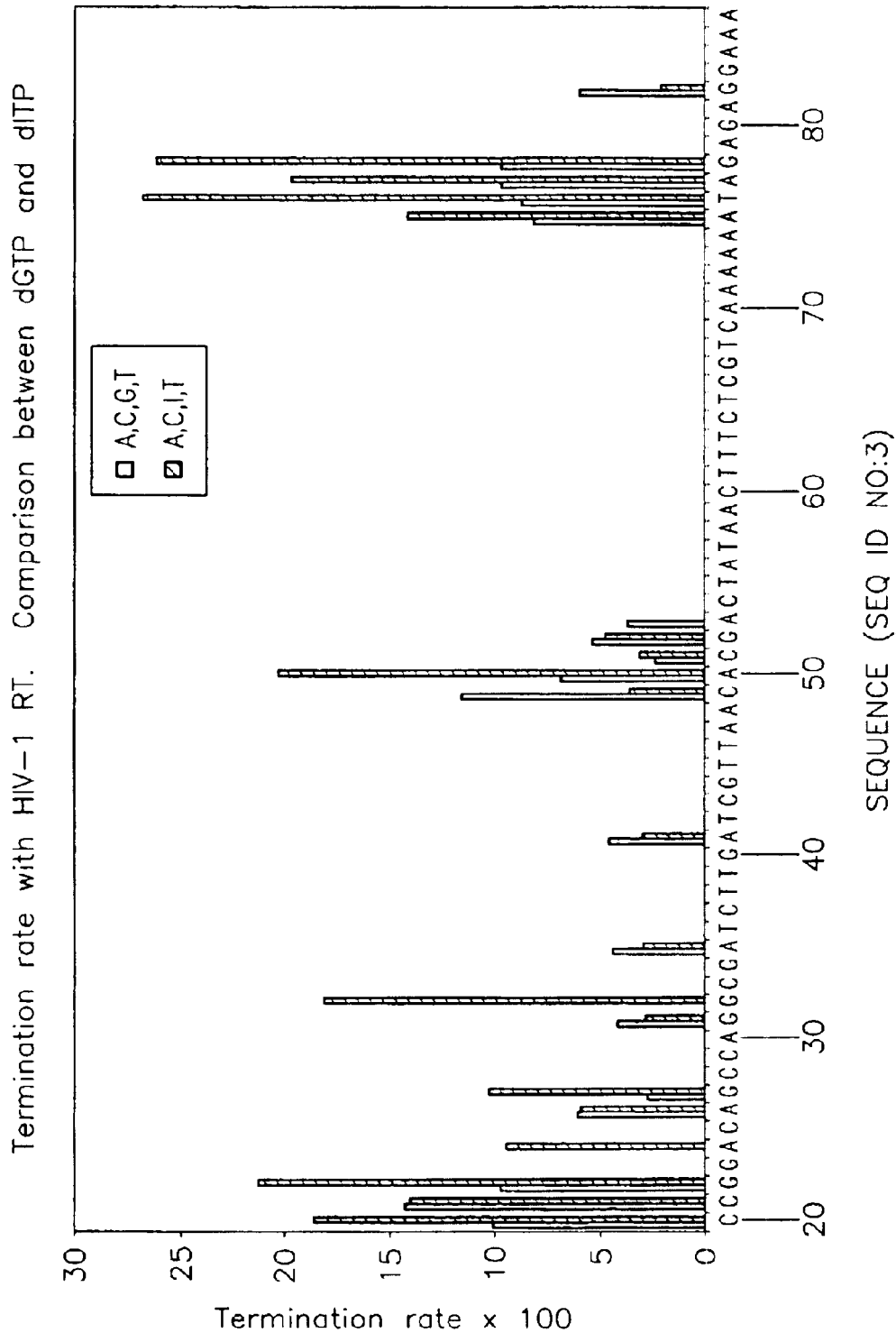
FIG. 2.2

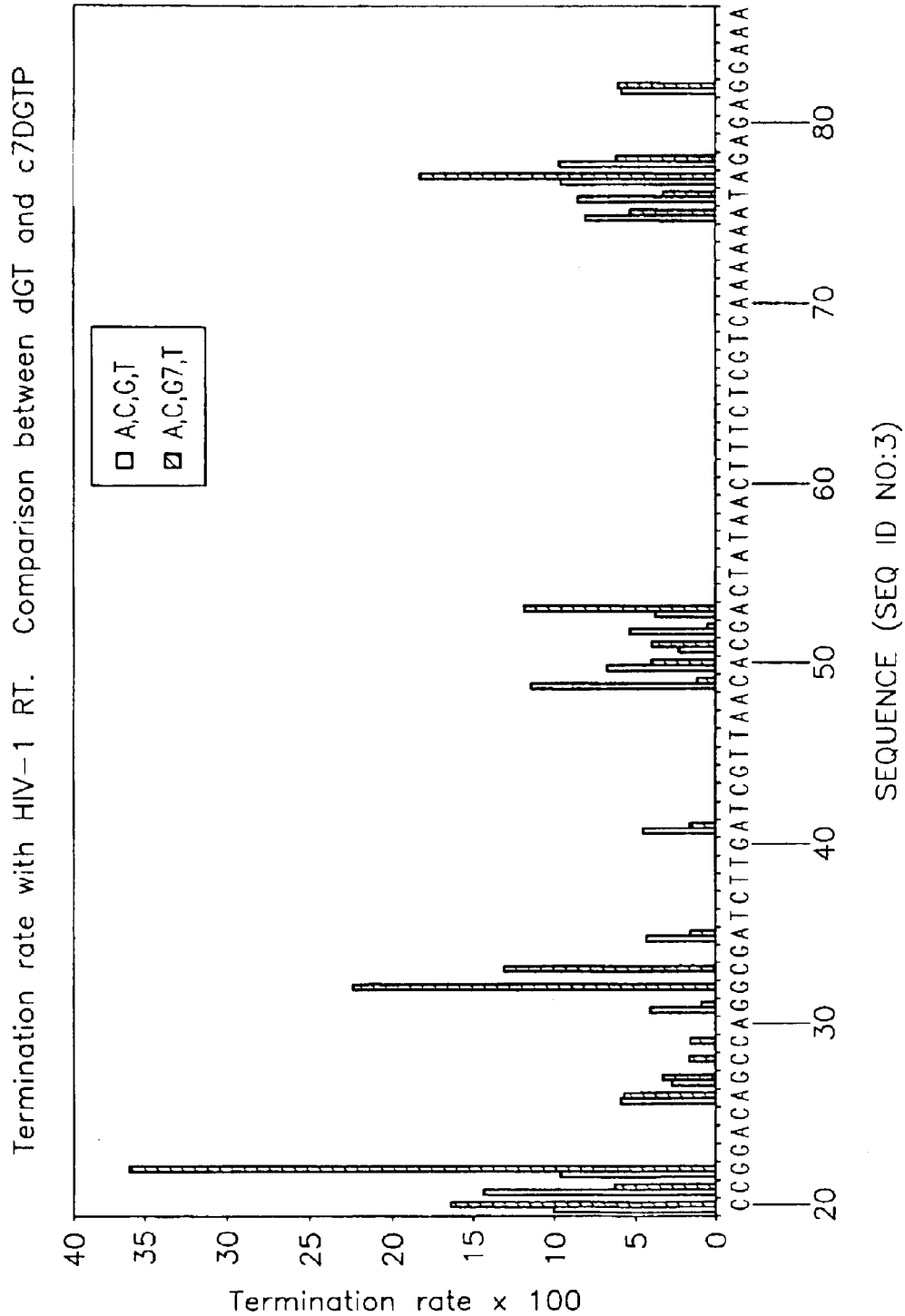
FIG. 2.3

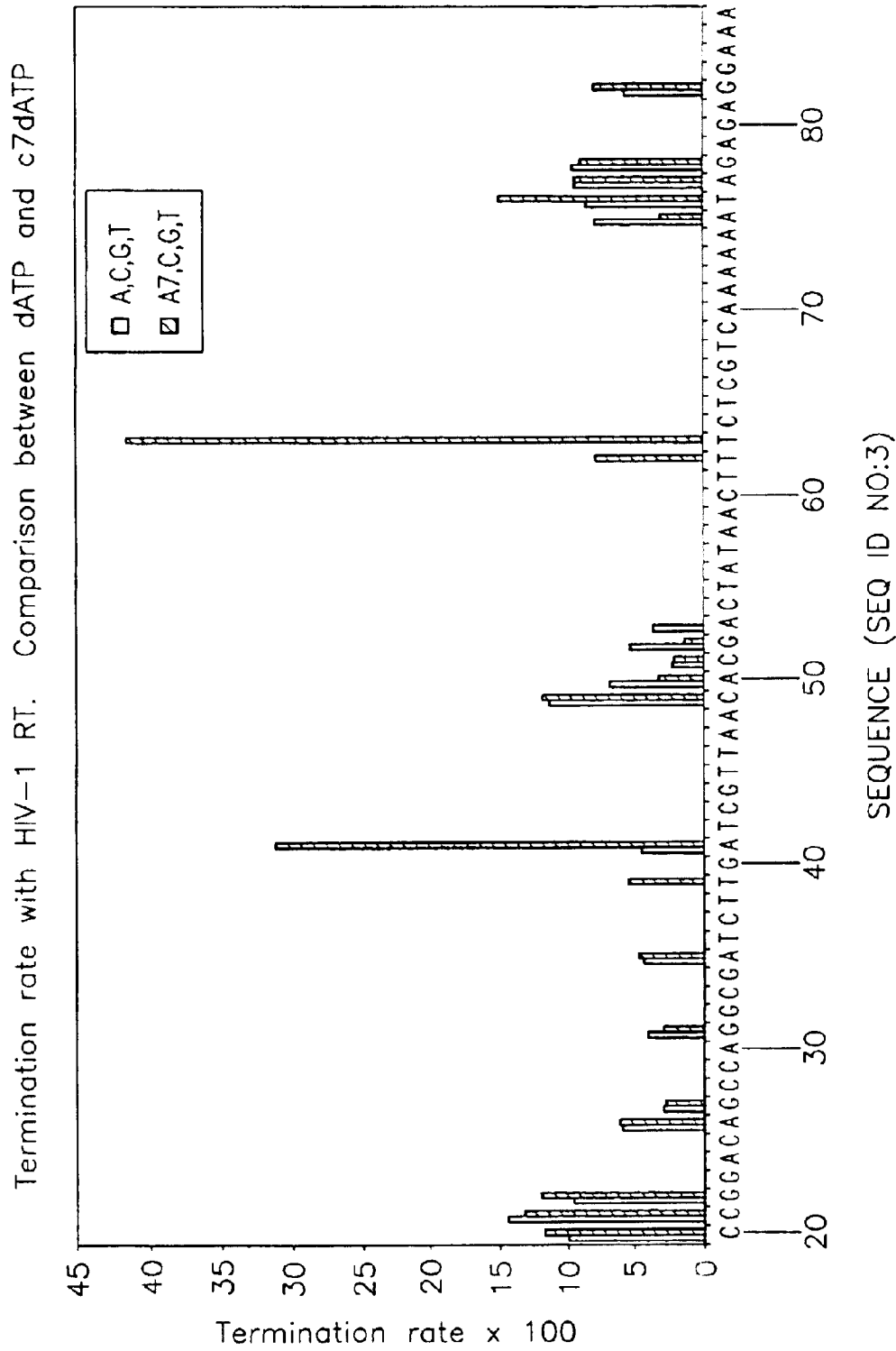
FIG. 2.4

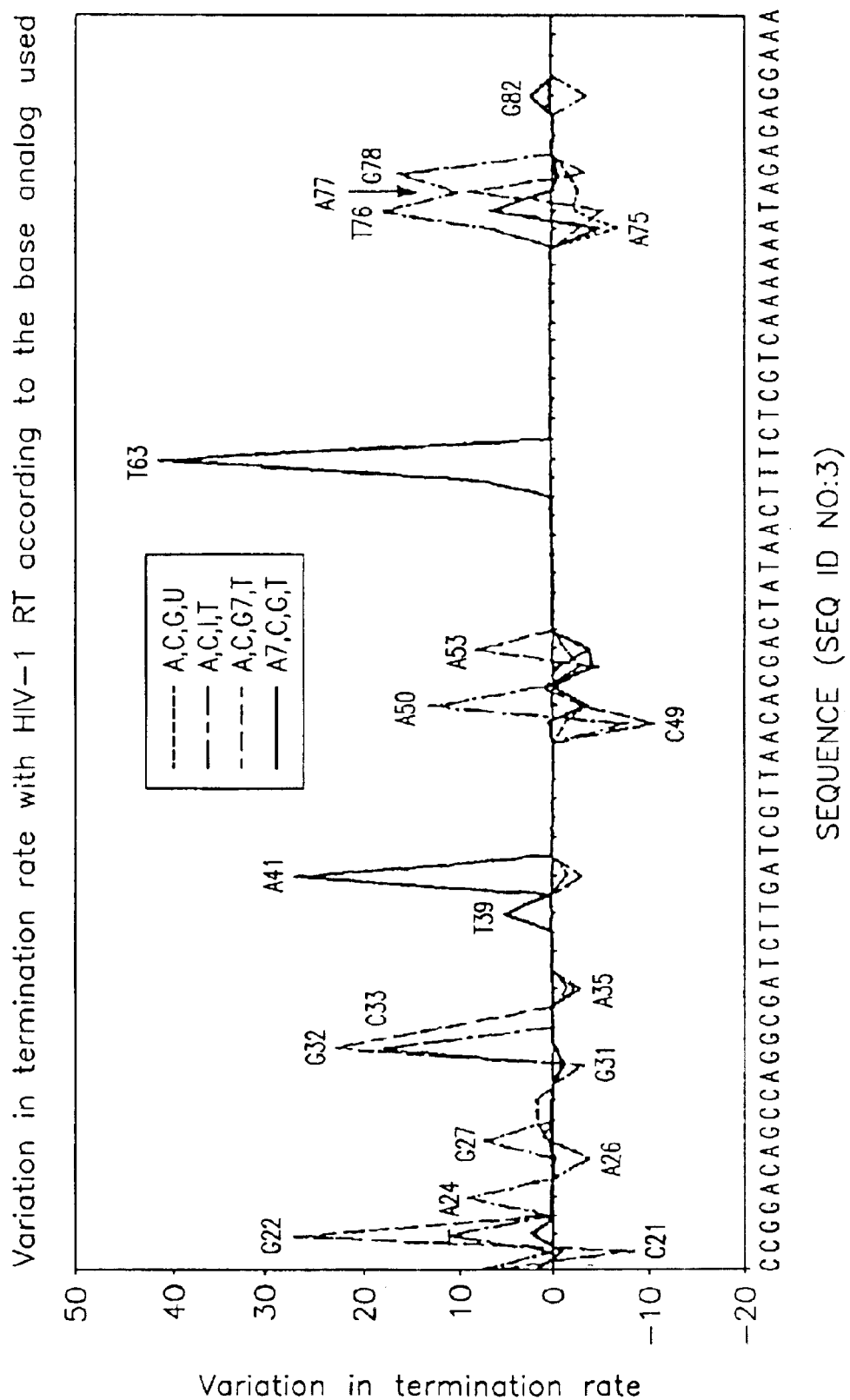
FIG. 2.5

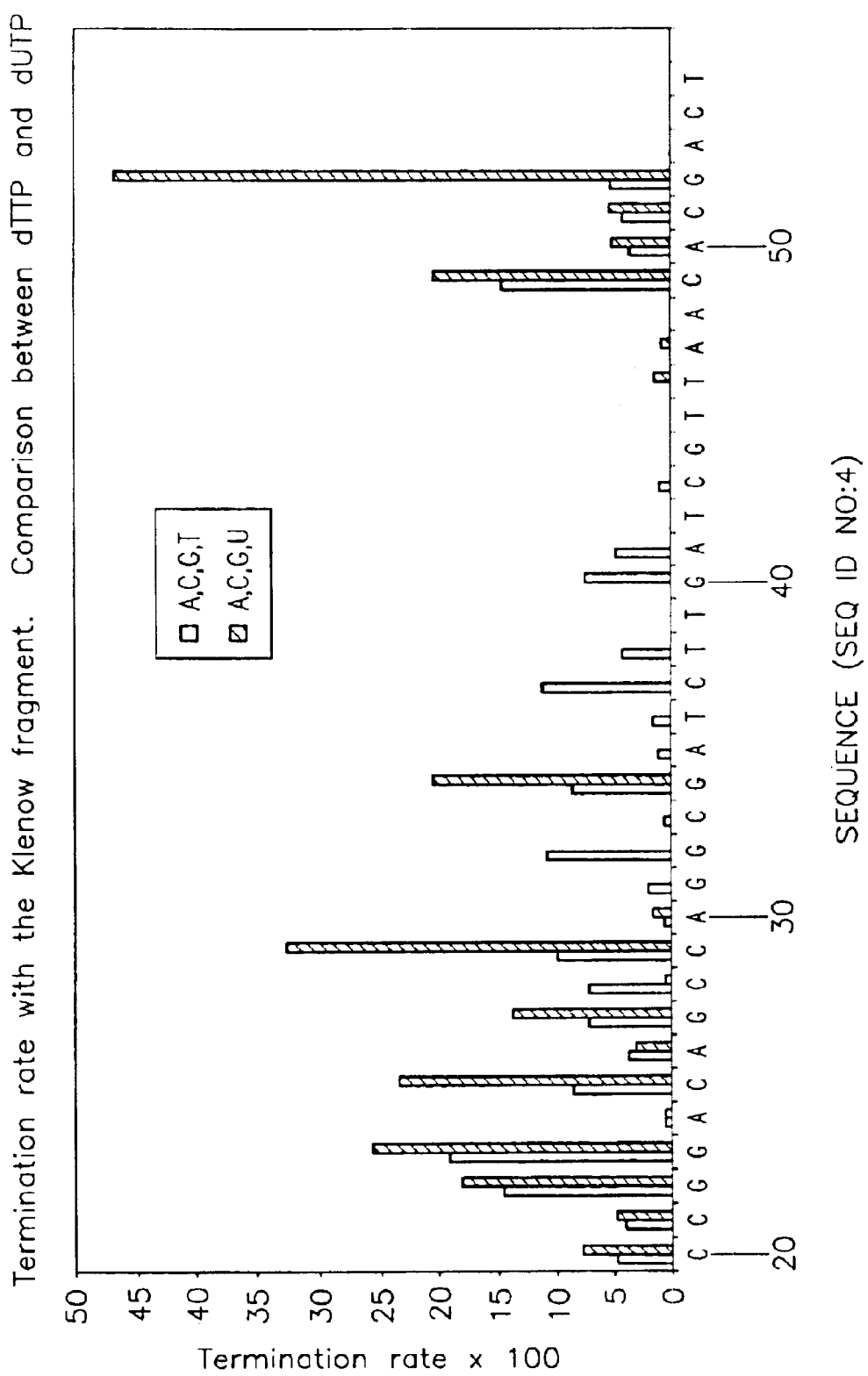
FIG. 2.6

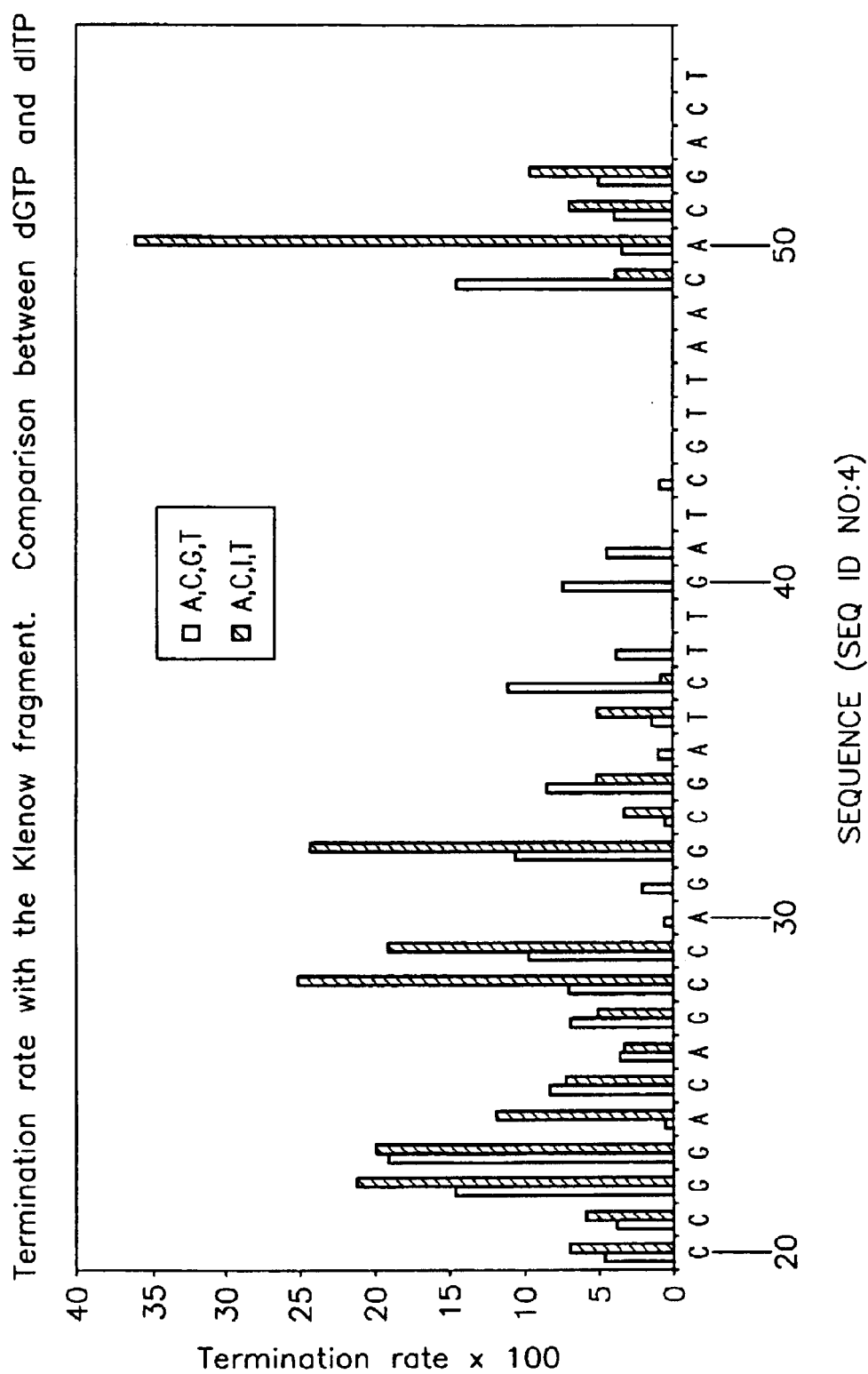

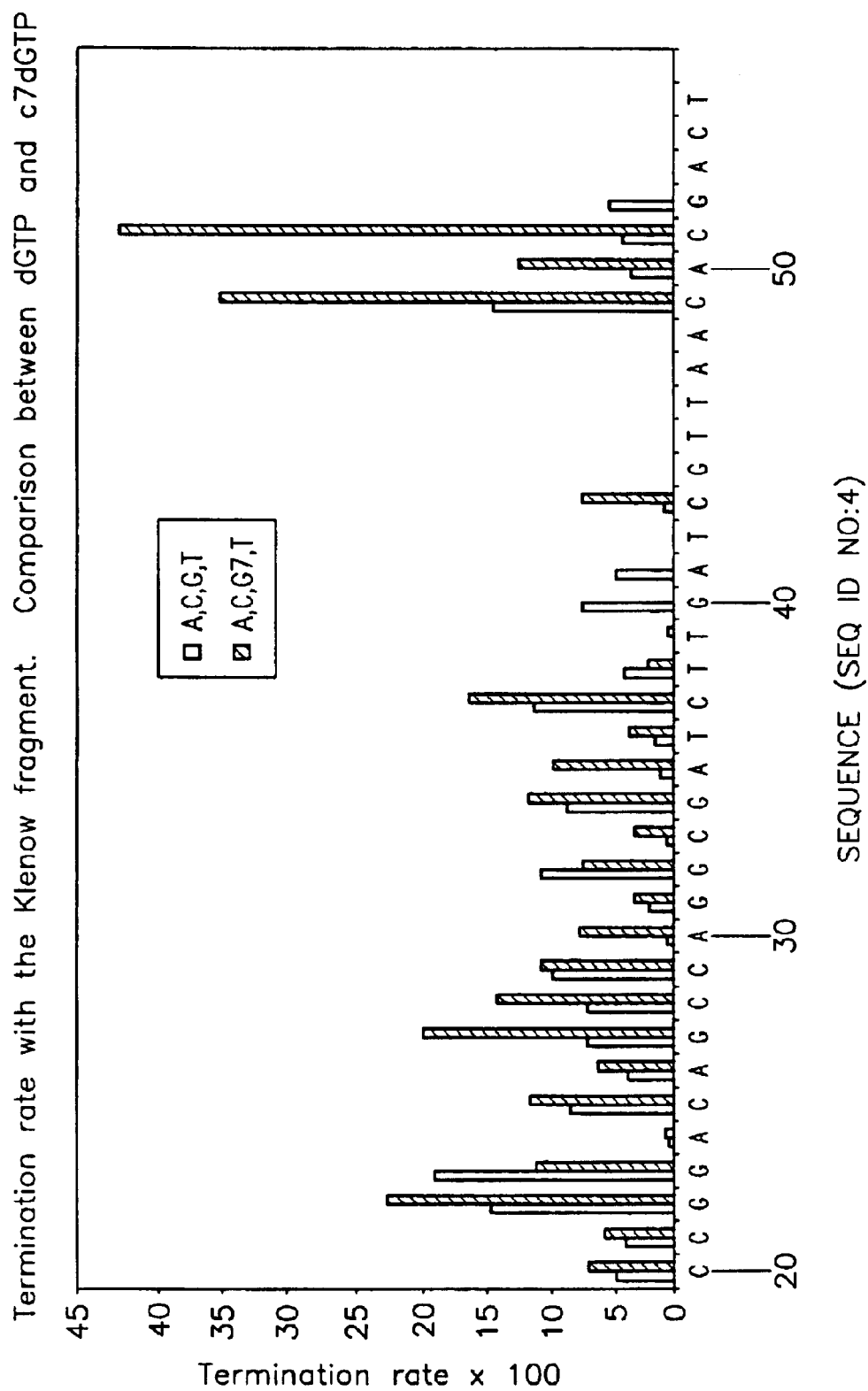

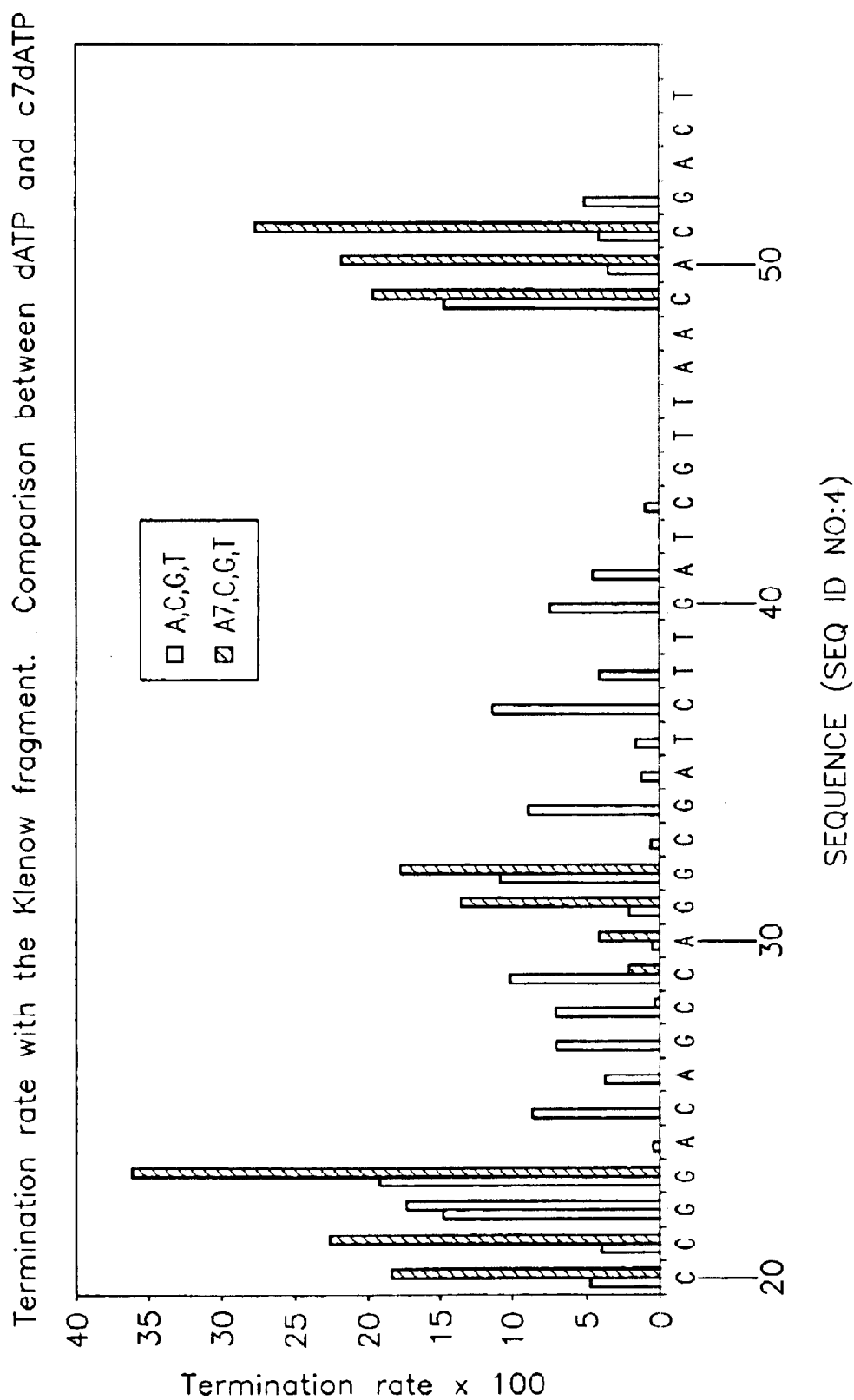
FIG. 2.9

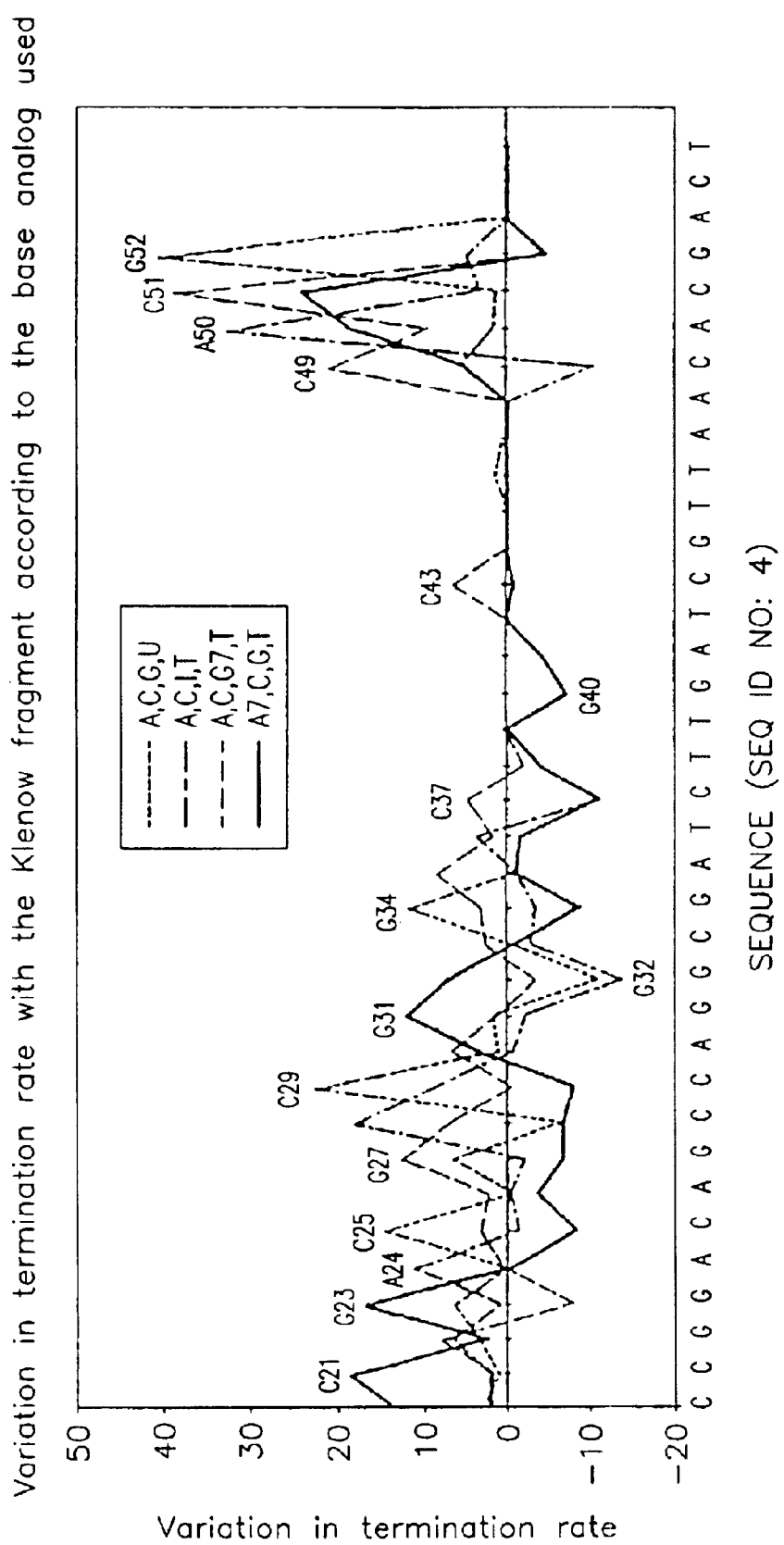
FIG. 2.10

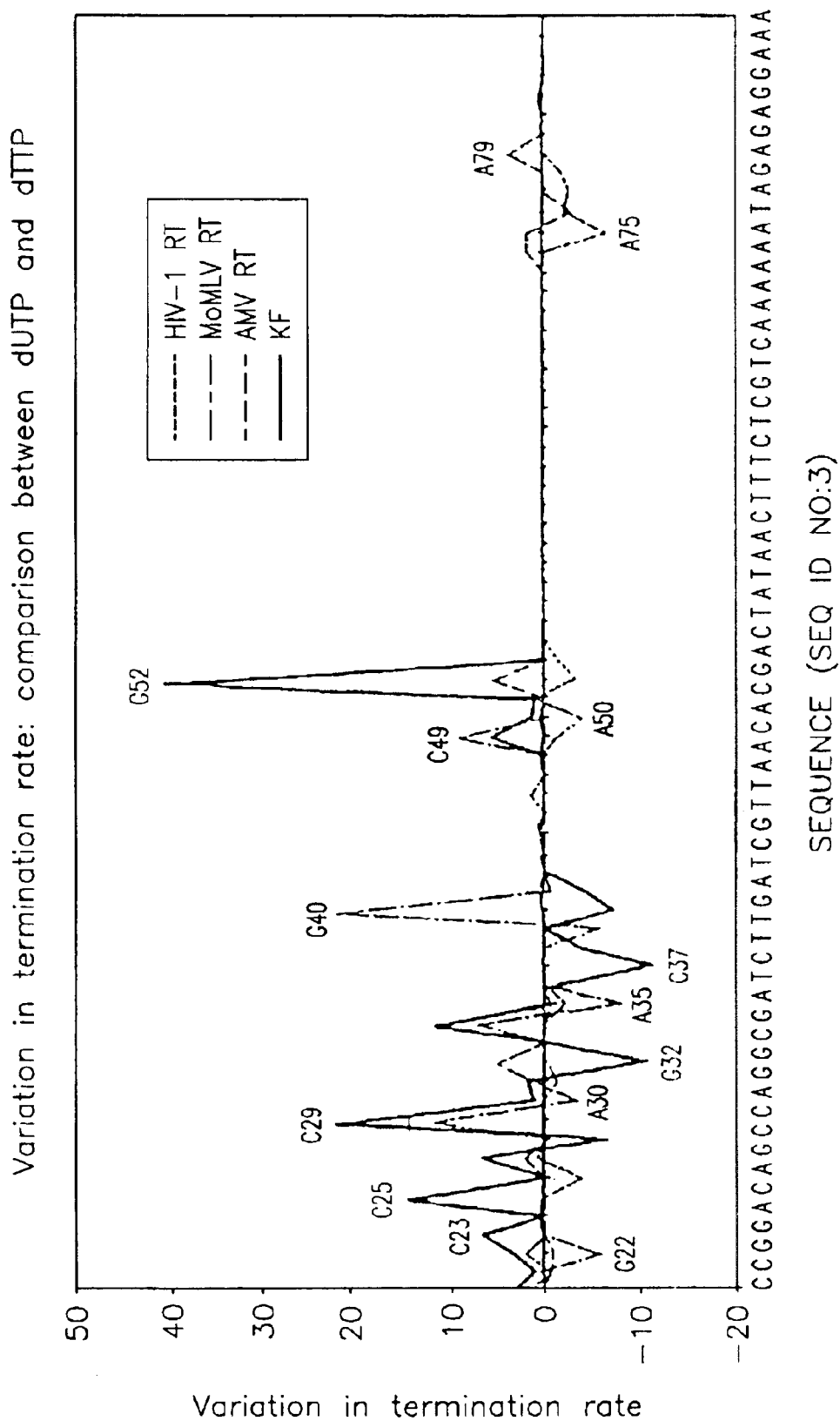
FIG. 3.1

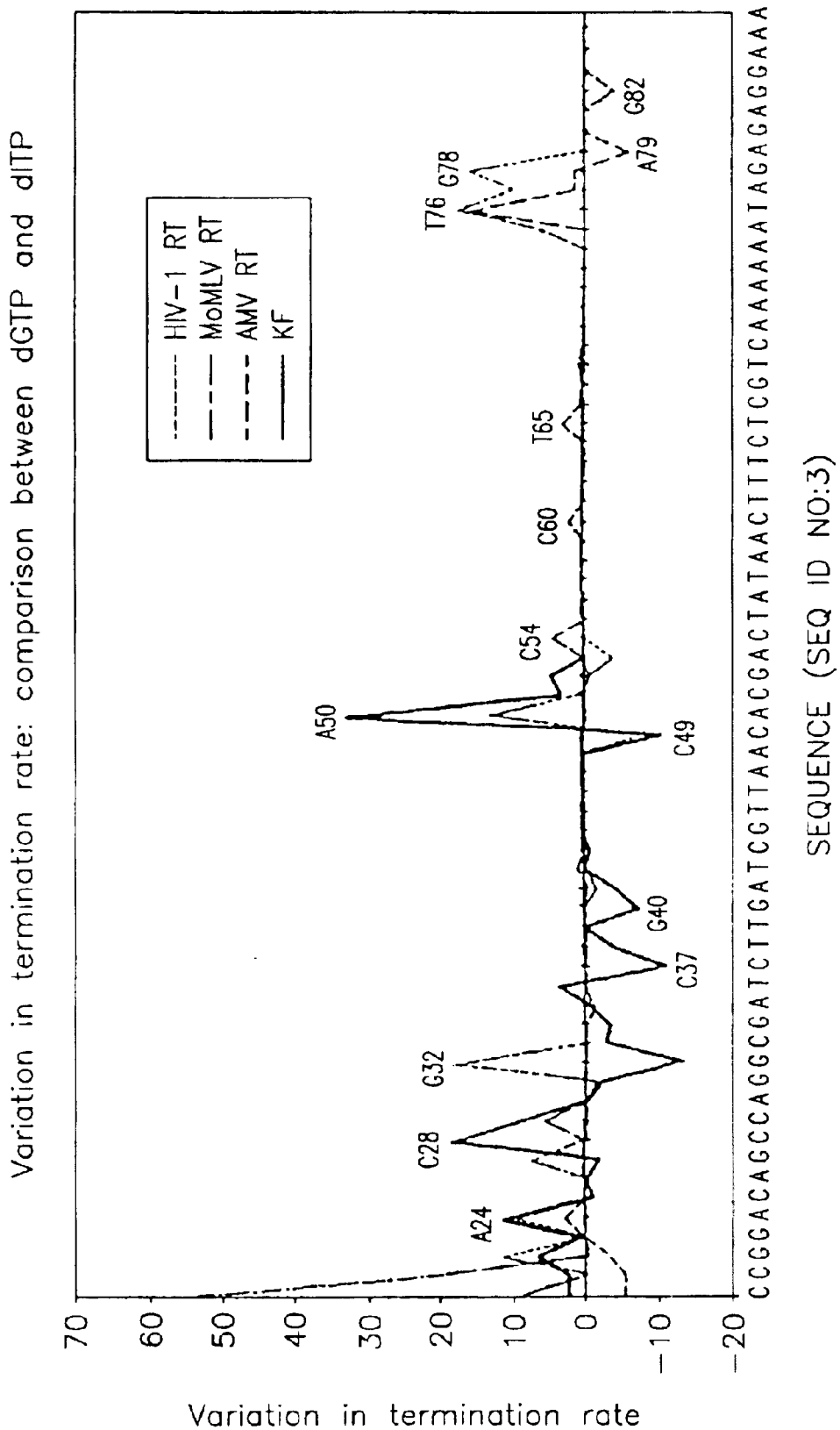
FIG. 3.2

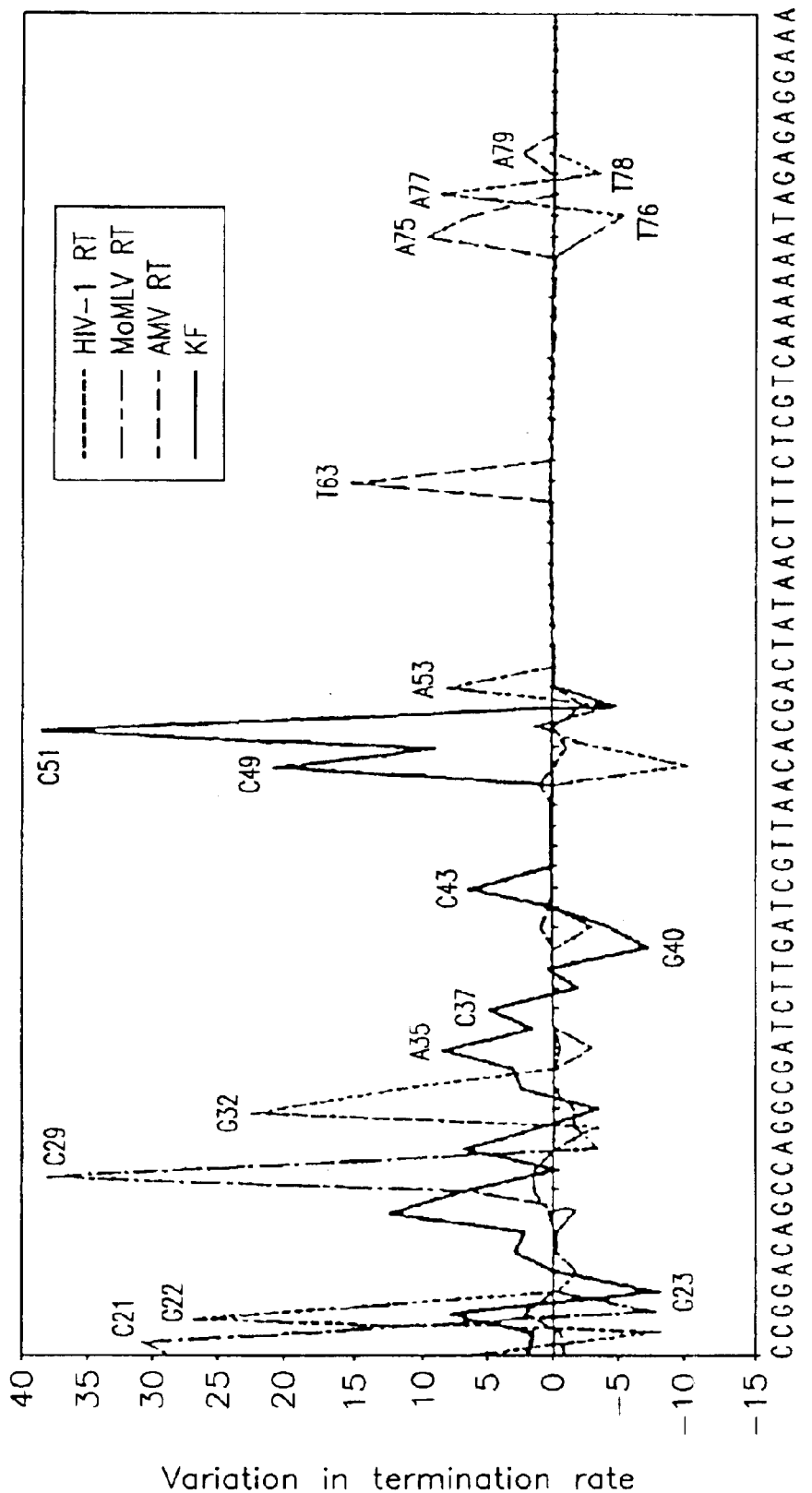
FIG. 3.3

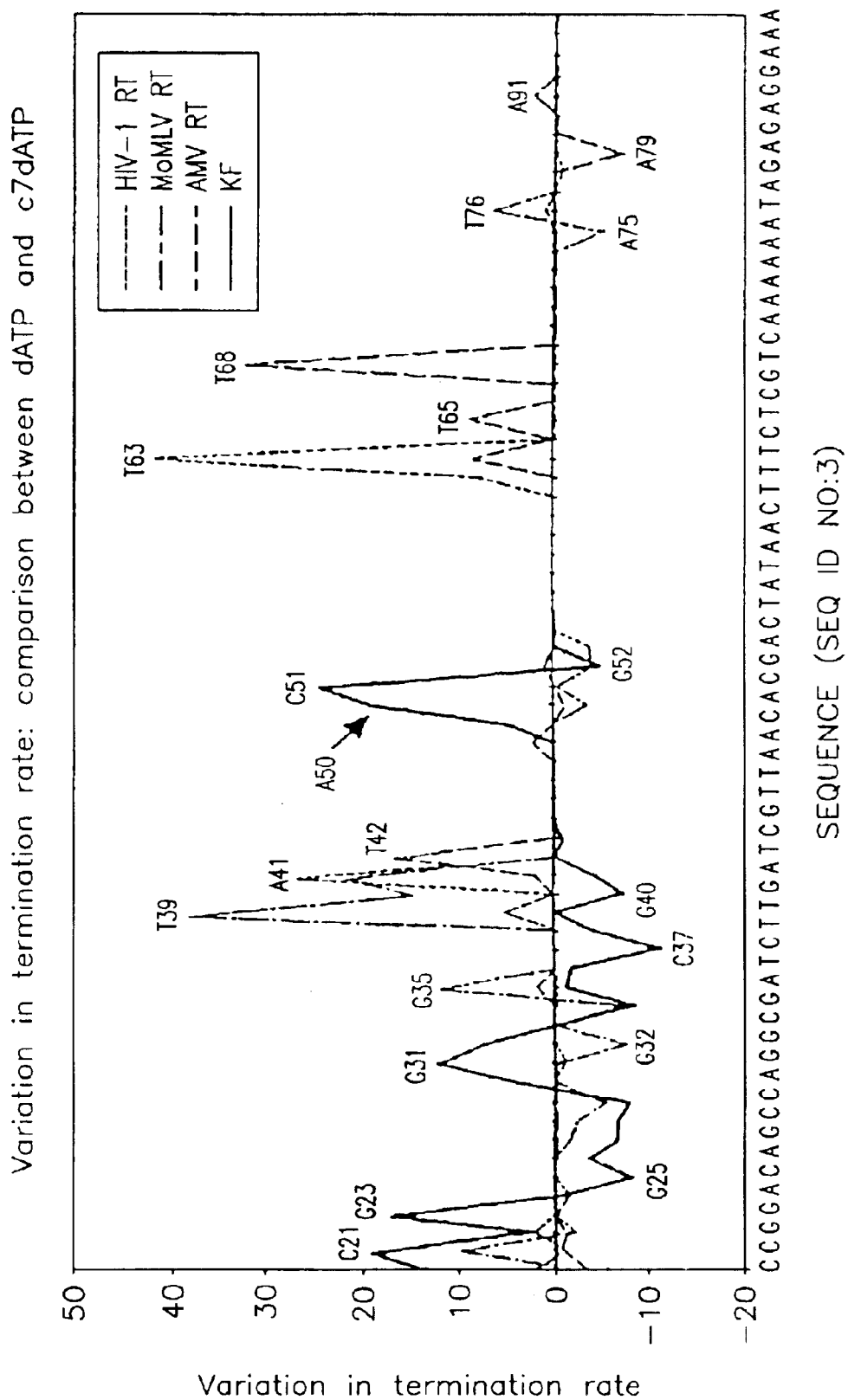
FIG. 3.4

TABLE 3.1

| Position | G22 | A26 | G31 | A35 | A41 | G52 | A75 | T76 | A77 | G78 | G82 |
|---|---|---|---|---|---|---|---|---|---|---|---|
| Variation | +++ | stable | − | − | − | stable | ++ | ++ | ++ | ++ | − |
| 1 | C | T | C | C | T | C | T | A | T | C | C |
| 2 | T | T | G | G | C | T | T | T | A | T | T |
| 3 | T | T | T | T | A | T | T | T | T | A | C |
| 4 | A | C | T | C | A | T | T | T | T | T | T |
| 5 | A | C | C | C | T | T | T | T | T | T | C |
| 6 | C | T | T | T | A | T | T | T | T | T | T |
| 7 | C | T | T | T | A | T | T | T | T | T | A |
| 8 | G | A | T | T | C | A | A | T | T | T | T |
| 9 | C | A | C | C | T | C | C | A | T | T | T |
| 10 | G | C | C | T | C | T | T | C | A | T | T |
| 11 | G | C | T | T | C | A | A | T | C | A | T |
| 12 | G | G | T | T | T | T | A | T | C | T |  |
| 13 | C | C | A | C | T | C | A | T | A | T |  |
| 14 | T | G | A | C | T | A | A | A | T | A |  |
| 15 | T | G | C | T | A | A | A | A | T | A |  |
| 16 | G | G | C | T | A | T | T | A | A | A | C |

TABLE 3.2

| Position | G22 | G31 | A35 | A41 | G52 | A75 | T76 | A77 | C778 | G82 |
|---|---|---|---|---|---|---|---|---|---|---|
| Variation | +++ | – | – | – | – – | – | + | – | | stable |
| 1 | C | C | T | T | C | T | A | T | C | C |
| 2 | G7 | T | G | C | G7 | T | T | A | T | T |
| 3 | G7 | G7 | G7 | A | T | T | T | T | A | C |
| 4 | A | G7 | C | A | G7 | T | T | T | T | T |
| 5 | A | C | C | G7 | T | T | T | T | T | C |
| 6 | C | T | T | A | T | T | T | T | T | T |
| 7 | C | G7 | G7 | T | A | G7 | T | T | T | A |
| 8 | G | T | G7 | C | A | A | G7 | T | T | T |
| 9 | C | C | C | G7 | C | C | A | G7 | T | T |
| 10 | G | C | T | C | G7 | G7 | C | A | G7 | T |
| 11 | G | G7 | G7 | C | A | A | G7 | C | A | T |
| 12 | G | G7 | T | T | G7 | A | G7 | C | T | T |
| 13 | C | A | C | G7 | C | A | G7 | A | G7 | T |
| 14 | T | A | C | G7 | A | A | A | G7 | A | G7 |
| 15 | T | C | G7 | C | A | A | A | A | G7 | A |
| 16 | G | C | G7 | T | G7 | G7 | A | A | A | C |

| Position | Variation | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| A50 | – | T | G | T | T | A7 | A7 | C | G | A7 | T | C | A7 | A7 | G | A7 | T |
| G52 | – | C | G | T | G | T | T | A7 | A7 | C | G | A7 | T | C | A7 | A7 | G |
| A53 | – | T | C | G | T | G | T | T | A7 | A7 | C | G | A7 | T | C | A7 | A7 |
| A77 | stable | T | A7 | T | T | T | T | T | T | G | A7 | C | G | A7 | G | A7 | A7 |
| G78 | stable | C | T | A7 | T | T | T | T | T | T | G | A7 | C | G | A7 | G | A7 |

TABLE 3.3

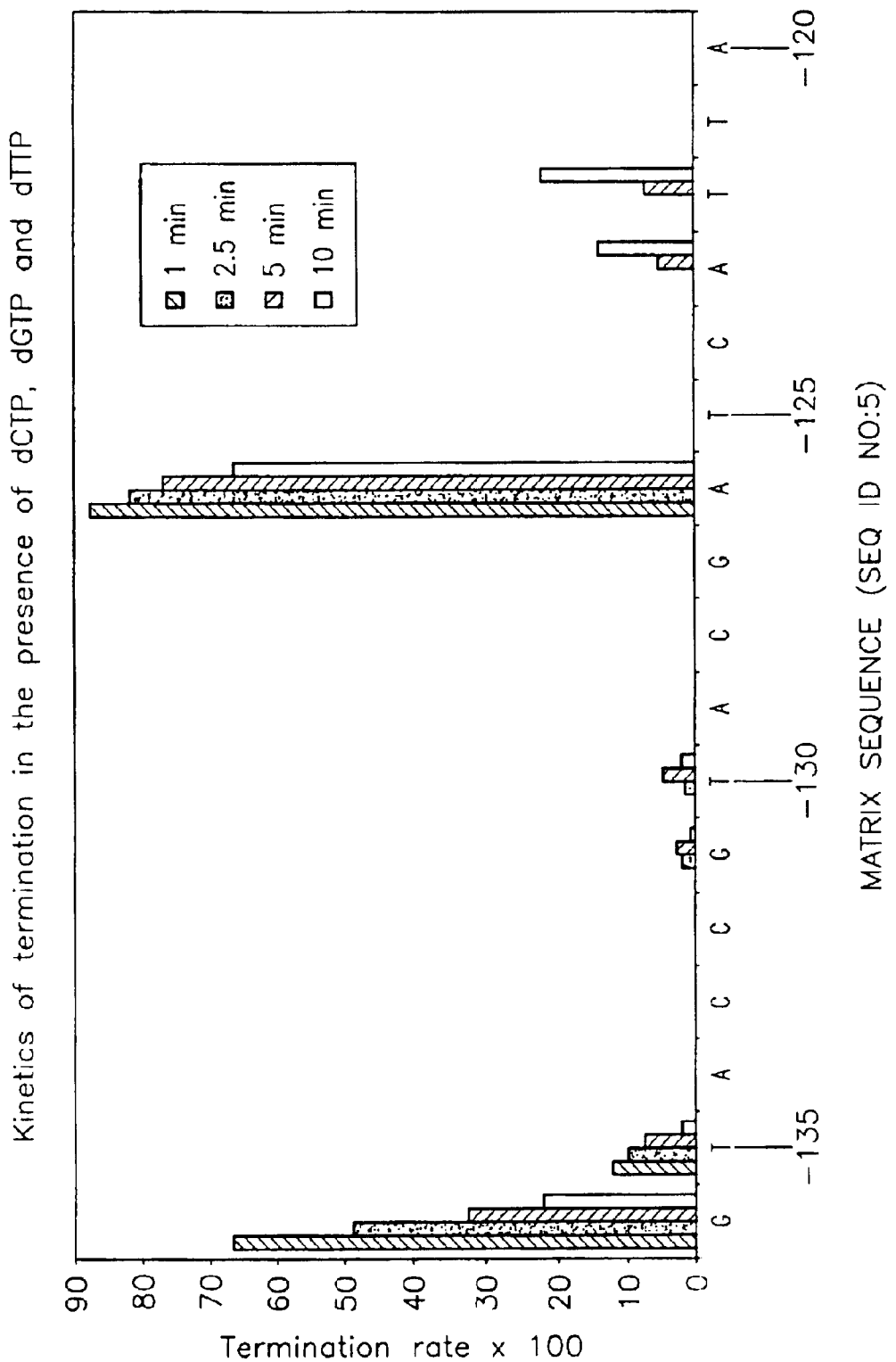
FIG. 4.1

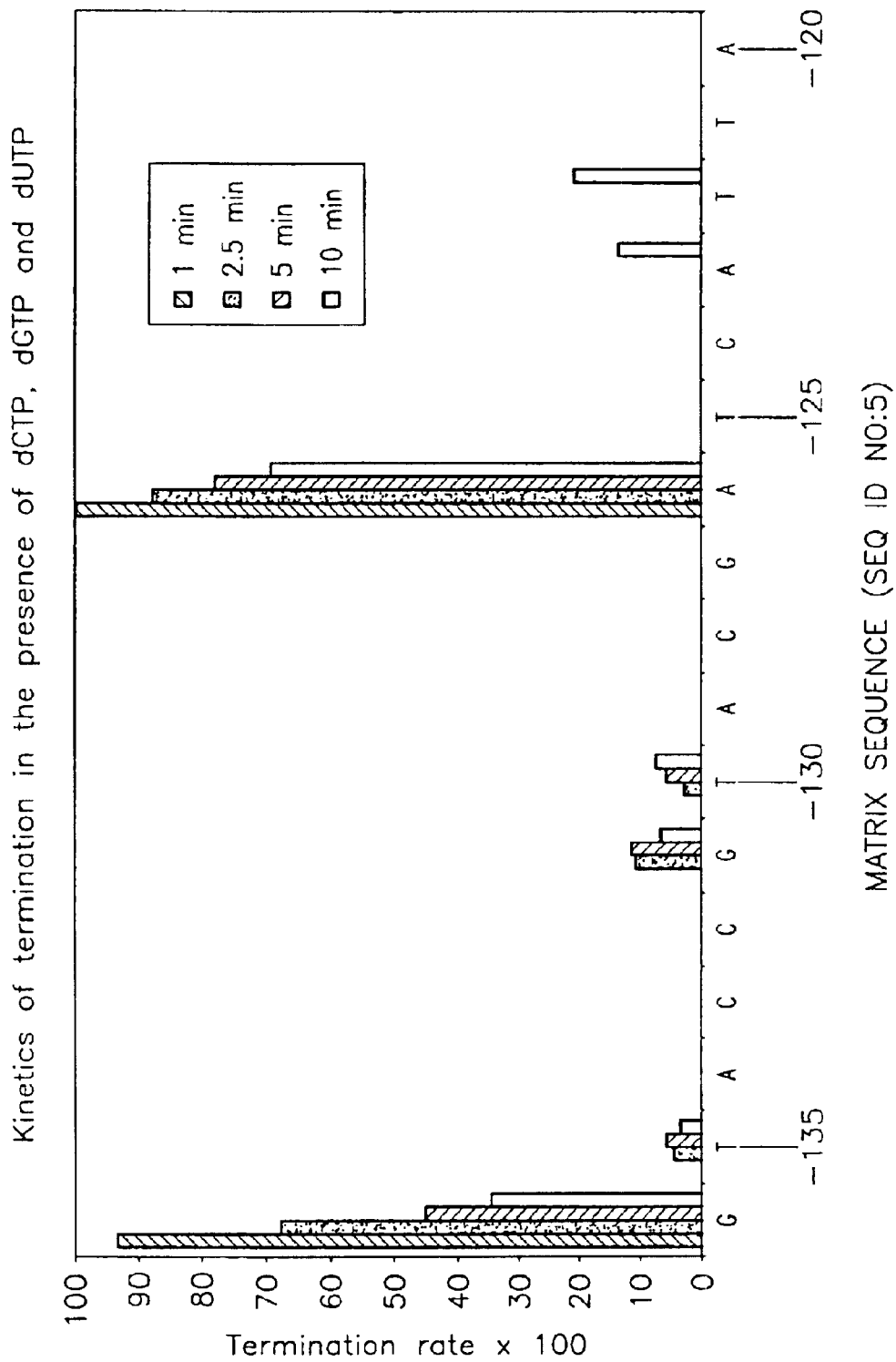
FIG. 4.2

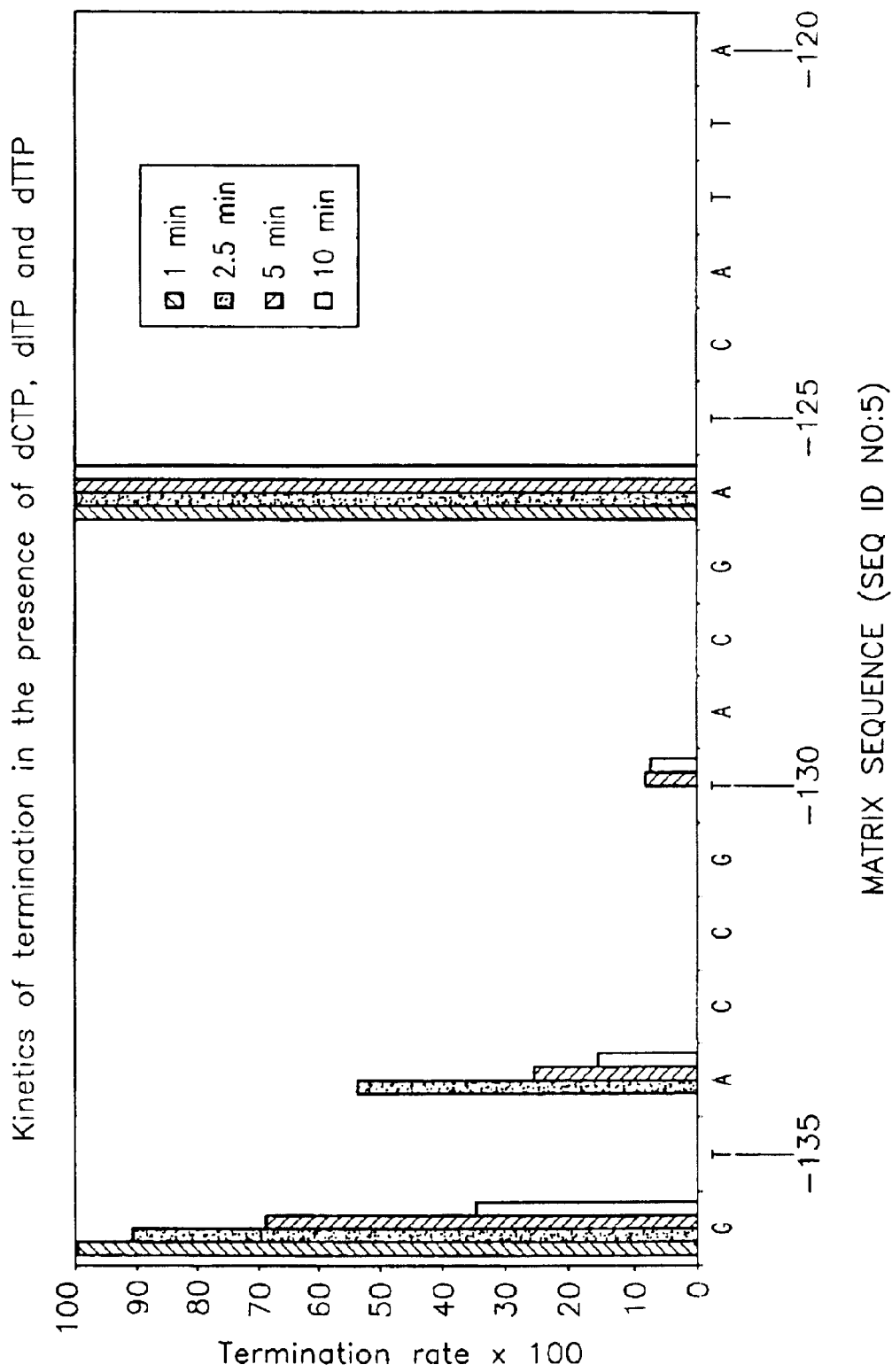
FIG. 4.3

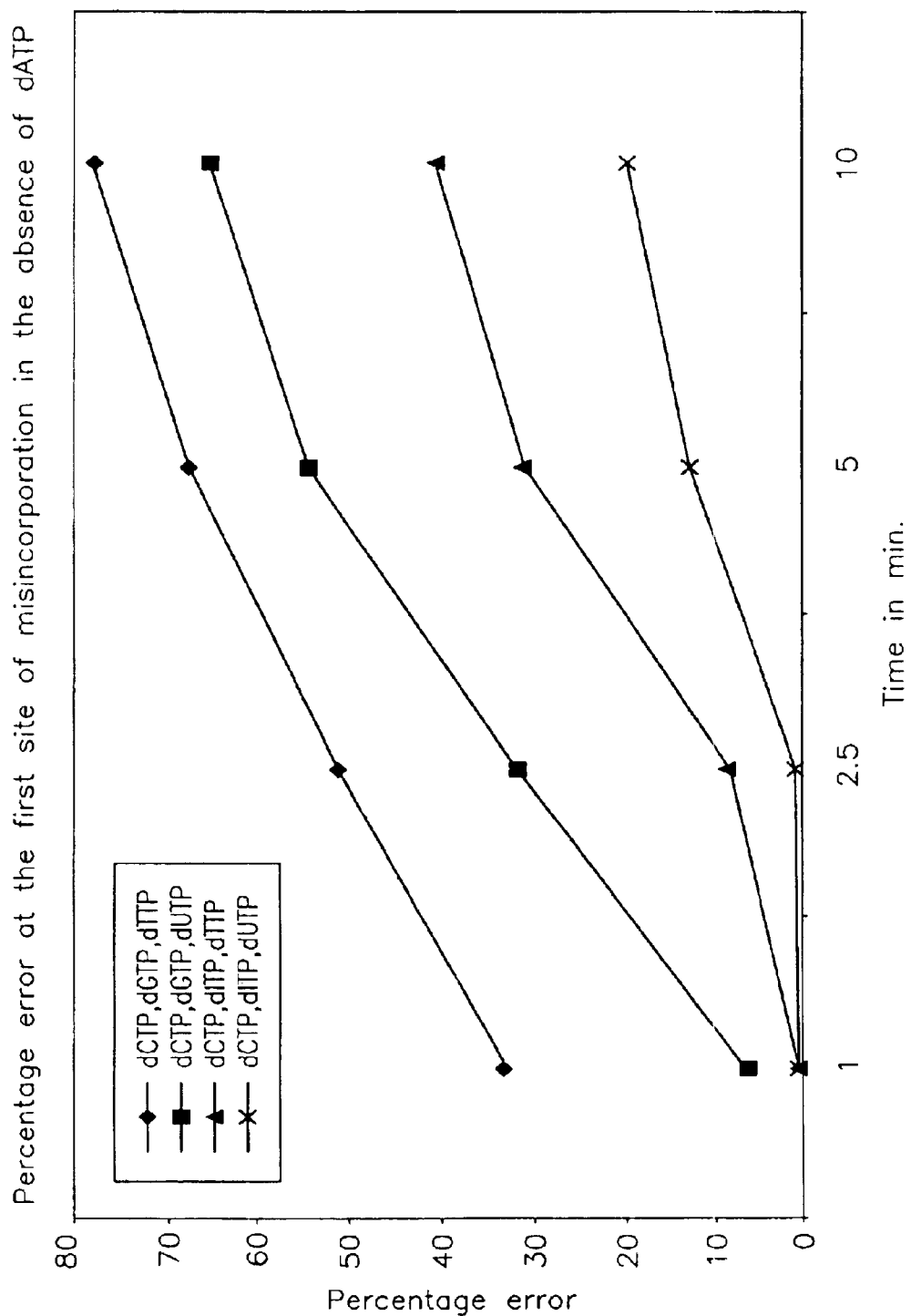
FIG. 4.4

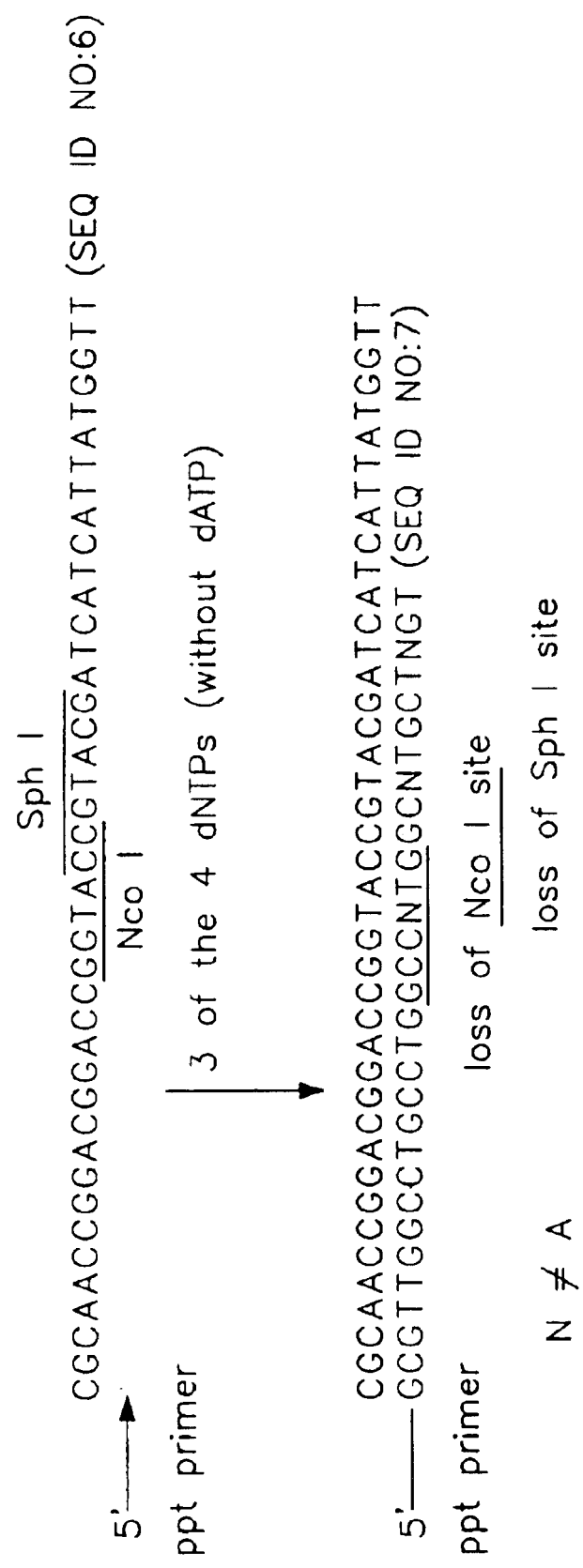
FIG. 4.5

| wild-type sequence 5'-GCCGTTGGCCCTGCCCTGGGCCATGGCCATGCTAATACCAA (SEQ ID NO:8) |
|---|
| Mutated sequence AMV RT |
| Mutated sequence HIV-1 RT |

FIG. 4.6

| wild-type sequence | 5'GCGTTGGCCTGCCTGGCCATGGCATGCTAGTAATATACCAA (SEQ ID NO:9) |
|---|---|
| Mutated sequence HIV-1 RT | I<br>I<br>C<br>C                       C<br>I                       C<br>C                       C       T<br>C                       C       C |

FIG. 4.7

| wild-type sequence | 5'GCGTTGGCCTGCCTGGCCATGGCATGCTAGTAATACCAA (SEQ ID NO:9) |
|---|---|
| Mutated sequence HIV-1 RT | G    C    G    G<br>G    C    G    C<br>G    G    C<br>G    C    G    G<br>G    G    C    G<br>G    G    G    G |

FIG. 4.8

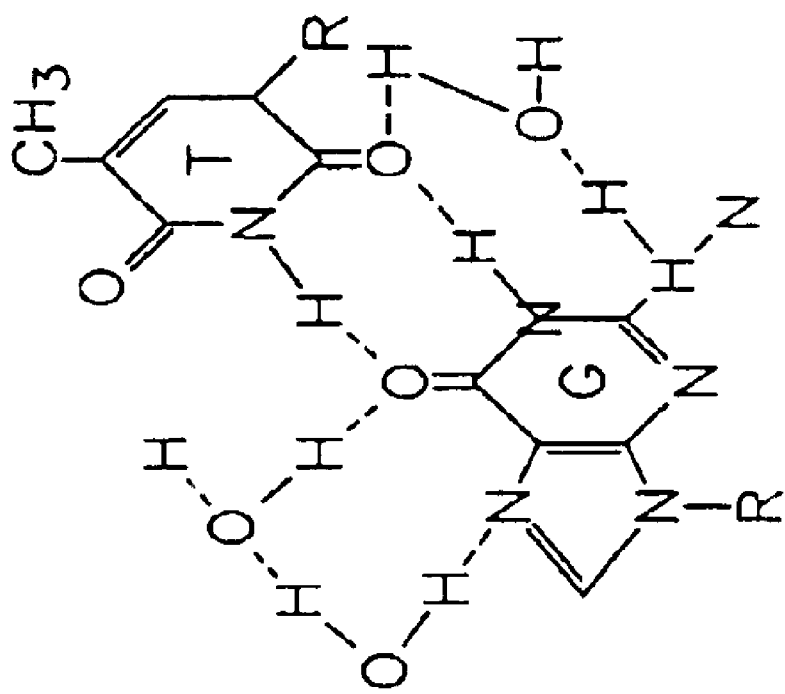
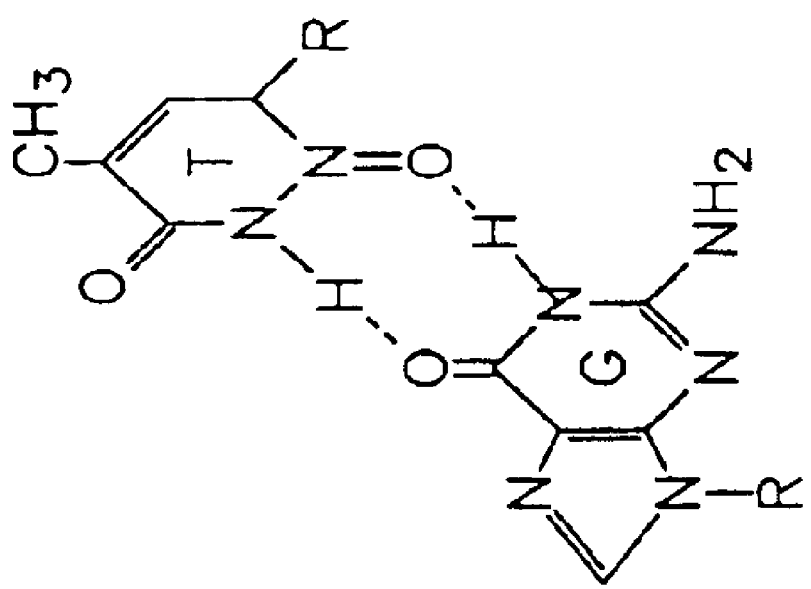
FIG. 4.9

(SEQ ID NO:10) matrix 3' GACGGACCCGGTACCCGTAGGA      step 1: polymerization as far as
(SEQ ID NO:11)            CTGCCTGGCCCGTGGC                    second site of misinsertion matrix 3' GACGGACCCGGTACCCGTAGGA                     step 2: displacement of primer
          CTGCCTGGCC                                          strand and insertion
                    T G       C
                     G       C
                      G C matrix 3' GACGGACCCGGTACCCGTAGGA                     step 3: realignment
          CTGCCTGGCCCGTGGC

FIG. 4.10

SEQUENCE LISTING

<160> NUMBER OF SEQ ID NOS: 11

<210> SEQ ID NO 1
<211> LENGTH: 171
<212> TYPE: DNA
<213> ORGANISM: Artificial Sequence
<220> FEATURE:
<223> OTHER INFORMATION: Description of Artificial Sequence: pbs primer

<400> SEQUENCE: 1

```
gtccctgttc gggcgccaag gcctgtcggt ccgctagaac tagcaattgt gctgatattg      60
aaagagcagt tttttatctc tcctttctcc atcatcattt ccccgctact actattggta     120
```

```
ttactagcat gccatggcca ggcaggccaa cgcgtgaatt agcccttcca g        171
```

<210> SEQ ID NO 2
<211> LENGTH: 171
<212> TYPE: DNA
<213> ORGANISM: Artificial Sequence
<220> FEATURE:
<223> OTHER INFORMATION: Description of Artificial Sequence: pbs primer

<400> SEQUENCE: 2

```
cagggacaag cccgcggttc cggacagcca ggcgatcttg atcgttaaca cgactataac    60
tttctcgtca aaaatagag aggaaagagg tagtagtaaa ggggcgatga tgataaccat   120
aatgatcgta cggtaccggt ccgtccggtt gcgcacttaa tcgggaaggt c            171
```

<210> SEQ ID NO 3
<211> LENGTH: 67
<212> TYPE: DNA
<213> ORGANISM: Artificial Sequence
<220> FEATURE:
<223> OTHER INFORMATION: Description of Artificial Sequence: -env sense
      strand from 3' to 5'

<400> SEQUENCE: 3

```
ccggacagcc aggcgatctt gatcgttaac acgactataa ctttctcgtc aaaaataga    60 gaggaaa                                                              67
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: -env sense
      strand from 3' to 5

<400> SEQUENCE: 4

```
ccggacagcc aggcgatctt gatcgttaac acgact                              36
```

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: -env sense
      strand from 3' to 5

<400> SEQUENCE: 5

```
gtaccgtacg atcatta                                                   17
```

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: -env sense
      strand from 3' to 5'

<400> SEQUENCE: 6

```
cgcaaccgga cggaccggta ccgtacgatc atcattatgg tt                       42
```

<210> SEQ ID NO 7
<211> LENGTH: 31
<212> TYPE: DNA
<213> ORGANISM: Artificial Sequence
<220> FEATURE:

```
<223> OTHER INFORMATION: Description of Artificial Sequence: +env strand
      from 5' to 3'
<221> NAME/KEY: mutation
<222> LOCATION: (19)
<223> OTHER INFORMATION: Wherein n is any nucleotide
<221> NAME/KEY: mutation
<222> LOCATION: (24)
<223> OTHER INFORMATION: Wherein n is any nucleotide
<221> NAME/KEY: mutation
<222> LOCATION: (29)
<223> OTHER INFORMATION: Wherein n is any nucleotide

<400> SEQUENCE: 7
gcgttggcct gcctggccnt ggcntgctng t                              31

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: wild-type
      HIV partial sequence

<400> SEQUENCE: 8
gcgttggcct gcctggccat ggcatggcat gctaatacca a                   41

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: wild-type
      HIV partial sequence

<400> SEQUENCE: 9
gcgttggcct gcctggccat ggcatgctag taataccaa                      39

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Matrix
      sequence

<400> SEQUENCE: 10
gacggaccgg taccgtagga                                           20

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: sequence
      showing polymerization as far as second site of misinsertion

<400> SEQUENCE: 11
ctgcctggcc gtggc                                                15
```

METHOD FOR CONTROLLING THE FIDELITY AND PROCESSIVITY OF REVERSE TRANSCRIPTASE BY INCORPORATION AND POLYMERIZATION OF NUCLEOTIDE ANALOGS ACCEPTED AS SUBSTRATES FOR THE REVERSE TRANSCRIPTION REACTION WITHOUT BLOCKING ITS ELONGATION

This is a nationalization of PCT/FR00/01260, filed May 10, 2000 and published in French.

The present invention in particular relates to the treatment of pathological conditions induced by retroid viruses, in particular HIV 1, using nucleotide analogs which modulate the fidelity and processivity of the reverse transcriptase of this virus.

The viruses responsible for the acquired immunodeficiency syndrome (AIDS) have been the subject of many studies since 1981, the date at which the disease was identified for the first time. AIDS is a public health problem for many countries in the world. Thus, in the USA for example, the number of declared AIDS cases exceeds 100 000 and the number of individuals infected has been estimated at more than one million. The propagation of the disease is accentuated by the number of chronic carriers of the virus responsible for AIDS who remain asymptomatic for many years, if not throughout their entire life, and are therefore unidentified sources of contagion. This disease can be transmitted sexually and via the blood.

AIDS is a disease which affects the host's immune system, thus favoring the appearance of opportunistic infections or pathological conditions against which a healthy immune system would have protected the host. When AIDS is declared death generally occurs two to three years after diagnosis, subsequent to a collapse of the patient's immune defenses and to multiple opportunistic infections.

It is very difficult to classify the AIDS viruses, given the extreme genetic and antigenic variability which they show; conventionally, it is accepted that two types of virus responsible for human AIDS exist: HIV-1 and HIV-2 (Fauci, 1998). The HIV-1 virus is the agent responsible for AIDS in Central Africa, in Europe, in the USA and in many other countries, while HIV-2 is predominant in the west of Africa. Precise comparative analysis of various viral genomes has shown that the HIV-2 virus is closer to the simian viruses of the macaque (SIVmac) and of the sooty mangabey (SIVsm) than to the human HIV-1 virus and its homolog in chimpanzees (SIVcpz). Besides the three types of simian virus, feline viruses and viruses in other mammals exist.

The AIDS viruses are part of the group of retroid viruses which have the major common characteristic of using, during the viral and infective cycle, a very particular enzyme, reverse transcriptase (RT). The characteristic of this enzyme is that it catalyzes the synthesis of a double-stranded DNA from a single-stranded RNA matrix. The diverse members of the retroid group comprise retroviruses (oncogenic and non oncogenic), hepadnaviruses (hepatitis viruses) and caulimoviruses (viruses of higher plants). Three subgroups are conventionally identified in the retrovirus group: RNA oncoviruses, lentiviruses (HIV) and spumaviruses.

Many efforts have been made to attempt to understand and identify the molecular bases of each step of the viral cycle of HIV in order to develop curative or preventative therapies for AIDS. The CD4 receptor is the molecule which has a predominant role during infection with HIV; this receptor is located at the surface of several cells of the immune system: helper T4 lymphocytes, monocytes and macrophages. This molecule interacts with high affinity with viral glycoproteins (gp120 for HIV-1 and gp140 for HIV-2) embedded in the external viral envelope. The virus enters the target cell carrying the CD4 receptor only in the presence of a cofactor (for example CCR5, CCR3 and CCR2b) which allows the viral envelope to fuse with the cell membrane (Alkhatib et al., 1996; Deng et al., 1996, Choe et al., 1996). When the virus infects the cell, its genomic RNA is released. The reverse transcriptase (RT) catalyzes proviral DNA synthesis in the cytoplasm within the hour following infection. After retrotranscription, the resulting double-stranded viral DNA molecule penetrates into the nucleus of the infected cell. Integrase P32 cleaves the genomic DNA of the host cell, thus allowing the open nuclear DNA to receive the proviral DNA (Kim et al., 1989; Sato et al., 1992). There do not appear to be, a priori, preferential regions of integration in the chromosomes of the target cells. Integration is followed by a long latency period and then the integrated provirus is expressed (transcription and translation of its genes). It is transcribed into RNA which will be used as a genome for new virions and also as messenger for the synthesis of viral proteins.

For multiple reasons, the mechanism of replication of HIV poses many problems for the production of an effective therapy. Specifically, by virtue of its integration into the cellular genome, the proviral DNA behaves like a genetic element of the host. In addition, the HIV virus is disseminated throughout the entire body, in the T lymphocytes, monocytes and macrophages and also in the central nervous system. Finally, the HIV virus possesses very great antigenic variability, of which there are two main causes: the low fidelity of the viral reverse transcriptase (Gojobori et al. (1985); Jolly et al. (1986)), which has no mechanism for error correction, and the high recombination rate of the viral genome linked to the diploid nature of this same genome (Pathak et al., 1990 a and b; Hu and Temin, 1990b).

The diverse curative therapies currently used clinically consist, mostly, of meeting the virus head on, either by blocking the activity of the reverse transcriptase or by inhibiting the activity of viral enzymes essential for infection or replication (proteases, integrases). Diverse conventional antiviral agents have been identified by systematic assessment (screening) of molecules improved by successive chemical substitutions after demonstration of an antiviral effect. More recently, the construction, based on crystallographic molecular models, of viral inhibitors, aimed at strict modification of their target, has been explored. These medicinal products are classified according to their site of action and their chemical structure. The most commonly used in clinical trials in multitherapy are nucleotide and non-nucleotide reverse transcriptase inhibitors.

The nucleotide analogs developed to date interfere with infection by HIV and its replication via specific incorporations which inhibit the reverse transcriptase. Specifically, when the reverse transcriptase incorporates into the DNA chain, during synthesis, chemical compounds analogous to nucleotides blocked in 3', the molecule thus neosynthesized terminates with a site incapable of accepting the addition of another nucleotide. The truncated DNA has lost part of the genetic information and almost certainly its infectivity.

Among these agents, mention should be made of 3'-azido-3'-deoxythimidine (AZT), 2',3'-dideoxyinosine (ddI), 2',3'-dideoxycitidine (ddC), 2',3'-dideoxy-3'-thiacytidine (3TC), 2',3'-didehydro-2',3'-dideoxythymidine (D4T) and 2'-deoxy-5-fluoro-3'-thiacytidine (FTC). The clinical use of AZT makes it possible to decrease the frequency and seriousness of opportunistic infections and to reduce mortality in patients, but its not insignificant toxicity prohibits it being used continuously. Even though some analogs prove to be less toxic, such as dideoxyinosine (ddI), while at the same time being as active as AZT, the effectiveness of these agents remains limited in that the absorption of these antiviral agents causes side effects. In addition, due to its high mutation rate, the HIV virus rapidly becomes resistant to AZT and to the other nucleotide analogs during therapy. The emergence of resistants makes it necessary to increase the therapeutic doses administered to patients. It has thus been demonstrated that, after a certain amount of time, AZT may inhibit some cellular DNA polymerases at concentrations lower than those which inhibit HIV-1 reverse transcriptase, which explains the toxicity of these nucleotide compounds.

Another group of reverse transcriptase-specific inhibitors has been discovered more recently using a very different approach. Whereas research on nucleotide analogs follows a logical scheme based essentially on the properties of acting as a terminator of reverse transcriptase, the discovery of non-nucleotide inhibitors comes from systematically screening, in cells infected with HIV-1, for substances which are not toxic for uninfected cells. The first inhibitor discovered was TIBO (tetrahydroimidazo-(4,5,1-1, jk) (1,4)-benzodiapezin-2(1H)-one), followed by other compounds, such as HEPT (1-[(2-hydroxyethoxy)methyl]-6-phenylthiothymine), TSAO ([2',5'-bis-O-(tert-butyl-dimethylsilyl)-beta-D-ribofuranosyl]-3'-spiro-5"-(4"-amino-1",2"-oxathiole-2",2"-dioxide) and alpha-APA (alpha-anilinophenylacetamide). Other non-nucleotide inhibitors, such as nevirapine and BAHP (bis(ethero-aryl) piperazine) have been identified through their reverse transcriptase-inhibiting power in vitro. Unlike the nucleotide analogs, which are also active against other reverse transcriptases, the non-nucleotide inhibitors are extremely specific for HIV-1 reverse transcriptase; they do not affect the polymerases of HIV-2, the simian immunodeficiency virus SIV, of the feline immunodeficiency virus FIV and of avian and murine retroviruses.

The prolonged use of the current pharmaceutical compositions comprising nucleotide and non-nucleotide inhibitors leads, whatever the inhibitor used, to the development of variant retroviruses which exhibit resistance to these compounds. Thus, clinical studies have shown that approximately 60 to 75% of patients have, at an advanced stage of the disease, drug-resistant variants after one year of treatment with AZT (Japour et al., 1991).

The failure of the current curative therapies therefore requires the development of novel therapeutic strategies, for which reverse transcriptase remains a preferred target for combating retroviral infection. It must be clearly understood that the low fidelity of HIV reverse transcriptase admittedly leads to the production of a large number of virions which are non-infectious (but nevertheless immunogenic, therefore acting as a "decoy" for circulating lymphocytes), which might be considered to be a handicap for the virus, but it is precisely because of this low fidelity that the virus is capable of producing mutated strains which escape the circulating immune system, thereby constituting a major problem in developing an immunization strategy or finding a therapy.

Specifically, reverse transcriptases have a low polymerization fidelity due, in part, to the absence of a mechanism of error correction (proofreading activity). The considerable frequency of errors introduced by reverse transcriptases is therefore one of the main causes of viral mutations. The HIV reverse transcriptase, for example, makes, on average, one error out of 10 000, consequently conferring on the progeny a high mutation rate and a low infectivity titer due to the presence of a large number of noninfectious mutants. The rate of mutations introduced by the reverse transcriptase of this virus is of the order of 1 000 to 100 000 times greater than that observed for cellular DNA polymerases. However, while the vast majority of the virions are not infectious, those which are, are especially mutated in the non-vital genes encoding the immunogenic proteins of the viral envelope, i.e. the key proteins in a conventional immunization strategy. Thus, during each retroviral infection, millions of genetic variants may exist at the same time in an infected host (Domingo et al., 1985) and may thus escape the action of the immune system while waiting for the latter to react to the modified epitopes. It ensues therefrom a spiral of mutation of viral epitopes/production of antibodies directed against the viral epitopes; the virus, while sacrificing, in each reproductive cycle, most of its progeny, produces viral varieties which escape ambient immune defense since the virus cycle takes less than one day, whereas that of the immune response takes several days. This pursuit is all the more advantageous to the virus since the multiplication of the viral epitopes weakens and gradually exhausts the effectiveness of the immune response, the cells of which are the virus's target.

The present invention is based on the analysis of the method of action of reverse transcriptase.

HIV-1 reverse transcriptase has two subunits of 66 and 51 kDa (Di Marco Veronese et al., 1986). The P66 subunit possesses the polymerase and ribonuclease activities. Crystallographic and kinetic data show that HIV-1 reverse transcriptase has degrees of flexibility in the catalytic site in particular which allow quite a considerable amount of leeway in the relative positionings of the deoxyribonucleoside triphosphate (dNTP) being incorporated, of its matrix base and of the 3'OH end of the strand being formed. Moreover, the double helix is in conformation A for the last 5 base pairs formed and in conformation B beyond this, with a 40° bend between the two conformations. Some of the sequence constraints noted above give rise to permanent spontaneous conformational particularities (helix A for series of more than 4 to 5 purines, helix H for series of 3 and more adenines, bend at the junction between conformations B and A or B and H). The presence, in the 20 base pairs covered by the enzyme, of one or other of these sequence constraints may distance the dNTP from the 3'OH of the strand being formed, to the point of preventing elongation (loss of processivity), or present the dNTP to its matrix base in an arrangement which does not allow the complete Watson-Crick pairing required for fidelity. Experimental study shows precisely that the majority of misinsertions are compatible with Wobble pairings of the dNTP with its matrix base, which would be allowed by the flexibility of their relative positioning, determined mainly by the conformation of the double helix engaged in the enzyme.

This observation makes it possible to envision taking control of the expression and of the biological effects of the DNA fragment or of the genome reverse transcribed by using nucleotide analogs or other molecules accepted as substrates of polymerization by reverse transcriptase. The present invention therefore relates to the use of nucleotide analogs accepted as substrates by reverse transcriptase, for producing a medicinal product intended to treat conditions involving reverse transcriptase, characterized in that said nucleotide analogs have a 3'-OH group, which may or may not be protected, located on the C3' carbon of the 2'-deoxyribose, said group being capable of exchanging phosphodiester bonds with the chain being formed and the next nucleotide, and characterized in that said nucleotide analogs do not terminate the reverse transcription reaction. It should be clearly understood that the nucleotide analogs according to the invention are not immediate antiviral agents, i.e. agents which stop the viral cycle dead, but that they constitute agents which make it possible to take control of the execution (processivity) and accuracy (fidelity) of reverse transcription, retroviral reverse transcription in particular. The nucleotide analogs according to the invention take control of the genetic characteristics of the reverse-transcribed material.

The use of the nucleotide analogs according to the invention for producing a medicinal product intended to treat conditions involving reverse transcriptase differs from that of the nucleotide analogs of the prior art in that the action of the nucleotide analogs of the invention is deferred and does not cause blocking and immediate arrest of the synthesis of the chain being formed. Specifically, the reverse transcriptase-inhibiting nucleotide analogs of the prior art used as antiviral agents, among which mention should be made of AZT, DDC, DDI, D4T, 3TC, FddClUrd, carbovin, PMEA and PMPA, all lack the 3'-OH group on the C3' carbon of the deoxyribose, making the chain being formed, which has incorporated this chain-terminating nucleotide analog, incapable of exchanging a phosphodiester bond with the next nucleotide. The use of such chain-terminating nucleotide analogs has been disclosed in various scientific publications of the prior art. Thus, the publications: De Clercq (1997), Morris Jones et al. (1997), Patick et al. (1997), Debyser and De Clercq (1996), De Clercq and Balzarini (1995, Il Farmaco, 50: 735–747) and Granier and Valantin (1998) refer to the use of chain-terminating nucleoside/nucleotide antiviral agents as mono- or multi-therapeutic agents. Moreover, the publication by Tong et al. (1997, Biochemistry 36 (19): 5749–5757) describes the use of chain-terminating nucleotide analogs in the triphosphate form for stabilizing the complex formed between the reverse transcriptase and the DNA molecule. Tong et al. mention only the use of dUTP and dITP for stabilizing the complex formed in order to study resistance to dissociation of the complexes as a function of the nucleotide triphosphate used, and at no time suggest a use according to the present invention. In addition, there is an article by MacIntosh and Haynes (1997) which speculates on the role of the viral UTPpyrophosphatase enzyme (dUTPase), which catalyzes the reaction of dephosphorylation of dUTP (triphosphate) to dUMP (monophosphate), as a means of avoiding cellular dUTPs being incorporated into the viral genome; in fact, primate retroviruses, which include HIV, do not have genes encoding a dUTPase. The authors suggest that other primate viruses, which encode dUTPase, compensate its absence in HIV; the authors also suggest combating infection with HIV by combating these viruses which are purveyors of dUT-Pase. Finally, the prior art mentions an international patent application WO 96/40166 which claims the use of nucleotide analogs for combating pathological hyper-proliferation of skin cells.

The term "nucleotide analogs" is intended to denote any nucleotide other than the "normal" nucleotides, namely adenylic or deoxyadenylic acid, guanylic or deoxyguanylic acid, cytidylic or deoxycytidylic acid, thymidylic or deoxythymidylic acid, and uridylic acid. The nucleotide analogs may be modified at any position in the nucleotides; the nucleotide analogs may be in the form of mono-, di- or triphosphate, which may or may not be modified, provided that these forms are accepted as a substrate by the reverse transcriptase. The nucleotide analogs according to the invention satisfy, more generally, two criteria: (i) they constitute a substrate of polymerization by reverse transcriptases; (ii) they do not block the reaction of nucleotide polymerization at the group located on the C3' carbon of the 2'-deoxyribose of the nucleotide analog incorporated; the molecules according to the invention allow the addition of at least one further nucleotide after incorporation into the polynucleotide chain being formed of a nucleotide analog according to the invention. In the remainder of the text, in the interests of simplicity, all of these molecules will be referred to as "nucleotide analogs", in the knowledge that the scope of the invention is not restricted to natural analogs and that it includes any molecule capable of these two activities, whether or not it contains a purine or pyrimidine base, whether or not it contains a pentose saccharide or whether or not it contains a phosphate.

The nucleotide analogs of the invention are characterized by their ability to continue the elongation of the nucleotide chain during synthesis, whereas the nucleotide analogs used in the prior art have chain-terminating activity.

The expression "condition involving reverse transcriptase" is intended to denote (i) all pathological conditions of viral ethiology caused by viruses which possess an enzyme having reverse transcriptase activity; this set of viruses constitutes the retroid virus group defined above; and (ii) all biological processes which make use of a reverse transcription step; they may be processes which involve the telomerase enzyme which has reverse transcriptase activity, it may involve phenomena of retro-transposition of mobile elements or of DNA sequences (LINE sequences for example).

The nucleotide analogs used in the present invention affect the many viral biological functions: the initiation, elongation and termination of reverse transcription, the fidelity and processivity of reverse transcription, the control of the integration of the reverse transcribed genome into the cellular genome, the expression and replication of the reverse transcribed genome and, where appropriate, viral production. The biological effects of these nucleotide analogs may manifest themselves immediately or subsequently, either during the ongoing phase of reverse transcription, or during one or other of the biological activities taking place during the reverse transcription cycle (genetic expression of the reverse transcribed genome, preparation of the following or subsequent reverse transcription cycle, retroviral cycle where appropriate) or during a subsequent reverse transcriptase cycle. The biological effects targeted above occur only if the nucleotide analogs have been introduced during the reverse transcription of the DNA(−) strand, the matrix of which is the viral RNA genome, and/or of the DNA(+) strand, the matrix of which is the DNA(−) strand. The fidelity and processivity of the reverse transcription in the presence of the nucleotide analogs are predominant factors in determining the biological effects.

The mechanisms and factors involved in the fidelity and processivity of the retroviral RT are, in fact, exploited by the virus when it uses normal nucleotides, according to a very precise dose, allowing it to walk the narrow ridge between two precipices; on one side, the viral progeny risks having an insufficient infectivity rate, owing to insufficient fidelity and/or processivity; on the other side, great genetic stability due to high fidelity and/or processivity will give rise to an antigenic stability which is sufficient for an effective immune response from the host. The present invention consists in using nucleotide analogs in order to take control of the fidelity and/or processivity of the reverse transcriptase so as to push the virus into one or other of the precipices. Thus, an increase in the fidelity and/or processivity obtained by using nucleotide analogs according to the invention has the effect of extending the delay between the current antigenicity and a new antigenicity, the consequence of which is an increase in the effectiveness of the circulating lymphocytes; conversely, a decrease in the fidelity and/or processivity, linked to the use of nucleotide analogs according to the invention, has the effect of reducing the titer of circulating infectious viruses.

One of the subjects of the invention is the use of nucleotide analogs for controlling at will the fidelity of reverse transcription.

The term "fidelity" is intended to denote the rate of error per base of the polymerase during the synthesis of a polynucleotide chain using a matrix strand. The term "error" is intended to mean: (i) the substitution of a base which corresponds to the replacement of a complementary base with a noncomplementary base (the complementary base of a matrix base A is T (DNA) or U (RNA), of a matrix base G is C, of a matrix base T (DNA) is A, of a matrix base U (RNA) is A, and of a matrix base C is G); (ii) the addition of one or more bases relative to the matrix base (insertion); (iii) the omission of one or more bases relative to the matrix base (deletion). The fidelity is therefore the sum of the nucleotides substituted, deleted or inserted by the reverse transcriptase (or on the occasion of genomic modifications), divided by the total number of nucleotides of the matrix strand reverse transcribed. The fidelity of HIV-1 RT, for example, is estimated at $10^{-2}$ to $10^{-7}$ per nucleotide in vitro (Preston & Garvey, 1992), and from $10^{-4}$ to $10^{-6}$ per nucleotide during a replication cycle in vivo, compared to $10^{-9}$ to $10^{-11}$ per nucleotide which is usual for cellular DNA polymerases. These means have a limited value since the mutations are not distributed randomly but are very preferentially concentrated at mutational "hot spots". Fidelity can be affected by the following mechanisms:

1) A modification of the probability of Watson-Crick (WC) pairing with the matrix base, consequently causing non-Watson-Crick pairings (i.e. mismatches) and thus modifying the substitution mutation rate. A certain number of factors can promote mismatches at the active site; mention may be made of: (i) the physicochemical factors at the active site which have an effect on the tautomerization or ionization of the nucleotides; (ii) the steric factors at the active site responsible for presenting the nucleotide triphosphate to the matrix base in a spatial arrangement which allows one of the many non-Watson-Crick pairings, including in particular Wobble pairing; (iii) the kinetic factors of the polymerization, such as the concentration of nucleotide triphosphate at the active site, which affect the probability of Watson-Crick pairing or of mismatching.
2) An omission in complementing one or more base(s) of the matrix, consequently modifying the deletion mutation rate.
3) An addition of one or more base(s) without matrix, consequently modifying the insertion mutation rate; a certain number of factors can promote deletion mutations and insertion mutations at the active site: (i) "frameshifts", made possible by the presence of short neighboring identical sequences (Bebenek K. & Kunkel, T. A. 1990 Proc. Natl. Acad. Sci. USA 4946–50), the frameshifts are often initiated by a non-Watson-Crick pairing; (ii) an unsuitable distance and/or spatial presentation of the 3'OH end of the strand being formed relative to the nucleotide triphosphate (at the active site) and/or the matrix base, possibly producing a deletion of a base if the distance is too great or an insertion of a base if it is too short; distance and spatial presentation are controlled, inter alia, by the precise conformation of the double helix of approximately 20 base pairs covered by the RT, this conformation depending on the sequence and/or on the presence of nucleotide analogs.
4) Genomic rearrangements and/or recombinations.

The nucleotide analogs make it possible to take control of the fidelity of the reverse transcription according to the mechanisms set out above. The conditions for taking control of the fidelity depend on the nature of the modifications of the nucleotide analog. One of the objects of the present invention is therefore to use nucleotide analogs to introduce controlled mutations of the bases, such as substitution mutations, deletion mutations or insertion mutations.

Another aspect of the present invention relates to the use of nucleotide analogs for controlling at will the processivity of reverse transcriptase.

The processivity is defined as the number of nucleotides incorporated into the neosynthesized strand before the enzyme dissociates from the reaction complex, whether or not the dissociation is preceded by a pause in the elongation of the reverse transcription. This dissociation is "spontaneous", i.e. it is not "forced" by the nucleotide being blocked in 3', which prohibits any elongation.

Various mechanisms exist which are capable of affecting the processivity of reverse transcriptase and which have in common the fact that they prevent the addition of the nucleoside triphosphate to the chain being formed, i.e. the reaction producing the phosphodiester linkage between the phosphate in 5' of the entering nucleotide and the OH group in 3' of the terminal nucleotide of the chain being formed. Mention may be made of the following mechanisms:

1—steric mechanism:

a)—the nucleotide triphosphate at the active site is too distant or is sterically incorrectly presented relative to the 3'OH of the chain being formed, the latter occupying a normal position in the RT, the cause of the disorder being inherent to the active site and/or to the nucleotide triphosphate, whether or not it is paired according to a Watson-Crick pairing;

b)—the nucleotide triphosphate at the active site is too distant or is sterically incorrectly presented relative to the 3'OH of the chain being formed, the latter occupying an abnormal position in the RT due, for example, to an abnormal conformation of the double helix engaged in the RT;

c)—the leeway which the RT allows at the active site distances the nucleotide triphosphate from the 3'OH group, both being positioned correctly otherwise.

This steric mechanism is possible because of the flexibility of RTs; specifically, the distance between the gamma phosphate of the nucleotide and the 3'OH end of the strand being formed is not rigidly set. In addition, the domain which "covers" the double helix (leaving) exhibits a certain degree of freedom relative to the catalytic site and relative to the domain in contact with the matrix strand entering the enzyme (for example HIV-1); finally, for the RTs for which the catalytic mechanism is known (for example HIV-1), a dysfunction of the translocation of the nucleotide to be incorporated from the site of entry to the catalytic site, resulting in the addition of the nucleotide being prevented, may also affect the processivity. The nucleotide analogs may act on the processivity, bringing into play an unsuitable distance and/or spatial presentation of the 3'OH end of the strand being formed relative to the modified nucleotide at the active site and/or the matrix base, which may produce a deletion or an insertion of a base, depending on whether the modification decreases or increases the distance and/or spatial presentation, in such a way as to ignore a matrix base or to insert a base lacking a matrix base. Distance and spatial presentation are controlled, inter alia, by the precise conformation of the double helix of approximately 20 base pairs covered by the RT, this conformation depending on the sequence and/or on the presence of nucleotide analogs, and also by the rigidity or flexibility of the modified nucleotide triphosphate which is located at the active site.

2—kinetic mechanism:

A prolonged pause, due for example to too low a concentration of nucleotide triphosphate, causes the enzyme to leave the chain being formed. RTs are, in general, clearly less processive than DNA polymerases or RNA polymerases and have a spontaneous tendency to dissociate from the reverse transcription complex. The longer the duration of a pause of the reverse transcriptase (for any reason), the higher the probability of dissociation and therefore the greater the decrease in processivity at the site of pause.

The nucleotide analogs make it possible to take control of the processivity according to mechanisms similar to those set out above for normal nucleotides, but with controlled demultiplication of the effects of one and/or other of the diverse factors mentioned, depending on the modification present on the nucleotide analogs.

The present invention relates to the use of nucleotide analogs characterized in that said nucleotide analogs:
- decrease, in a controlled manner, the fidelity of the reverse transcription and/or lower, in a controlled manner, the processivity of the reverse transcriptase and/or decrease, in a controlled manner, the pause time of the reverse transcriptase;
- increase, in a controlled manner, the fidelity of the reverse transcription and/or increase, in a controlled manner, the processivity of the reverse transcriptase and/or extend, in a controlled manner, the pause time of the reverse transcriptase.

Among the conditions which involve reverse transcriptase are those caused by the reverse transcriptases of retroid viruses. Among the conditions caused by retroid viruses which can be treated with the nucleotide analogs used according to the present invention, mention should be made of the retroid viruses which infect humans and/or animals and/or plants, in particular the retoid viruses which infect human and/or animal cells, and which belong more particularly to the group of lentiviruses, RNA oncoviruses, spumaviruses and hepadnaviruses. According to a preferred embodiment of the invention, the lentivirus is chosen from the group consisting of the human immunodeficiency virus (HIV), and preferably human immunodeficiency virus type 1 (HIV-1), and human T-cell leukemia viruses (HTLV).

According to another preferred embodiment of the invention, the use of the nucleotide analogs according to the present invention is characterized in that the hepadnavirus is the hepatitis B virus (HBV). HBV is a DNA virus, but its genome goes into an RNA form when it is replicated; reverse transcription then takes place in order to give rise to the genomic DNA.

The present invention relates to use of the nucleotide analogs as described above and such that, when they are incorporated by reverse transcriptase into the polynucleotide chain, they introduce mismatches.

The term "mismatches" is intended to denote any pairings which do not very precisely respect Watson-Crick pairings. In the present invention, the term "Watson-Crick (hereinafter denoted WC) pairing" is intended to denote the pairing defined by the following hydrogen bonds (scheme 1):

a) for adenine (A)-uracyl (U) or thymine (T) pairings
  1) N6 of A donor of H6 to the acceptor 04 of U or T
  2) N1 of A acceptor of H3 from the donor N3 of U or T b) for guanine (G)-cytidine (C) pairings
  1) 06 of G acceptor of H4 from the donor N4 of C
  2) Ni of G donor of Hi to the acceptor N3 of C
  3) N2 of G donor of H2 to the acceptor 02 of C Any pairings which do not very precisely respect these hydrogen bonds between these 5 nucleotides, whether they respect them only partially, or they respect them but with other H bonds in addition, or they do not involve them, or one and/or other of the partners of the pair are not part of these 5 nucleotides (example, nucleotide with purine in which the N7 has been replaced with C7), define the set of pairings denoted, in the present invention, as "mismatches". Thus, the examples (scheme 2) illustrate in a nonlimiting way certain mismatches involving the 5 normal nucleotides:

1) the "reverse WC" A-T pairing
  N6 of A donor of H6 to the acceptor 02 of T
  N1 of A acceptor of H3 from the donor N3 of T 2) the "Hoogsteen" A-T pairing
  N6 of A donor of H6 to the acceptor 04 of T
  N7 of A acceptor of H3 from the donor N3 of U or T 3) the "reverse Hoogsteen" A-T pairing
  N6 of A donor of H6 to the acceptor 02 of T
  N7 of A acceptor of H3 from the donor N3 of T 4) the G or I-U or T "Wobble" pairing
  N1 of G or I donor of Hi to the acceptor 02 of U or T
  06 of G or I acceptor of H3 from the donor N3 of U or T It should also be mentioned that the normal bases may be in the form of tautomers, keto or enol forms for G and T, amino or imino forms for A and C; the frequencies of the enol and imino forms are low but not zero (of the order of $10^{-2}$ to $10^{-4}$) These tautomers have particular proton donor and acceptor characteristics (scheme 3) and can give rise to pairings such as T-G(enol), T(enol)-G, A(imino)-C or A-C (imino) (scheme 4).

Scheme 1

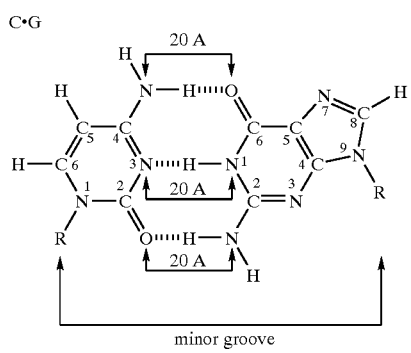

minor groove

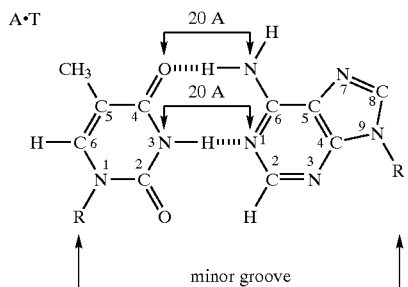
A·T
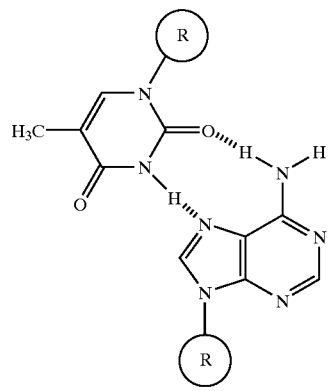
Reverse Hoogsteen (T·A)
Scheme 2
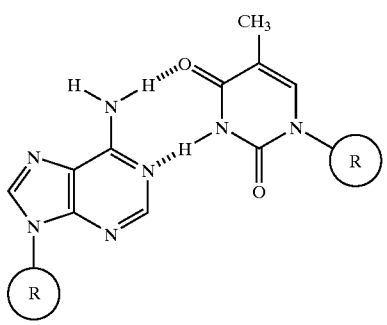
Watson Crick (A·T)
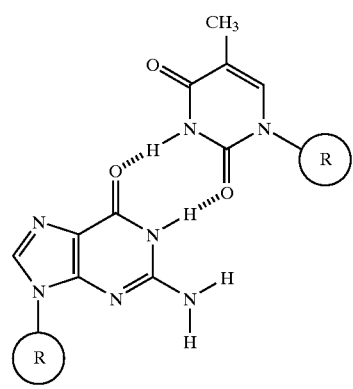
Wobble (G·T)
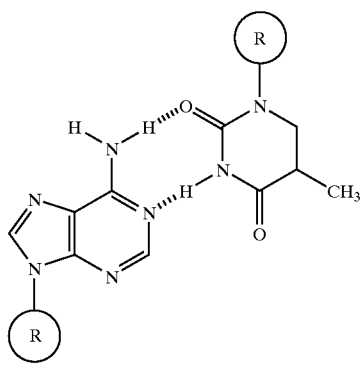
Reverse Watson Crick (A·T)
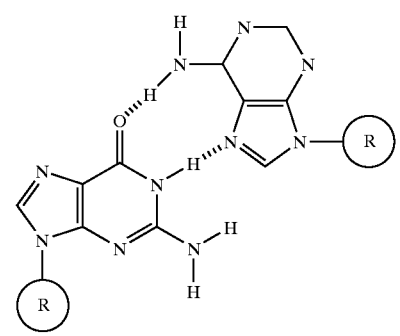
Guanine (Anti)·Adenine (Syn)
Scheme 3
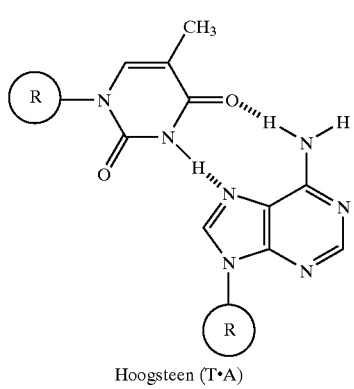
Hoogsteen (T·A)
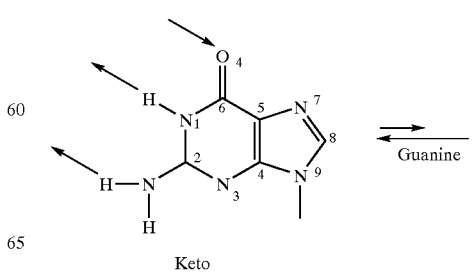
Keto ⇌ Guanine

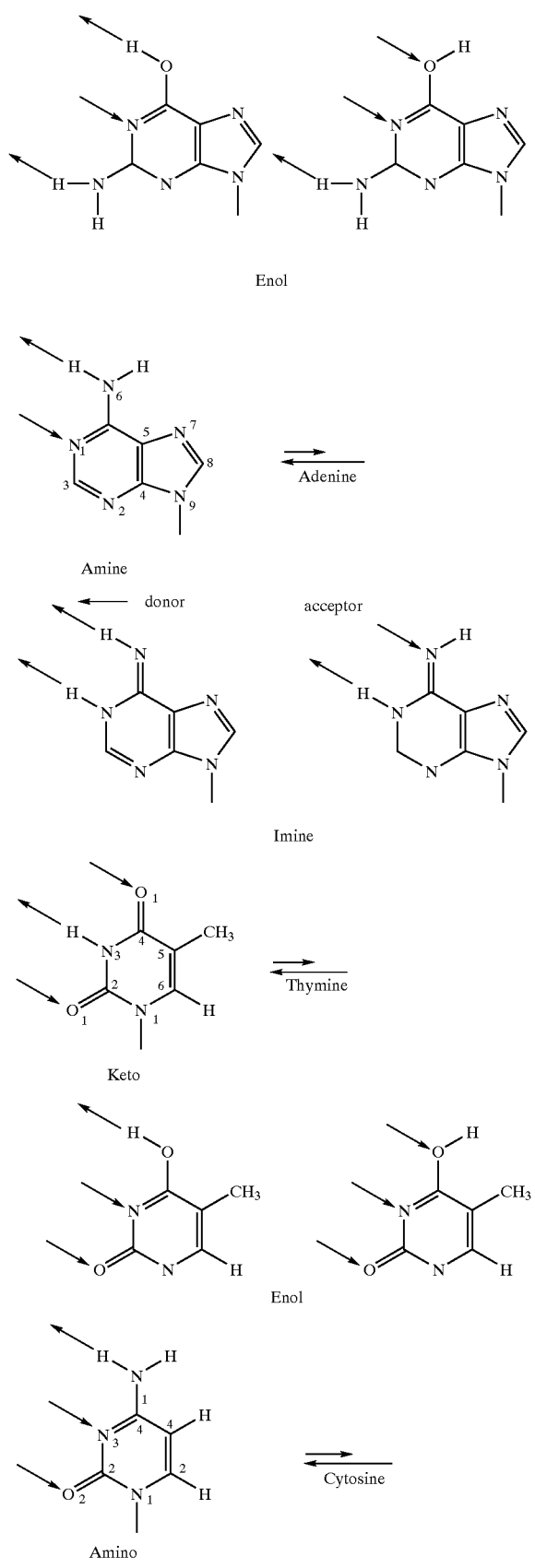

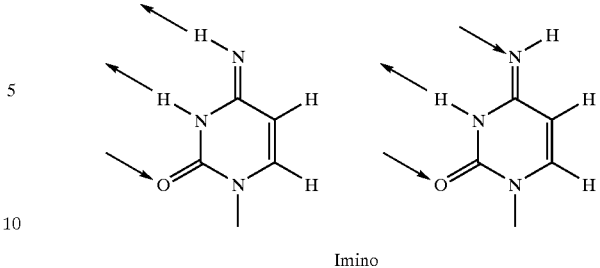

Imino

Finally, the normal bases can be ionized. Thus, A ionizes easily to A(+) at acid pH, C to C(+) also, G to G(−) and T to T(−). Thus, the pairs C-A(+), T(−)-G, C(+)-G and A(+)-G(−) form (scheme 5).

All these possibilities of Watson-Crick pairing and of mismatches described above for nucleotides of "normal" (or conventional) bases (A, T, U, G, C) are also conceivable with those of the nucleotide analogs of the present invention, with variable (higher or lower) probabilities (energy barrier to be overcome) and stabilities (depth of the potential well) of pairing compared to the normal nucleotides, and also diverse qualities of substrates for the enzyme.

The present invention in particular relates to the use of nucleotide analogs which are incorporated by reverse transcriptase into the polynucleotide chain and which pair according to a pairing of the Wobble type. According to the present invention, the expression "pairing of the Wobble type" is intended to denote pairings which break the rule of pairings of the Watson-Crick type as defined above. In pairings of the Wobble type, two bases are linked via hydrogen bonds other than those of the Watson-Crick base pair, thus resulting from different spatial relationships. The glycosidic bond is characteristically in the ANTI configuration. The position of one of the bases relative to its complementary base is shifted (slid) in the horizontal plane of the aromatic rings and of the hydrogen bonds (Saenger, 1984).

The present invention also relates to the use of nucleotide analogs which are incorporated by reverse transcriptase into the polynucleotide chain and which pair according to a pairing of the ANTI-SYN type. According to the present invention, the expression "pairing of the ANTI-SYN type" is intended to denote pairings which break the rule of Watson-Crick pairings.

In ANTI-SYN pairings, the glycosidic bond is characteristically in the ANTI configuration. The ANTI-SYN pair forms between two purines in which one purine is in the ANTI form and the other is in the unconventional SYN form.

Scheme 4

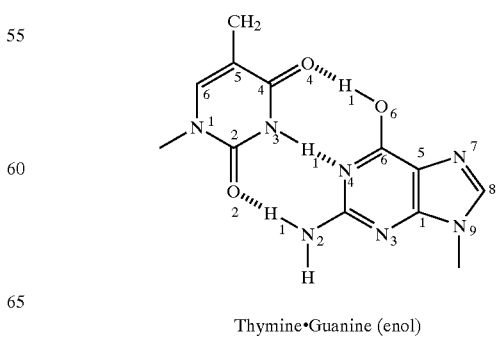

Thymine•Guanine (enol)

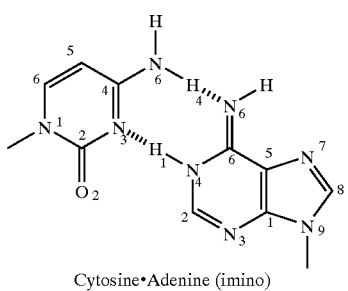

Cytosine•Adenine (imino)

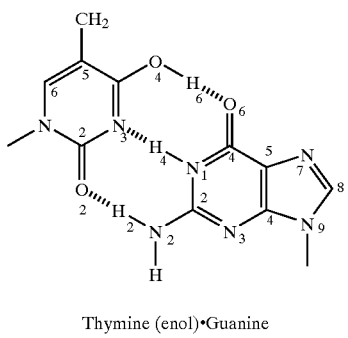

Thymine (enol)•Guanine

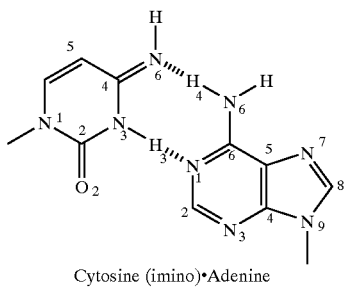

Cytosine (imino)•Adenine

Scheme 5

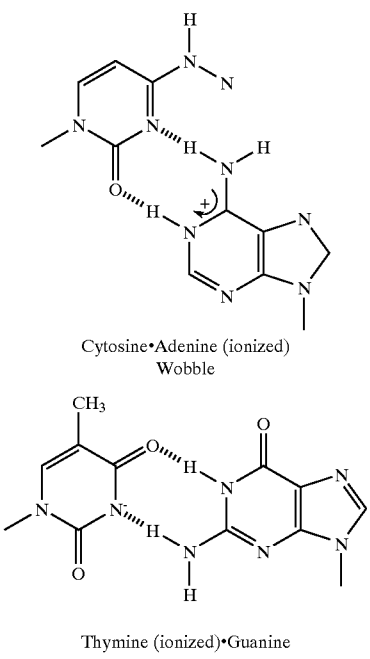

Cytosine•Adenine (ionized)
Wobble

Thymine (ionized)•Guanine

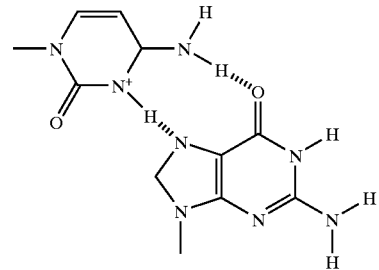

Cytosine (ionized)•Guanine
Hoogsteen

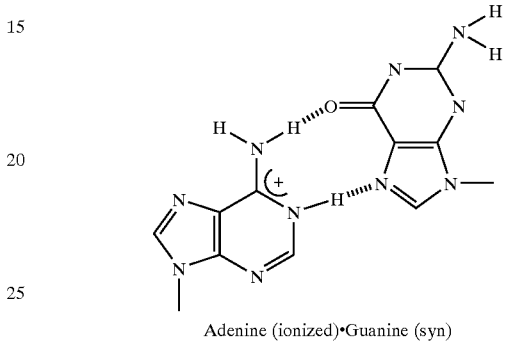

Adenine (ionized)•Guanine (syn)

The present invention also relates to the use of nucleotide analogs which are incorporated by reverse transcriptase into the polynucleotide chain and which pair according to a pairing of the Hoogsteen type and/or of the reverse Hoogsteen type. According to the present invention, the expressions "pairing of the Hoogsteen type" and "pairing of the reverse Hoogsteen type" are intended to denote pairings which break the rule of pairings of the Watson-Crick type. In the Hoogsteen pair, the distance between the $C_1$, and $C_1$, atoms is 8.645 Å; it is therefore decreased by approximately 2 Å compared to the Watson-Crick base pair; the angles between the $C_1, \ldots C^1$, line and the $C_1$, —N glycosyl bonds differ by more than 10° between the purine and pyrimidine bases. In a Hoogsteen base pair, the pyrimidine uses its Watson-Crick surface to pair with the N1, C6, N7 side of the purine base. Finally, a 180° rotation of the pyrimidine results in the formation of a reverse Hoogsteen base pair (Saenger, 1984).

The present invention also relates to the use of nucleotide analogs which are incorporated by reverse transcriptase into the polynucleotide chain and which pair according to a pairing of the reverse Watson-Crick type. According to the present invention, the expression "pairing of the reverse Watson-Crick type" is intended to denote pairings which break the rule of pairings of the Watson-Crick type; reverse Watson-Crick base pairs form when a nucleotide performs a 180° rotation with respect to the complementary nucleotide. In this case, the glycosidic bonds (and the sugar phosphate backbone) are in the trans rather than in the cis orientation. Because of the symmetry in the potential hydrogen bonds of the thymine at the C2-N3-C4 portions, the T base can move around the N3-C6 axis so as to form an A-T base pair according to a reverse Watson-Crick pairing (Saenger, 1984).

A large number of nucleotide analogs can be used in implementing the present invention; these nucleotide analogs are in particular chosen from all natural modified nucleotides, and more particularly from the modified nucleotides present in prokaryotic or eukaryotic RNAs (see table 1), but the present invention is not restricted to only these natural modified nucleotides. A nonexhaustive list of these nucleotides has been published by Limbach et al. (1995) and Motorin and Grosjean (1998). According to the present invention, the nucleotide analogs used are preferably chosen from all the modified nucleotides of prokaryotic or eukaryotic transfer RNAs (tRNAs). Transfer RNAs (tRNAs) contain more than 100 species of modified nucleotides (see table 1), the structures of which have been established. According to another aspect of the present invention, the nucleotide analogs used are chosen from dUTP, dITP, C7dGTP and C7dATP.

TABLE 1

Modified nucleosides present in RNAs

| NAME | SYMBOL |
|---|---|
| Uridine derivatives | |
| Pseudouridine (P) | ψ |
| 2'-O-methylpseudouridine (Z) | ψm |
| 1-methylpseudouridine (I) | $m^1\psi$ |
| 3'-methylpseudouridine | $m^3\psi$ |
| 1-methyl-3-(3-amino-3-carboxypropyl)pseudouridine | $m^1acp^3\psi$ |
| Cytidine derivatives | |
| 2'-O-methylcytidine (B) | Cm |
| $N^4$-methylcytidine | $m^4C$ |
| $N^4,2'$-O-dimethylcytidine | $m^4Cm$ |
| $N^4$-acetylcytidine (M) | $ac^4C$ |
| $N^4$-acetyl-2'-O-methylcytidine | $ac^4Cm$ |
| 5-methylcytidine | $m^5C$ |
| 5-2'-O-dimethylcytidine | $m^5Cm$ |
| 5-hydroxymethylcytidine | $hm^5C$ |
| 5-formylcytidine | $f^5C$ |
| 2'-O-methyl-5-formylcytidine | $f^5Cm$ |
| 3-methylcytidine | $m^3C$ |
| 2-thiocytidine | $s^2C$ |
| lysidine | $k^2C$ |
| 2'-O-methyluridine (J) | Um |
| 2-thiouridine | $s^2U$ |
| 2-thio-2'-O-methyluridine | $s^2Um$ |
| 3-methyluridine | $m^3U$ |
| 3,2'-O-dimethyluridine | $m^3Um$ |
| 3-(3-amino-3-carboxypropyl)uridine (X) | $acp^3U$ |
| 4-thiouridine | $s^4U$ |
| Ribosylthymine (T) | $m^5U$ |
| 5-2'-O-dimethyluridine | $m^5Um$ |
| 5-methyl-2-thiouridine (F) | $m^5s^2U$ |
| 5-hydroxyuridine | $ho^5U$ |
| 5-methoxyuridine | $mo^5U$ |
| uridine-5-oxyacetic acid (V) | $cmo^5U$ |
| uridine-5-oxyacetic acid methyl ester | $mcmo^5U$ |
| 5-carboxymethyluridine | $cm^5U$ |
| 5-methoxycarbonylmethyluridine | $mcm^5U$ |
| 5-methoxycarbonylmethyl-2'-O-methyluridine | $mcm^5Um$ |
| 5-methoxycarbonylmethyl-2-thiouridine | $mcm^5s^2U$ |
| 5-carbamoylmethyluridine | $ncm^5U$ |
| 5-carbamoylmethyl-2'-O-methyluridine | $ncm^5Um$ |
| 5-(carboxyhydoxymethyl)uridine | $chm^5U$ |
| 5-(carboxyhydoxymethyl)uridinemethyl ester | $mchm^5U$ |
| 5-aminomethyl-2-thiouridine | $nm^5s^2U$ |
| 5-methylaminomethyluridine | $mnm^5U$ |
| 5-methylaminomethyl-2-thiouridine (S) | $mnm^5s^2U$ |
| 5-methylaminomethyl-2-selenouridine | $mnm^5se^2U$ |
| 5-carboxymethylaminomethyluridine | $cmnm^5U$ |
| 5-carboxymethylaminomethyl-2'-O-methyluridine | $cmnm^5Um$ |
| 5-carboxymethylaminomethyl-2-thiouridine | $cmnm^5s^2U$ |
| Dihydrouridine (D) | D |
| Dihydroribosylthymine | $m^5D$ |
| Adenosine derivatives | |
| 2'-O-methyladenosine | Am |
| 2-methyladenosine | $m^2A$ |
| $N^6$-methyladenosine | $m^6A$ |
| $N^6,N^6$-dimethyladenosine | $m^6_2A$ |

TABLE 1-continued

Modified nucleosides present in RNAs

| NAME | SYMBOL |
|---|---|
| $N^6,2'$-O-dimethyladenosine | $m^6Am$ |
| $N^6,N^6,2'$-O-trimethyladenosine | $m^6_2Am$ |
| 2-methylthio-$N^6$-methyladenosine | $ms^2m^6A$ |
| $N^6$-isopentenyladenosine | $i^6A$ |
| 2-methylthio-$N^6$-isopentenyladenosine | $ms^2i^6A$ |
| $N^6$-(cis-hydroxyisopentenyl)adenosine | $io^6A$ |
| 2-methylthio-$N^6$-(cis-hydroxyisopentenyl)adenosine | $ms^2io^6A$ |
| $N^6$-glycinylcarbamoyladenosine | $g^6A$ |
| $N^6$-threonylcarbamoyladenosine | $t^6A$ |
| $N^6$-methyl-$N^6$-threonylcarbamoyladenosine | $m^6t^6A$ |
| 2-methylthio-$N^6$-threonylcarbamoyladenosine | $ms^2t^6A$ |
| $N^6$-hydroxynorvalylcarbamoyladenosine | $hn^6A$ |
| 2-methylthio-$N^6$-hydroxynorvalylcarbamoyladenosine | $ms^2hn^6A$ |
| 2'-O-ribosyladenosine (phosphate) | Ar (p) |
| 1-methyladenosine | $m^1A$ |
| Inosine derivatives | |
| inosine (I) | I |
| 2'-O-methylinosine | Im |
| 1-methylinosine (O) | $m^1I$ |
| 1-2'-O-dimethylinosine | $m^1Im$ |
| Guanosine derivatives | |
| 2'-O-methylguanosine | Gm |
| 1-methylguanosine (K) | $m^1G$ |
| $N^2$-methylguanosine (L) | $m^2G$ |
| $N^2,N^2$-dimethylguanosine (R) | $m^2_2G$ |
| $N^2,2'$-O-dimethylguanosine | $m^2Gm$ |
| $N^2,N^2,2'$-O-trimethylguanosine (I) | $m^2_2Gm$ |
| 2'-O-ribosylguanosine (phosphate) | Gr (p) |
| $m^7$-Guanosine derivatives | |
| 7-methylguanosine (7) | $m^7G$ |
| $N^2,7$-dimethylguanosine | $m^{2,7}G$ |
| $N^2,N^2,7'$-trimethylguanosine | $m^{2,2,7}G$ |
| Wyosine derivatives | |
| Wyosine | imG |
| Methylwyosine | mimG |
| Submodified hydroxywybutosine | OhyW |
| Wybutosine (Y) | yW |
| Hydroxywybutosine | OhyW |
| Peroxywybutosine (W) | $o_2yW$ |
| 7-Deazaguanosine derivatives | |
| queuosine (q) | Q |
| Epoxyqueuosine | oQ |
| galactosylqueuosine | galQ |
| mannosylqueuosine | manQ |
| 7-cyano-7-deazaguanosine | $preQ_o$ |
| Archaeosine (other name 7-formamidino-7-deazaguanosine) | gQ ($G^+$) |
| 7-aminomethyl-7-deazaguanosine | $preQ_1$ |

Another aspect of the present invention is the use of nucleotide analogs characterized in that they are not naturally present in living cells; according to the invention, the modified nucleotide analogs obtained via the synthetic pathway preferably contain the modified bases 6H, 8H-3,4-dihydropyrimido[4,5c][1,2]oxazin-7-one (P) and $N^6$-methoxy-2,6-diaminopurine (K) (Hill et al. (1998) Proc. Natl. Acad. Sci. USA 95: 4258–4263).

Preferably, the nucleotide analogs used in the present invention are 2'-deoxyriboses in the triphosphate form and have a hydroxyl (—OH) group on the C3' carbon of the deoxyribose. According to the invention, the nucleotide analogs as defined above may comprise groups which protect the functional groups, in order to preserve the modified bases during their metabolism. The nucleotide analogs may be protected in the form of bis(S-acyl-2-thioethyl)(BIS-SATE) pronucleotides (Benzaria et al., 1996; Lefebvre et al., 1995).

One of the advantages of the present invention is that the natural nucleotide analogs can be obtained easily and in large amount from a culture of microorganisms; such cultures are economical and can be easily produced on a large scale (Gehrke and Kuo, 1985).

The present invention also relates to a pharmaceutical composition, characterized in that it contains nucleotide analogs as defined above and a pharmaceutically acceptable vehicle.

In a particular embodiment of the invention, the pharmaceutical composition of the present invention is characterized in that it contains a mixture of at least one nucleotide analog and of at least one antiretroviral agent chosen from the group composed of nucleotide and non-nucleotide reverse transcriptase inhibitors and viral antiproteases as a combination product for use which is simultaneous, separate or spread out over time in antiviral therapy; the reverse transcriptase inhibitor is preferably chosen from 3'-azido-3'-deoxythymidine (AZT), 2',3'-dideoxyinosine (ddI), 2',3'-dideoxycytidine (ddC), (−)2',3'-dideoxy-3'-thiacytidine (3TC), 2',3'-didehydro-2',3'-dideoxy-thymidine (d4T) and (−)2'-deoxy-5-fluoro-3'-thia-cytidine (FTC), TIBO, HEPT, TSAO, α-APA, nevirapine, BAHP and phosphonoformic acid (PFA); the viral antiprotease is chosen from indinavir and saquinavir.

The possibility of taking control of the genetic characteristics of the reverse transcribed material makes it possible to manipulate the viral progeny in the subsequent replication cycles of the virus. This deferred activity provides a broad scope for maneuver which is left to the initiative of the practitioner, who can choose the nucleotide analogs and the doses in keeping with the particular strategy suited to a particular patient.

This scope does not exist for immediate antiviral agents. For the latter, in fact, either the virus is not able to evade the action of the antiviral agent, and the latter eliminates the virus, or the virus finds a way of counteracting it and the antiviral agent becomes ineffective. The high mutation rate which characterizes reverse transcription greatly favors the latter alternative.

Allowing the reverse transcription to continue avoids two pitfalls which immediate antiviral agents come up against. First, the virus is subjected, by the immediate antiviral agent, to a selection pressure. The low fidelity of its reverse transcriptase allows the virus to rapidly evade this antiviral agent, hence the rapid emergence of resistance mutants. In the case of multitherapies by combining immediate antiviral agents, this emergence is slower but, in most cases, ends up occurring. Then, the antiviral agent or combinations thereof decrease the viral load (often below the detection threshold) for a period of time before the emergence of the resistant viral variety. The latter, freed of competitors, will then be able to invade the organism, often in violent fashion. Conversely, the nucleotide analogs of the invention avoid these two pitfalls. First, the lack of blocking of the reverse transcription removes any selection pressure during the ongoing viral reproduction cycle. The action on the virus, as it happens that resulting from the genetic modification of the material reverse transcribed, programmed on the initiative of the practitioner, is deferred, i.e. for the most part only occurs on the future viral progeny. Then, since the nucleotide analogs according to the invention essentially lack immediate antiviral activity, the overall viral load momentarily remains almost constant. The competition between viral virtual species will be relatively unaffected, which will limit the expression of a particular virtual species.

Characteristics and advantages of the present invention will be more clearly revealed upon reading the following examples.

EXAMPLE 1

Choice of the Sequence

Modrow et al. in 1987 showed that the most common mutations are located in the env gene of the HIV genome, on 5 hypervariable sites (V1 to V5). The great genetic variability in the env gene may be the main reason for the difficulty in producing a vaccine against the viral shell, which makes studying the mechanism of these mutations all the more valuable. The in vitro synthesis, by HIV reverse transcriptase, of the (+) strand (i.e. the strand for which the matrix is the (−) DNA strand derived from the reverse transcription of the viral genome) shows that three-quarters of the mutations at the major pause site (V1 on a series of six As (bases 480 to 485 of the env gene)) are base substitutions (AT→GC and GC→AT), the remainder being frameshifts (Ji et al., 1994).

This work consists in studying the V1 hypervariable region, in its DNA version. With this aim, a sequence of about one hundred bases of the viral env sequence surrounding the six adenines (base 480 to 485 of the env gene) was extended at the two ends with two segments of 17 bases, in which one of the 4 bases is absent for the purpose of being able to initiate the polymerization reaction with only three of the 4 dNTPs.

The natural "primer" sequences of HIV are attached to the two ends of the fragment of the gene, namely to the 3' end of the tRNA sequence (lys3) (sequence complementary to the primer binding site pbs) and to the 5' end of the homopurine sequence (polypurine tract, ppt). This construct is shown in FIG. 1.1.

Thus, the reverse transcription from the pbs primer will use as a matrix the coding strand of the env gene, which will serve as a matrix for the synthesis of the −DNA strand: it will be denoted hereinafter by env−. Similarly, the elongation from the ppt primer will have the −DNA strand as a matrix and will produce the +DNA strand. This matrix will therefore be denoted env+. There was a double reason which prompted us to include pbs and ppt in our construct: mimic the two natural primers and explore the effect of primers for which the purine/pyrimidine composition constraints are notable and probably give rise to conformational and/or thermodynamic particularities.

The study method therefore consists in taking the single-stranded plasmid containing the env− (or env+) sequence, in hybridizing the pbs (or ppt) primer, and in initiating the reverse transcription under the chosen conditions. The elongation on the two complementary strands will show the effect of the two primers and also of the similarities or of the differences on opposite sites.

These matrices were used for parallel studies of HIV-1 reverse transcriptase and of the Klenow fragment of *E.coli* DNA-dependent DNA polymerase (KF). There have been many studies relating to the fidelity and processivity of the Klenow fragment (Abbotts and Wilson, 1988; Lecomte and Ninio, 1987, 1988; Papanicolaou and Ripley, 1989 and 1991).

Studies of reverse transcription termination and fidelity were carried out.

EXAMPLE 2

Identification of Termination Sites

The termination sites and the termination rates at each site were studied in the presence of 4 natural dNTPs present in excess, or in the presence of three of these natural dNTPs, the fourth being replaced with an analog: dUTP as a replacement for dTTP, dITP and c7dGTP as a replacement for dGTP and, finally, c7dATP in place of dATP (FIGS. 1.2 and 1.3). These analogs affect the formation of the hydrogen bonds in the two grooves of the double helix.

The objective was to also evaluate the role of nucleotide analogs on the termination rate of the HIV-1 reverse transcriptase and of the Klenow fragment and to search for the agents responsible for termination of synthesis with the "normal" dNTPs. 4 analogs were selected:

dUTP, analog of dTTP, does not expose $CH_3$ in the major groove as the methyl group in the C5 position of dTTP does. dUTP can pair with A in a conformation of the Watson-Crick type, but also with G in a conformation of the "Wobble" type.

dITP differs from dGTP by the absence of the $NH_2$ group in the C2 position, which leads to the absence of a donor in the minor groove compared to dGTP. The C:I pairing compared to C:G leads to the presence of an acceptor (the oxygen of C) and the absence of a donor ($NH_2$ of I) in the minor groove.

c7dGTP and c7dATP differ, respectively, from dGTP and dATP in that the nitrogen in position 7 is changed for a carbon. This change leads to the disappearance of the N7 acceptor in the major groove, but the pairing of the base pairs of the Watson-Crick type is not modified by this change, unlike the pairing of the Hoogsteen type in which N7 is involved.

These 4 analogs offer a range of pairing modification, pairing geometry and interaction with the water molecules and the protein elements, in the major and minor groove.

The termination sites were identified during polymerization catalyzed by the HIV-1 reverse transcriptase and the Klenow fragment by changing one of the dNTPs for its base analog. dTTP was replaced with dUTP, dGTP was replaced with dITP or c7dGTP and dATP was replaced with c7dATP. In this study, the synthesis is primed with pbs.

The reaction begins by formation of the reaction complex between the matrix/primer labeled at the 5' end (0.05 pmol) with the enzyme (0.01 U/$\mu$l) by incubation at 37° C. for 3 min for the 3 RTs and at 25° C. for the Klenow fragment. A solution containing the 3 dNTPs and one of the analogs, each at the final concentration of 500 $\mu$M, and trapping DNA (100:1:trapping DNA:matrix/cold primer) is then added. The use of trapping DNA makes it possible to prevent the reinitialization of the polymerization at the termination sites. In parallel, a control in the presence of the 4 "normal" dNTPs was carried out under reaction conditions identical to the reaction in the presence of analogs. The mixture is incubated for 30 min at 37° C. for the HIV-1 reverse transcriptase and at 25° C. for the Klenow fragment. The reaction is stopped by adding ⅓ volume of stop solution (v/v), and then the reaction products are loaded onto a denaturing 8 M urea 13% acrylamide gel. Position of the termination sites is identified by the co-migration of the sequencing products (Sanger method).

Each reaction was carried out 3 times; variations in the strength of the termination rates are observed, but they are small and less than 10%. For the HIV-1 reverse transcriptase and the Klenow fragment, the synthesis termination rates with the various analogs (black rods) as a function of the sequence are given in the presence of the termination rates obtained in the control reaction, i.e. in the presence of the "normal" bases (white rods).

2.1. Identification of the termination sites with the HIV-1 reverse transcriptase 2.1.1. Identification of the termination sites in the presence of dUTP (FIG. 2.1)

Very generally, the termination rate with dUTP is lower than with dTTP. Seven sites show a decrease of more than half of their termination rate in the presence of dUTP instead of dTTP, 6 of which have the particularity of succeeding the incorporation of dUMP (i.e. the sites are positioned on an A residue on the matrix: A26, A35, A50, A53, A75 and A77), the seventh stops on a G residue in position 52 which precedes the incorporation of a U. other termination sites located just upstream of an A residue on the matrix also have a tendency to see their failure rate decrease, but less significantly: C49, T76 and G78. Certain sites, not located upstream or on an A residue, see an increase in their strength: G22 and C52.

2.1.2. Identification of the termination sites in the presence of dITP (FIG. 2.2)

In general, the arrest rate is higher with dITP compared to dGTP. Changing dGTP for dITP, one of its analogs, in the reaction catalyzed by the HIV-1 reverse transcriptase (FIG. 2.2), in the reaction medium, leads to a considerable increase (by a factor close to 4) in the termination rates of 10 sites. Of these 10 sites, 5 precede the incorporation of the dITP into the polymerized strand (C20, A24, G27, G32 and A50), 4 are located in the quadruplet just at the exit of the homo-oligomer (dA)6 and the last is located on residue G22. However, other sites see a decrease in their strengths in the presence of dITP, among which the residues G31, A35, A41, G82, C49 and A53; the first three sites do not have a C residue in their close matricial environment, while C49 is a dITP incorporation site and A53 is located upstream of a C residue. Two new sites appear: in front of C25 and C39 of the matrix.

2.1.3. Identification of the termination sites in the presence of c7dGTP (FIG. 2.3)

Of the 18 termination sites obtained in the presence of the "normal" bases, 6 are considerably increased (up to 3.5-fold), others are decreased up to 10-fold and 4 new sites appear. Certain termination sites which are not detectable with dGTP, are revealed with c7dGTP, some of these sites being able to reach considerably high percentages: these sites are located at bases G32, C33, C28 and C29; the first site precedes the incorporation of c7dGTP, whereas the last three sites cited are in the position at which c7dGTP is incorporated into the polymerization strand. The termination rate is increased opposite most of the Cs on the matrix, except for C21 and C49, which show a 10% and 90% decrease, respectively.

Other sites see an increase in their strength, but to a lesser extent: opposite A53 (which precedes the incorporation of the c7dGTP) and G22 and A77, the latter being located at the exit of the series of 6As. Other sites see a decrease in their termination rate, although they are located neither on a site of insertion of c7dGMP or of extension following this insertion.

2.1.4. Identification of the termination sites in the presence of c7dATP (FIG. 2.4)

The termination rates in the presence of c7dATP instead of dATP have contrasting behaviors: some sites, observed with dATP, see a notable increase in their strengths: opposite A41 (×7) and T76 (×2). Others, on the other hand, decrease (opposite bases A50, A53, G52 and A75). The most notable is the appearance of new termination sites facing T39, T62 and especially T63, which stops close to half of the elongation complexes. The greatly increased site (facing A41)

precedes the incorporation of c7dATP. The 3 new sites are consecutive c7dATP incorporation sites, but other consecutive sites do not produce stops (T45 and T46 for example).

2.1.5. Comparison of the termination sites according to the analog used (FIG. 2.5)

The variations in the termination rates of the various analogs compared to the rates obtained in the presence of the "normal" bases are summarized in FIG. 2.5.

Each base analog induces modifications in the termination rates for the polymerization catalyzed by the HIV-1 reverse transcriptase.

Exchanging dTTP for dUTP decreases, in general modestly (maximum 5%), the termination rate of most of the sites located before and after the incorporation of the dUTP. The bases mainly concerned are those downstream of position 50 and the 6As.

dITP induces a large increase in termination, except at 2 sites (at 49 and 82, at which there are slightly fewer stops). All the termination sites are located before the incorporation of the dIMP, i.e. located before a C residue on the matrix, with the exception of A53. The extension of a primer having a dIMP at its 3' end is modified compared to the extension from a dGMP, especially on C49, which shows a very large decrease in the termination rate, and C20, for which the strength increases in the presence of dITP. The other two sites C21 and C51 do not show any significant variation of their termination rate. Surprisingly, termination sites which do not have a C residue in their close matricial environment show variations in the termination rate, in particular at the exit of the series of 6As, where the strength is, on average, doubled.

Exchanging dGTP and dATP for c7dGTP and c7dATP, respectively, leads to an increase in the termination of polymerization using neosynthesized strands having a modified base at their 3' end, with the exception of C21 and C49 in the case of c7dGTP. The sites located before the incorporation of modified bases show an increase in the termination rate in the case of c7dGTP, with the exception of A50. The variation in the termination rates induced by changing dATP for c7dATP is more complex: while, at A41, the termination rate is increased by almost 7-fold in the presence of c7dATP, on A75, it decreases by almost 2-fold and on A35 it remains stable. Some sites which are not located on or before the incorporation of modified bases show a difference in termination rate compared to the "natural" base. Most of these sites see a decrease in their termination rate in the presence of c7dATP instead of dNTP, with the exception of G23 and A77 in the case of c7dGTP. These positions have the particularity of preceding the incorporation of a C residue on the matrix, whereas all the other sites which show a decrease in termination strength precede the incorporation of a pyrimidine or of a T, with the exception of G31. In the case of c7dATP, the first modified base to be incorporated into the polymerized strand is at position T36; upstream of this position, the termination of the polymerization catalyzed by the HIV-1 reverse transcriptase is not modified, whether there is dATP or c7dATP in the reaction medium.

The four analogs studied have contrasting effects on the polymerization:

Exchanging dTTP for dUTP only very slightly modifies the arrest rates, with the general tendency being a decrease, especially at 6As.

Exchanging dGTP for dITP introduces important new stops and, in general, a resulting increase in the termination rates at the start of elongation, around +50 and especially after 6As.

Exchanging dGTP for c7dGTP introduces two important new sites and a considerable increase at the start of elongation, and then a clear tendency toward decreasing the termination rate.

Exchanging dATP for c7dATP has little effect overall, except a considerable increase in front of T(matrix)42 and three new sites, one of which is on the last base of a triplet T(matrix)61–63, where practically half the elongation complexes stop. Termination at the 6As is relatively unaffected. The local accumulation of T seems to lead to an increase in termination.

Although common, stops in front of the sites at which the modified base is requested are not systematic, whether or not this request occurs in an isolated manner.

Overall, the analogs (except dUTP) increase the termination rates from elongation initiation.

2.2. Identification of the termination sites with the Klenow fragment

Overall, the presence of the base analogs reduces the efficiency of the Klenow fragment polymerization, making it difficult to detect termination sites beyond the position +55, and for this reason, we have represented, in the various figures which follow, only the termination sites located between position +20 and +55.

2.2.1. Identification of the termination sites in the presence of dUTP (FIG. 2.6)

Exchanging dTTP for dUTP significantly increases the termination rate of most of the sites which precede the incorporation of the dUMP within the neosynthesized strand, with the exception of G40. Apart from G34, the termination sites in the presence of dUTP are no longer detectable between 31 and 45.

2.2.2. Identification of the termination sites in the presence of dITP (FIG. 2.7)

The increases in the termination rates of the sites located before the incorporation of a dITP (A24, C28, G32, T36 and A50) are generally greater than those at which the dITP has just been incorporated (C29, C33, C51). There is less stopping at C25, C37 and C49: these sites have the particularity of preceding the incorporation of A or T into the polymerized strand, whereas all the other sites precede the incorporation of a G or of a C, with the exception of C29, which has the particularity of being preceded by the incorporation of 2 dIMP.

2.2.3. Identification of the termination sites in the presence of c7dGTP (FIG. 2.8)

All the stops on the sites at which the c7dGMP is incorporated into the polymerized strand are increased compared to the reaction with dGTP, as are (but to a lesser extent) the sites preceding the incorporation of the c7dGMP, with the exception of C32, for which the termination rate decreases by 26% in the presence of c7dGTP. Other sites not located upstream or on c7dGMP insertion sites also show variations in termination rate.

2.2.4. Identification of the termination sites in the presence of c7dATP (FIG. 2.9)

There is an increase in the termination rates in 3 waves, at the start of elongation, after 1 revolution and 3 revolutions of the helix. There is no correlation with the presence of T on the matrix strand. The termination sites between the 3 waves observed with dATP do not give rise to stops with the c7dATP analog.

2.2.5. Comparison of the termination rate according to the analog (FIG. 2.10)

As can be seen on FIG. 2.10, the effects of the 4 analogs are considerable at the start of the elongation and up to approximately +40; the stops increase or decrease in turn. The +50 region is the seat of very significant increases with the 4 analogs.

EXAMPLE 3

Comparison of the Influence of the Presence of the Base Analogs on the Termination of the Synthesis Catalyzed by the two Enzymes 3.1. Recapitulation of the influence of dUTP on termination with the Klenow fragment of DNA polymerase and the HIV-1 reverse transcriptase (FIG. 3.1)

The structural difference between dUTP and dTTP is the absence of a methyl group at position C5 in the pyrimidine base. This group is not involved in base pairing, but it modifies the major groove of the DNA double helix; in addition, base methylation produces a moderate increase in the interaction between the bases.

The HIV-1 reverse transcriptase and the Klenow fragment have different behavior with respect to dUTP. On the A residues of the matrix to be copied, corresponding to the sites at which U has been incorporated, the termination rates decrease for the reverse transcriptase. In the sequence studied and under the conditions of the experiment, the extension of the primer having a U instead of T at its 3' end is therefore, in general, facilitated with the HIV-1 reverse transcriptase, although overall, the variation is modest. During the synthesis catalyzed by the Klenow fragment, there is less variation in the strength of the termination at such sites.

The effect of the matrix base in 3' of A is, in general, to increase the termination rate with dUTP with the Klenow fragment, whereas in the case of the HIV-1 reverse transcriptase, it decreases. The incorporation on the base following that of the U is generally less likely to be terminated (HIV-1 reverse transcriptase) and practically unaffected for the Klenow fragment.

Some terminations which are not contiguous to the incorporation of U are also disturbed by the presence of dUTP instead of dTTP. Thus, the sites located two bases upstream of the U incorporated generally show a variation in the termination rates with the 2 enzymes; this phenomenon is more noticeable in the case of the HIV-1 reverse transcriptase.

Some termination sites not located on or upstream of a site of dUMP insertion, during the polymerization catalyzed with the Klenow fragment, also show variations in their termination rate; the majority of these sites show a decrease in the termination rate in the presence of dUTP, with the exception of the first 3 bases polymerized when no dUMP has been incorporated into the polymerized strand, and of G27.

The effect of incorporating U in place of T is noticeable especially in the elongation corresponding to the first two rotations of the helix (matrix 20 to 40). The complexes with the HIV-1 reverse transcriptase terminate less frequently. The terminations with KF alternate between increase and decrease. The same observations hold for the start of the 4th revolution of the helix, whereas the synthesis of the 3rd revolution of the helix occurs without modification.

It appears that the absence of $CH_3$ in the major groove slightly facilitates the HIV-1 reverse transcriptase elongation.

3.2. Recapitulation of the influence of dITP on the termination with the HIV-1 reverse transcriptase and the Klenow fragment (FIG. 3.2)

The structural difference between dITP and dGTP is the absence of the $NH_2$ group involved in pairing with the C base, producing, inter alia, a decrease in the interaction between the I:C bases compared to the G:C bases.

The termination sites obtained during the synthesis catalyzed by the HIV-1 reverse transcriptase and the Klenow fragment, preceding the incorporation of I, show an increase in their strength, with the exception of A53 for the reverse transcriptase and of G27 for the Klenow fragment. There is also usually an increase in the termination rate on the C sites with the Klenow fragment (with the exception of C25, C37 and C49), whereas, with the HIV-1 reverse transcriptase, the influence of the presence of the dITP is very contrasting: some sites show no significant difference in strength, C21 and C51, whereas the magnitude of C49 is greatly reduced and that of C20 increases dramatically for the polymerization; it cannot be excluded, in the case of C20, that difficulty in incorporating the dITP at C21 is responsible for this increase.

All the C sites on the matrix which show a decrease in the termination rate with the Klenow fragment and with the HIV-1 reverse transcriptase precede the incorporation of an A or a T, whereas the C sites for which the termination rate increases in the presence of dITP instead of dGTP have the particularity of preceding the incorporation of a C or of a G.

The decreased stability of the I.C pair and the absence, for this pair, of a proton acceptor in the minor groove have a marked inhibitory effect on the elongation by the HIV-1 reverse transcriptase during synthesis of the first revolution of the helix. At the exit of the 6As, the HIV-1 reverse transcriptase undergoes strong inhibition.

A surprising fact observed in the case of the HIV-1 reverse transcriptase is the difference in strength observed on certain sites which do not have a C residue in their close environment and which, nevertheless, show, in certain cases, considerable variation in termination. The sequence of the neosynthesized strand of these termination sites up to the 16th base has been represented in table 3.1 for the HIV-1 reverse transcriptase.

For the termination sites not located before or on a dITP insertion site, the termination rate decreases during polymerization with the HIV-1 reverse transcriptase, with the exception of G22, which shows a very large increase in the strength of termination, and A26 and A41, which remain stable. The extraordinary increase in the failure rate at G22 may be explained by the variation in the conformation of the double helix between positions +2 and +5 of the primer strand/matrix which, through exchanging dGTP for dITP, produces a series of A-Is at the level of the matrix/primer A form.

3.3. Recapitulation of the influence of c7dGTP on the termination with the Klenow fragment and with the HIV-1 reverse transcriptase (FIG. 3.3)

The substitution of dGTP with c7dGTP should not substantially modify c7G:C pairing, and its main effect is to delete a proton acceptor in the major groove and therefore suppress the interaction of DNA with the enzyme; however, it causes very significant elongation inhibitions from the synthesis of the 1st revolution of the helix, for the HIV-1 reverse transcriptase.

With the HIV-1 reverse transcriptase and the Klenow fragment, the sites which see an increase in their termination rate are mostly sites located on c7dGTP incorporation sites (with the exception of C21 and C49 with the HIV-1 reverse transcriptase, which are the first two bases polymerized) and the positions which precede the insertion of the c7dGMP in the polymerized strand, with the exception of A50 with the HIV-1 reverse transcriptase and G32 with the Klenow fragment.

Other sites not involved in the incorporation or the extension of the c7dGMP also show variations in their termination rate, in particular at the sites located at the exit of the series of 6As, which, overall, show a decrease in termination in the case of HIV-1 reverse transcriptase.

The sites which show variations in the strength of the termination sites in the presence of the c7dGTP with the HIV-1 reverse transcriptase have been listed in table 3.2. In the case of the HIV-1 reverse transcriptase, with the c7dGTP, only two sites show an increase in the termination rate, G22 and A77, one remains stable, G82, and the others show a decrease. At the level of position 22, only the residues at +2 and +3 are c7dGMPs.

3.4. Recapitulation of the influence of c7dATP on the termination by the HIV-1 reverse transcriptase and by the Klenow fragment (FIG. 3.4)

As with the preceding analog studied, this substitution should not affect c7A.T pairing; however, it considerably disturbs the elongation by the RT, especially during synthesis of the 2nd revolution of the helix, at the start of the 5th and during the 6th, whereas the synthesis of the 1st revolution is affected relatively little.

In the case of the HIV-1 reverse transcriptase, the sites which see an increase in their termination rate are, for the vast majority, sites located on or upstream of T residues on the matrix, implying that the polymerase has difficulties in incorporating the c7dATP into the polymerized strand; once the c7dATP has been incorporated to the matrix, extension is also decreased, with the exception of A75.

The case of the Klenow fragment is particular in that variations in strength of termination are observed during polymerization of the first bases, although no c7dAMP has been incorporated. These variations are also present in the presence of only 3 of the 4 dNTPs (C,G,T) (data not shown).

As in the cases with dITP and c7dGTP, we have listed, for the HIV reverse transcriptase, in table 3.3, the sites which show differences in their termination rate with the dATP and c7dATP, although they are located neither on a position of incorporation nor of extension of the analog.

With the HIV-1 reverse transcriptase, variations in the strength of termination are observed on sites not involved in the extension or in the incorporation of c7dATP; these variations are probably due to the difference in the sequence of the neosynthesized strand containing c7dAMPs instead of dAMPs (see table 3.3) which would modify the interaction of the RTs with the reaction complex and therefore would either increase or decrease the frequency of dissociation.

3.5. Recapitulation of the influence of the base analogs on termination

Each base analog induces modifications in the polymerization catalyzed by the HIV-1 reverse transcriptase and the Klenow fragment. An interesting fact in this chapter is the influence of these analogs on sites not involved in the incorporation or extension of a modified base, with the exception of U. Now, all these sites which show a variation in their termination rate have the particularity of being preceded by the incorporation of modified bases on the polymerized strand, with the exception of the Klenow fragment with c7dATP. The variations in the termination rates at the level of the first bases polymerized in the presence of c7dATP may be explained by the 3'→5' exonuclease activity of KF.

EXAMPLE 4

Study of the Fidelity of the HIV-1 Reverse Transcriptase in the Presence of the Base Analogs In order to understand the role of the three dNTPs present involved in the misincorporation subsequent to the absence of the fourth dNTP, dGTP and/or dCTP were replaced with dITP and dUTP, respectively, in the reaction minus A. dITP was chosen because I can pair with T and therefore compensate for the absence of A, and dUTP was chosen in order to assess the affect that the absence of the methyl of a T may have on the fidelity of incorporation of the neighboring pair. For this reason, we are interested not only in the sites and rates of misincorporations, but in the kinetics with which these misincorporations take place. The conditions most suited to the lack of fidelity of the HIV-RT were selected: use of the matrix+env (ppt primer) and absence of dATP (data not shown).

After hybridization of the ppt primer labeled at the 5' end (1 pmol), with the matrix+env (2 pmol), the HIV-1 reverse transcriptase is added at the final concentration of 0.1 U/$\mu$l. Solutions containing dCTP, dGTP, dTTP (control), dCTP, dITP, dTTP or dCTP, dGTP, dUTP or dCTP, dITP, dUTP, each at the final concentration of 500 $\mu$M, were added to equivalent (¼ of the mixture) fractions. Aliquots of ¼ of the reaction volume are taken after 1 min, 2.5 min, 5 min and 10 min, and the reaction is stopped with 1 mN EDTA (final concentration). After denaturation at 92° C. for 5 min, the reaction products are loaded onto an 8M urea denaturing 13% acrylamide gel.

Under the conditions of the experiment (enzyme concentration 0.1 U/$\mu$l), in the absence of dATP but in the presence of the other 3 normal dNTPs, the major pauses are located upstream of the T residues on the matrix (FIG. 4.1), but not all these sites have identical stop capacities. At the level of the second misincorporation, the enzyme pauses very infrequently both upstream of T-130 (matrix) and on T-130, whereas, at T-135 and T-125 (matrix), the enzyme pauses mainly upstream of the bases and infrequently on the incorrectly paired end.

When replacing dTTP with dUTP, the profile of the pauses is relatively unchanged (FIG. 4.2), although an increase in the termination rate can be seen compared to the reaction with dTTP.

When replacing dGTP with dITP, the pause in front of T-135 (matrix) is no longer detectable, whereas a pause appears opposite A-134 (FIG. 4.3), this occurring even though dTTP is present. The termination in front of T-130 (matrix) greatly decreases in strength.

The simultaneous changing of dTTP and dGTP for dUTP and dITP does not significantly modify the profiles of the pauses compared to the reaction with dITP, but increases the strength of the pauses.

FIG. 4.4 represents the variation in the misincorporation rate in front of T-135 (matrix), the first misincorporation site, as a function of time and of the base analog used.

In the presence of dCTP, dGTP and dTTP, the error rate at the first misincorporation site opposite T-135 increases from 33% to 78% after 10 min of incubation; this percentage then remains constant (80% error after 30 min). Exchanging dTTP for dUTP causes a shift in the curve, the error rate climbs from 5% to 65% after 10 min of incubation (after 45 min, this percentage tends towards 77%, experiments not shown).

Replacing dGTP with dITP, or dGTP and dTTP with dITP and dUTP, induces a respective increase in the error rates of 0 to 40 and of 0 to 20%, after 10 min of elongation; similar values are also observed after 45 min (data not shown). There appear, therefore, to be two effects: a kinetic effect, linked to the slowed incorporation of the dITP analog, and a decreased error rate in the presence of this base. This is explained by the substitution of dITP for the absent dATP.

EXAMPLE 5

Analysis of Mismatches

In order to more fully understand the mechanisms which direct the incorporation of incorrect nucleotides inserted during "minus" reactions, several "mutants" obtained with the HIV-1 reverse transcriptase were sequenced. The study was limited to the case of "minus A", since the mutated sequences are easily identifiable by restriction.

5.1. In the presence of the "natural" bases

The various mutants are generated during the "minus A" reaction with the matrix+ env and the ppt primer.

Matrix/labeled primer (0.5 pmol), reverse transcriptase (0.04 U/μl) and the 3 dNTPs (500 μM final) were incubated for 30 min at 37° C., and then the dATP (500 μM final) was added and the incubation continued for 30 min at 37° C. The reaction is then stopped by adding EDTA at the concentration of 10 mM final. The reaction products are recovered after alcohol precipitation and digested with the Sac I enzyme. After denaturation at 90° C. for 3 min, the product is loaded onto a denaturing 10% acrylamide gel. After migration and auto-radiography, the 200-base bands are recovered on the gel and then purified. These fragments are amplified by PCR (15 cycles), cleaved with Mlu I and Bam H I and inserted into pBluescript SK+ppt by ligation with T4 DNA ligase, followed by transformation with XL-1 Blue.

The mutated plasmids are easily selected since they no longer have the restriction site recognized by the Nco I enzyme (see FIG. 4.5). In addition, the absence of enzymatic digestion with Sph I implies a double mutation.

With the HIV-1 reverse transcriptase, of the 48 plasmids isolated and analyzed on agarose gel with the Nco I and Sph I restriction enzymes, 33 plasmids have been mutated at at least two sites since none is digested with either Nco I or Sph I. No plasmid containing only one mutation was isolated.

In order to determine the types of mutation induced by the absence of dATP in the reaction medium during the polymerization catalyzed by the HIV-1 reverse transcriptase, some plasmids were sequenced. The mutated sequences are represented in FIG. 4.6. Only part of the sequence studied has been represented, the remainder of the sequence shows no mutation.

It is noted that, under the conditions of our study, and for the sequences analyzed, the errors forced due to the absence of dATP in the medium produce neither deletions nor insertions, but only base substitutions.

When the first misincorporation occurs, G is incorporated exclusively in place of A on the 10 plasmids mutated with the HIV-1 reverse transcriptase, whereas, for the other positions, although G preferentially replaces A, pyrimidines are also present, in particular C.

It is noted that the first and second misincorporation takes place within an identical close matricial context (3' GTAC5') but can generate different substitutions. This implies that the type of error engendered by the HIV-1 reverse transcriptase would be affected by sequence differences distant from the site of mutation. The engendered error T.dGTP cannot be explained by a frameshift of the primer or of the matrix; thus, this error is probably engendered by the direct incorporation of the incorrect nucleotide. On the other hand, the error T.dCTP on the second site may be explained by such a frameshift over more than one base.

5.2. Study in the presence of base analogs

The polymerization reaction was carried out in the absence of dATP, as for the reaction in the presence of the "natural" bases, but the dGTP was replaced with dITP or the dTTP was replaced by dUTP. After 30 min at 37° C. in the presence of the HIV-1 reverse transcriptase and of 3 of the 4 bases, the matrix/labeled primer is purified on a Sephadex G50 column, so as to eliminate the nucleotides which have not been incorporated, and in particular the dITP and dUTP which would modify the Sac I restriction site. The elongation is then continued for 30 min at 37° C. in the presence of the 4 natural dNTPs, at the final concentration of 500 μM, and of the enzyme (0.05 U/μl). After alcohol precipitation, digestion with the Sac I restriction enzyme and recovery of the 200-base band, a PCR is carried out under the same conditions as for the reaction in the presence of the "natural" bases.

5.2.1. Study of misincorporation by the HIV-1 reverse transcriptase in the presence of dITP Of the 36 plasmids isolated, 4 are mutated at least on the first site at which A is requested, one on the first two sites and 3 on at least the first three sites, according to the enzymatic digestion test with Nco I and Sph I. The mutated sequences are represented in FIG. 4.7.

No deletion or insertion is detected by the enzymatic test in the 7 plasmids sequenced.

At the 1st site of misincorporation (T-135 matrix), the I base, which is an analog of G, is incorporated 3 times and C is incorporated 4 times. At the second site (T-130 matrix), C is the only base found, and at the third (T-125 matrix) T and C are detected.

5.2.2. Study of misincorporation by the HIV-1 reverse transcriptase in the presence of dUTP The experimental protocol is identical, except that the dTTP was replaced with dUTP.

Of the 36 mutated plasmids, 21 plasmids have at least two mutations (determine by enzymatic digestion with Sph I and Nco I), and the other 15 plasmids are linearized both with the Sph I enzyme and the Nco I enzyme and do not have any mutations on these sites. FIG. 4.8 gives the sequence of the 6 plasmids sequenced.

Of the 6 plasmids sequenced, one has 3 mutations, whereas, for the other 5, the HIV-1 reverse transcriptase has incorporated up to 4 incorrect nucleotides on the same strand. All the mismatches on the first site are Gs, those on the subsequent sites are mainly Gs as well, with Cs but never Us. The mismatches are of the T:G type, but mismatches of the T:C type are also present, though with a lower frequency of appearance (17 against 6 taking into consideration all mismatches whatever their position). However, not all the sites at which the incorporation of incorrect nucleotides has taken place are equal with respect to the type of mismatch engendered by the HIV-1 reverse transcriptase: at the 1st misincorporation, of the 6 plasmids mutated, T:G is the only mismatch observed, whereas, at the 2nd misincorporation, T:C is as frequent as T:G. On the 3rd and 4th site of misincorporation, G is preferentially introduced compared to the base C, with, respectively, 4 T:G against 2 T:C and 4 T:G against 1 T:C. No base U is incorporated to form the mismatch T:U.

5.2.3. Conclusion

In the study of the mutants obtained in the "minus A" reaction in the presence of the natural substrates of the HIV-1 reverse transcriptase, the errors engendered are substitutions of the transition type, the purine A being preferentially substituted with the purine G when dGTP is present in the reaction medium.

It is recalled that G can pair with T as a "Wobble" pairing.

The G.T pairing, represented in FIG. 4.9, does not have a geometry of the Watson-Crick type (Hunter and Kennard, 1987). The G.T base pair induces only very few local disturbances of the helix and the overall conformation of the duplex is relatively unaffected. The GT pair gives rise to complex hydration structures (see FIG. 4.9) which make it possible to stabilize the pairing and to insert this pair in the double helix. The predominance of the G substitution can therefore easily be explained by the stability of the GT base pair.

The heteropyrimidine pair T:C has been described in two configurations which are symmetrical only, the T:T pair has been described in the symmetrical and asymmetrical configuration (Donohue and Trueblood, 1960). Only in the latter configuration are the positions of the glycosyl linkages of the T:T pair compatible with its insertion into the double helix. The same observation holds for one of the T:C pairs. The energies of interaction between these bases are in the order T:G>>T:C>T:T (Kudritskaya and Danilov, 1976), namely the order of preference of incorporation opposite T (matrix) which we observe.

At the first mutation site, the substitution with G is systematic. It is preferred on the other sites. The first two mutation sites have the same local sequence. One possibility for explaining the presence of the C at the second site but not at the first site may be found in the frameshift of the neosynthesized strand, facilitated by the misincorporation at the first site (FIG. 4.10). However, at the other three mutation sites, the substitution with G cannot be explained by such a frameshift.

In the presence of dGTP, dCTP and dTTP, the order of preference of substitution at the four sites is G>>C>>T during the polymerization catalyzed by the HIV-1 reverse transcriptase in the absence of dATP.

The analysis of the mutated plasmids is limited to the first four Ts (matrix) encountered by the enzymes. In the case of the HIV-1 reverse transcriptase, extensions well beyond this are observed on the autoradiography gel. In order to verify whether the elongations stopped are definitively terminated or are pausing while remaining active, we repeated the "minus A" experiment, but, instead of stopping the reaction after 30 min at 37° C., the missing dATP is added to the reaction mixture, at the final concentration of 500 μM, and the reaction is stopped 30 min later with ⅓ (v/v) of stop solution. Under these conditions, on all the strands stopped at a given position, the elongation resumes. The complexes stopped are therefore still active.

The absence of modification of the profiles of misincorporation when replacing the dTTP with dUTP was predictable, since we observed, in the absence of the dATP, a single incorporation of a T opposite a T (matrix). The asymmetric T:T pair has been described (Donohue and Trueblood, 1960), but appears to be relatively unstable (Kudritskaya and Danilov V. I., 1976). dITP decreases the error rate observed with dGTP at the first misinsertion site by almost 50% after 45 min of incubation. Misincorporation in the presence of dITP will therefore be more difficult than in the presence of dGTP. In the absence of dATP and dGTP, the purine I pairs with T in only three cases, against eight T:C pairings and one T:T pairing. The three T:Is appear, moreover, opposite the first T-135 (matrix). We did not find any reference concerning the energy of the T:I pair, but the insertion rates which we observe are in favor of the classification T:C>>T:I>>T:T.

The study of the fidelity of the HIV-1 reverse transcriptase, carried out in the absence of one of the 3 nucleotides, showed that the error rate of the elongation using ppt is greater compared to the polymerization using pbs. The study, in agreement with those by Perrino et al., 1989, and Yu and Goodman, 1992, shows that the reverse transcriptase extends the mismatches more easily than it forms them. The absence of a band of strong termination at the sites of misincorporation beyond the 1st mismatch suggests that the incorrectly paired base pairs only slightly affect the continuation of the polymerization with the HIV-1 reverse transcriptase. In certain cases, in particular with the ppt primer, the mismatches in the neosynthesized strand even appeared to promote the subsequent errors.

The study of the mutants obtained in the absence of dATP during the polymerization catalyzed by the HIV-1 reverse transcriptase indicates that the types of error induced by this reverse transcriptase do not show any base dilutions or additions. Overall, the order of substitution at the four T sites of the matrix is G>>C>>T. It is possible that the mismatch at the 1st site modifies the specificity of the error on the subsequent sites, either by promoting the displacement of the primer strand (FIG. 4.10), by promoting dislocation or by modifying the conformation of the catalytical site.

At the 1st misincorporation site, G is probably paired with T in a pairing of the "Wobble" type. T.G pairing of the "Wobble" type (FIG. 4.9) is stabilized by hydrogen-type bonds with the 3 water molecules. The absence of $NH_2$ from I destabilizes this pairing, which would explain the decrease in the substitution T:I compared to T:G.

The fidelity of the HIV-1 reverse transcriptase, in the absence of dATP, in the presence of dITP instead of dGTP, is increased. The majority of the mutants identified in the presence of dITP show only one mutation in addition the order of substitution, which is modified compared to the reaction with dGTP, is C>>I>>T. Changing T for U only slightly modifies the profile and the specificity of the mutations engendered by the HIV-1 reverse transcriptase.

EXAMPLE 6

General Conclusion

The processivity and fidelity of the HIV-1 reverse transcriptase can be modulated using modified bases.

The presence of modified bases in the reaction mixture modifies the processivity at the positions which are located on the sites of incorporation of the modified bases and which precede the latter, possibly involving an effect of consecutive base stacking on the termination of the polymerization, as we have shown in the case of the natural bases (unpublished results). In the case of the use of analogues such as dITP and c7dNTP, we have shown variations in the processivity at sites not involved in the incorporation of these modified bases; these variations may be explained by modifications of the conformation of the DNA double helix involving the twenty-or-so bases which is in contact with the enzyme. This modification of the double helix conformation is induced by the structural differences which exist between the natural bases and their analogs, which produce changes in the interaction between the paired bases and the protein elements in the major and minor groove, in the symmetry of pairing, in the steric effects, in the ionic forces, etc. The DNA double helix attached to HIV-1 RT has a characteristic conformation: an A form over the 5 base pairs close to the catalytic site, followed by a bend of approximately 40° and a B form in contact with the connection domain (Ding et al., 1997). The modification of the conformation of the double helix in contact with HIV-1 RT induced by the presence of modified bases in the neosynthesized strand complemented by the matrix strand will destabilize or stabilize the reaction complex and, respectively, decrease or increase processivity.

The presence of modified bases may modify the fidelity of the HIV-1 reverse transcriptase. We have shown, in vitro, that, in the absence of dATP, replacing dGTP with one of its analogues, dITP, decreases the mutation rate, decreases the number of mismatches per plasmid and increases the heterogenicity of the mutated plasmids. The decrease in the mutation rate can be explained by the absence of NH2 from I, which destabilizes the T.I pairing compared to T.G, which is stabilized by hydrogen-type bonds with 3 water molecules (FIG. 4.9). The use of base analogues thus makes it possible to modify the mismatch order of preference.

Hereinafter, reference will be made to the following figures:

FIG. 1.1: Sequence used in this study. The primers are underlined. The pbs primer is followed by 16 bases lacking A.

FIG. 1.2: Chemical structure of dTTP and dUTP.

FIG. 1.3: Chemical structure of dGTP and of two of its analogs, dITP and c7dGTP.

FIG. 1.4: Chemical structure of dATP and of one of its analogs, c7dATP.

FIG. 2.1: Termination rate for the polymerization catalyzed with the HIV-1 reverse transcriptase, as a function of the sequence to be copied. The x-axis represents the nucleotide sequence of -env (sense strand) from the 3' to the 5' end, which is used as a matrix for the pbs primer during polymerization. (□) in the presence of dATP, dCTP, dGTP and dTTP, (□) in the presence of dATP, dCTP, dGTP and dUTP, each at the final concentration of 500 µM.

FIG. 2.2: Termination rate for the polymerization catalyzed with the HIV-1 reverse transcriptase, as a function of the sequence to be copied. The x-axis represents the nucleotide sequence of -env (sense strand) from the 3' to the 5' end, which is used as a matrix for the pbs primer during polymerization. (□) in the presence of dATP, dCTP, dGTP and dTTP, (□) in the presence of dATP, dCTP, dITP and dTTP, each at the final concentration of 500 µM.

FIG. 2.3: Termination rate for the polymerization catalyzed with the HIV-1 reverse transcriptase, as a function of the sequence to be copied. The x-axis represents the nucleotide sequence of -env (sense strand) from the 3' to the 5' end, which is used as a matrix for the pbs primer during polymerization. (□) in the presence of dATP, dCTP, dGTP and dTTP, (□) in the presence of dATP, dCTP, c7dGTP and dTTP, each at the final concentration of 500 µM.

FIG. 2.4: Termination rate for the polymerization catalyzed with the HIV-1 reverse transcriptase, as a function of the sequence to be copied. The x-axis represents the nucleotide sequence of –env (sense strand) from the 3' to the 5' end, which is used as a matrix for the pbs primer during polymerization. (□) in the presence of dATP, dCTP, dGTP and dTTP, (□) in the presence of c7dATP, dCTP, dGTP and dTTP, each at the final concentration of 500 µM.

FIG. 2.5: Variation in the termination rate with the HIV-1 reverse transcriptase with the various analogs. The x-axis represents the nucleotide sequence of the sense strand from the 3' to the 5' end. The variation in the termination rate was calculated by subtracting the termination rate obtained from the reaction carried out in the presence of a base analog (dUTP:blue; dITP:red; c7dGTP:green; c7dATP:black) from the rates obtained with the normal base at each site.

FIG. 2.6: Termination rate for the polymerization catalyzed with the Klenow fragment as a function of the sequence to be copied. The x-axis represents the nucleotide sequence -env (sense strand) from the 3' to the 5' end, which is used as a matrix for synthesis using the pbs primer. (□) in the presence of dATP, dCTP, dGTP and dTTP, (□) in the presence of dATP, dCTP, dGTP and dUTP, each at the final concentration of 500 µM.

FIG. 2.7: Termination rate for the polymerization catalyzed with the Klenow fragment as a function of the sequence to be copied. The x-axis represents the nucleotide sequence -env (sense strand) from the 3' to the 5' end, which is used as a matrix for synthesis using the pbs primer. (□) in the presence of dATP, dCTP, dGTP and dTTP, (□) in the presence of dATP, dCTP, dITP and dTTP, each at the final concentration of 500 µM.

FIG. 2.8: Termination rate for the polymerization catalyzed with the Klenow fragment as a function of the sequence to be copied. The x-axis represents the nucleotide sequence -env (sense strand) from the 3' to the 5' end, which is used as a matrix for synthesis 35 using the pbs primer. (□) in the presence of dATP, dCTP, dGTP and dTTP, (□) in the presence of dATP, dCTP, c7dGTP and dTTP, each at the final concentration of 500 µM.

FIG. 2.9: Termination rate for the polymerization catalyzed with the Klenow fragment as a function of the sequence to be copied. The x-axis represents the nucleotide sequence –env (sense strand) from the 3' to the 5' end, which is used as a matrix for synthesis using the pbs primer. (□) in the presence of dATP, dCTP, dGTP and dTTP, (□) in the presence of c7dATP, dCTP, dGTP and dTTP, each at the final concentration of 500 µM.

FIG. 2.10: Variation in the transcription rate with the Klenow fragment with the various analogs. The x-axis represents the nucleotide sequence of the sense strand from the 3' to the 5' end. The variation in termination rate was calculated by subtracting the termination rate obtained from the reaction carried out in the presence of a base analog (dUTP:blue; dITP:red; c7dGTP:green; c7dATP:black) from the rates obtained with the normal base at each site.

FIG. 3.1: Variation in the termination rate with the HIV-1 reverse transcriptase, for the Moloney murine leukemia virus (MoMLV) reverse transcriptase, for the avian myeloblastoma virus (AMV) reverse transcriptase and for the Klenow fragment, in the presence of dUTP instead of dTTP. The x-axis represents the nucleotide sequence of the sense strand from the 3' to the 5' end. The variation in the termination rate is calculated by subtracting the termination rate obtained from the reaction carried out in the presence of dUTP from the rates obtained with dTTP at each site for each of the enzymes (HIV-1 RT:blue; MoMLV RT:red; AMV RT:green; Klenow fragment:black).

FIG. 3.2: Variation in the termination rate with the HIV-1 reverse transcriptase, for the Moloney murine leukemia virus (MoMLV) reverse transcriptase, for the avian myeloblastoma virus (AMV) reverse transcriptase and for the Klenow fragment, in the presence of dITP instead of dGTP. The x-axis represents the nucleotide sequence of the sense strand from the 3' to the 5' end. The variation in the termination rate is calculated by subtracting the termination rate obtained from the reaction carried out in the presence of dITP from the rates obtained with dGTP at each site for each of the enzymes (HIV-1 RT:blue; MoMLV RT:red; AMV RT:green; Klenow fragment:black).

FIG. 3.3: Variation in the termination rate with the HIV-1 reverse transcriptase, for the Moloney murine leukemia virus (MoMLV) reverse transcriptase, for the avian myeloblastoma virus (AMV) reverse transcriptase and for the Klenow fragment, in the presence of c7dGTP instead of dGTP. The x-axis represents the nucleotide sequence of the sense strand from the 3' to the 5' end. The variation in the termination rate is calculated by subtracting the termination rate obtained from the reaction carried out in the presence of c7dGTP from the rates obtained with dGTP at each site for each of the enzymes (HIV-1 RT:blue; MoMLV RT:red; AMV RT:green; Klenow fragment:black).

FIG. 3.4: Variation in the termination rate with the HIV-1 reverse transcriptase, for the Moloney murine leukemia virus (MoMLV) reverse transcriptase, for the avian myeloblastoma virus (AMV) reverse transcriptase and for the Klenow fragment, in the presence of c7dATP instead of dATP. The x-axis represents the nucleotide sequence of the sense strand from the 3' to the 5' end. The variation in the termination rate is calculated by subtracting the termination rate obtained from the reaction carried out in the presence of c7dATP from the rates obtained with dATP at each site for each of the enzymes (HIV-1 RT:blue; MoMLV RT:red; AMV RT:green; Klenow fragment:black).

Table 3.1: Influence of the presence of dIMP compared to dGMP in the sequence of the neosynthesized strand on the variation in the termination rate during the reaction catalyzed by the HIV-1 reverse transcriptase. Reference 1 is the polymerization termination site under consideration.

Table 3.2: Influence of the presence of c7dGMP compared to dGMP in the sequence of the neosynthesized strand on the variation in the termination rate during the reaction catalyzed by the HIV-1 reverse transcriptase. Reference 1 is the polymerization termination site under consideration.

Table 3.3: Influence of the presence of c7dAMP compared to dAMP in the sequence of the neosynthesized strand on the variation in the termination rate during the reaction catalyzed by the HIV-1 reverse transcriptase. Reference 1 is the polymerization termination site under consideration.

FIG. 4.1: Kinetics of arrest of polymerization catalyzed by the HIV-1 reverse transcriptase in the presence of dCTP, dGTP and dTTP, each at the final concentration of 500 $\mu$M; (□) 1 min, (□) 2.5 min, (□) 5 min, (□) 10 min.

FIG. 4.2: Kinetics of arrest of polymerization catalyzed by the HIV-1 reverse transcriptase in the presence of dCTP, dGTP and dUTP, each at the final concentration of 500 $\mu$M; (□) 1 min, (□) 2.5 min, (□) 5 min, (□) 10 min.

FIG. 4.3: Kinetics of arrest of polymerization catalyzed by the HIV-1 reverse transcriptase in the presence of dCTP, dITP and dTTP, each at the final concentration of 500 $\mu$M; (□) 1 min, (□) 2.5 min, (□) 5 min, (□) 10 min.

FIG. 4.4: Error rate for the HIV-1 reverse transcriptase, at the first site of misincorporation opposite T-135 (matrix+ env) as a function of time; dCTP, dGTP, dTTP, (♦), dCTP, dGTP, dUTP (■), dCTP, dITP, dTTP (Δ), dCTP, dITP, dUTP (X), each at the final concentration of 500 $\mu$M.

FIG. 4.5: Identification, by enzymatic digestion with NcoI and SphI, of the plasmids mutated when polymerization is carried out with +env as the matrix and primed with ppt, in the absence of ATP.

FIG. 4.6: Mutants obtained during polymerization using the +env matrix, primed with ppt, in the absence of dATP and in the presence of dCTP, dGTP and dTTP. Study carried out with the HIV-1 reverse transcriptase and the avian myeloblastoma virus (AMV) reverse transcriptase.

FIG. 4.7: Mutants obtained during polymerization using the+ env matrix, primed with ppt, in the absence of dATP and in the presence of dCTP, dITP and dTTP. Study carried out with the HIV-1 reverse transcriptase and the avian myeloblastoma virus (AMV) reverse transcriptase.

FIG. 4.8: Mutants obtained during polymerization using the +env matrix, primed with ppt, in the absence of dATP and in the presence of dCTP, dGTP and dUTP. Study carried out with the HIV-1 reverse transcriptase and the avian myeloblastoma virus (AMV) reverse transcriptase.

FIG. 4.9: Structure of the Guanine (G)—Thymine (T) mismatch of the "WOBBLE" type. The thymine is projected into the major groove, whereas the guanine is projected into the minor groove of the DNA. The 3 water molecules, which stabilize the incorrectly paired base pair using available hydrogen-type bonds, are represented.

FIG. 4.10: Possible intermediate producing the substitution T to C at the second site of misincorporation. The noncomplementary bases are in bold.

REFERENCES

Abbotts, J., Sen Gupta, D. N., Zon, G. & Wilson, S. H. (1988). Studies on the mechanism of *Escherichia coli* DNA polymerase I Large Fragment. *J. Biol. Chem.* 263: 15094–15103.

Alkhatib, G., Combadiere, C., Broder, C. C., Feng, Y., Kennedy, P. E., Murphy, P. M. & Berger, E. A. (1996). CC CKR5: a RANTES, MIP-1α, MIP-1β receptor as a fusion cofactor for macrophage tropic HIV-1. *Science.* 272: 1955–1958.

Benzaria, S., Pelicano, H., Johnson, R., Maury, G., Imbach, J. L., Aubertin, A. M., Obert, G., Gosselin, G. (1996). Synthesis, in vitro antiviral evaluation, and stability studies of bis(S-acyl-2-thioethyl) ester derivatives of 9-[2-phosphonomethoxy)ethyl]adenine (PMEA) as potential PMEA prodrugs with improved oral bioavailability. *J. Med. Chem.* 39: 4958–4965.

Choe, H., Farzan, M., Sun, Y., Sullivan, N., Rollins, B., Ponath, P. D., Wu, L., Mackay, C. R., La Rosa, G., Newman, W., Gerard, N., Gerard, C. & Sodroski, J. (1996) The beta-chemokine receptors CCR3 and CCR5 facilitate infection by primary HIV-1 isolates. *Cell.* 85: 1135–1148.

Debyser and De Clercq (1996) J. Immunol. Immunopharmacol. 16: 48–52.

De Clercq (1997) Int. J. Antimicrob. Agents 9: 21–36.

De Clercq and Balzarini (1995) II Farmaco, 50: 735–747.

Deng, H., Liu, R., Ellmerer, W., Choe, S., Unutmaz, D., Burckhard, M., Di Marzio, P., Marmon, S., Sutton, R. E., Hill, C. M., Davis, C. B., Peiper, S. C., Schall, T. J., Littaman, D. R. & Landau, N. R. (1996). Identification of a major co-receptor for primary isolates of HIV-1. *Nature.* 381: 661–666.

Di Marco Veronese, F., Copeland, T. D., Devico, A. L., Rahman, R., Oroszlan, S., Gallo, R. C. & Sarngadharan, M. G. (1986). Characterization of highly immunogenic p66/p51 as the reverse transcriptase of HTLV-III/LAV. *Science.* 231 1289–1291.

Domingo, E., Martinez-Salas, E., Sobrino, F., de la Torre, J. C., Portela, A., Ortin, J., Lopez-Galindez, C., Perez-Brena, P., Villanueva, N., Najera, R., VandePol, S., Steinhaver, D., Delolo, N. & Holland, J. (1985). The quasispecies (extremely heterogeneous) nature of viral RNA genome populations biological relevance. *Gene* 40: 1–8.

Donohue, J. & Trueblood, K. N. (1960). Base pairing in DNA. J. Mol. Biol. 2 363–71.

Fauci, A. S. (1988). The human immunodeficiency virus: infectivity and mechanisms of pathogenesis. *Science* 239: 617–622.

Gehrke, C. W. & Kuo, C. T. K. (1985). Analytical methods for major and modified nucleosides in tRNA, mRNA, DNA and physiological fluids: HPLC, GC, MS, NMR, UV and FTIR. *Bull. Mol. Biol. Med.* 10: 119–142.

Gojobori, T. & Yokoyama, S. (1985). Rates of evolution of the retroviral oncogene of Moloney murine sarcoma virus and its cellular homologues. *Proc. Natl. Acad. Sci. US.* 82: 4198–4201.

Granier and Valantin (1998) Presse médicale 27: 622–623.

Hill, F., Loakes, D., Brown, D. M. (1998). Polymerase recognition of synthetic oligodeoxyribonucleotides incorporating degenerate pyrimidine and purine bases. *Biochemistry.* 95: 4258–4263.

Hu, W. S. & Temin, H. M. (1990b). Retroviral recombination and reverse transcription. Science. 250: 1227–1233.

Hunter, W. N., Brown, T., Kneale, G., Anand, N, N., Rabinovich, D. & Kennard, 0. (1997). The structure of guanosine-thymidine mismatches in B-DNA at 2.5 A resolution. *J. Biol. Chem.* 262: 9962–9970.

Japour, A. J., Chatis, P. A., Eigenrauch, H. A &, Crumpacker, C. S. (1991). Detection of human immunodeficiency virus type 1. Clinical isolates with reduced sensitivity to zidovudine and dideoxyinosine by RNA/RNA hybridization. *Proc. Natl., Acad. Sci. USA.* 88: 3092–3096.

Ji, J., Hoffmann, J. S. & Loeb, L. (1994). Mutagenicity and pausing of HIV reverse transcriptase during HIV plus-strand DNA synthesis. *Nucleic Acids Res.* 22: 47–52.

Ji, J. & Loeb, L. A. (1994). Fidelity of HIV-1 reverse transcriptase copying a hypervariable region of the HIV-1 env gene. *Virology* 199: 323–330.

Jolly, D. J., Willis, R. C. & Friedmann, T. (1986). Variable stability of a selectable provirus after retroviral vector gene transfer into human cells. *Mol. Cell. Biol.* 6: 1141–1147.

Kim, S. Y., Byrn, R., Groopman, J. & Baltimore, D. (1989). Temporal aspects of DNA and RNA synthesis during human immunodeficiency virus infection: evidence for differential gene expression. *J. Virol.* 63: 3708–3713.

Kudritskaya, Z. G. & Danilov, V. I. (1976). Quantum mechanical study of base interactions. *J. Theor. Biol.* 59 303–318.

Lecomte, P. J. & Ninio, J. (1987) Variations with position of replication errors up to exonuclease warmup. *FEBS Lett.* 194–198.

Lecomte, P. J. & Ninio, J. (1988). Nucleotide excision by *E. coli* DNA polymerase I in proofreading and nonproofreading modes. *Biochimica Biophysica Acta.* 951: 255–260.

Lefebvre, I., Périgaud, C., Pompon, A., Aubertin, A. M., Girardet, J. L., Kirn, A., Gosselin, G., Imbach, J. L. (1995). Mononucleoside phosphotriester derivatives with S-acyl-2-thioethyl bioreversible phosphate-protecting groups: intracellular delivery of 3'-azido-2',3'-dideoxythymidine 5'-monophosphate. *J. Med. Chem.* 38: 3941–3950.

Limbach, P. A., Crain, P. F., Pomerantz, S. C., McCloskey J. A. (1995). Structures of posttranscriptionally modified nucleosides from RNA. *Biochimie.* 77: 135–138.

Modrow, S., Hahn, B. H., Shaw, G. M., Gallo, R. C., Wong-Staal, F. & Wolf, H. (1987). Computer-assisted analysis of envelope protein sequences of seven human immunodeficiency virus ioslates prediction of antigenic epitopes in conserved and variable regions. *J. Virol.* 61: 570–578.

Morris Jones et al. (1997) Expert. Opin. Invest. Drugs 6(8): 1049–1061.

Motorin Y., & Grosjean H. (1998). Appendix 1: Chemical structures and classification of postranscriptionally modified nucleosides in RNA. *Modification and Editing of RNA.* 543–549.

Papanicolaou, C. & Ripley, L. S. (1989). Polymerase-specific differences in the DNA intermediates of frameshift mutagenesis. In vitro synthesis errors of *Escherichia coli* DNA polymerase I and its large fragment derivative. *J. Mol. Biol.* 207: 335–353.

Papanicolaou, C. & Ripley, L. S. (1991) An in vitro approach to identifying specificity determinants of mutagenesis mediated by DNA misalignments, *J. Mol. Biol.* 221: 805–821.

Pathak, V. K. & Temin, H. M. (1990a). Broad spectrum of in vivo forward mutations, hypermutations and mutational hotspots in a retroviral shuttle vector after a single replication cycle: deletions and deletions with insertions. *Proc. Natl. Acad. Sci. USA.* 87: 6024–6028.

Pathak, V. K. & Temin, H. M. (1990b). Broad spectrum of in vivo forward mutations, hypermutations and mutational hot spots in a retroviral shuttle vector after a single replication cycle: substitutions, frameshifts and hypermutations. *Proc. Natl. Acad. Sci. USA.* 87: 6019–6023.

Patick et al. (1997) Antimicrob. Agents Chemother. 41: 2159–2164.

Perrino, F. W., Preston, B. D., Sandell, L. L. & Loeb, L. A. (1989). Extension of mismatched 3, termini of DNA is a major determinant of the infidelity of Human Immunodeficiency Virus Type 1 Reverse Transcriptase. *Proc. Natl. Acad. Sci. USA.* 86: 8343–8347.

Preston, B. D. & Garvey, N. (1992). *Pharm. Techn.* 16: 34–51.

Saenger, W. (1984). Principles of nucleic acid structure. Springer Verlag N.Y.

Sato, H., Orenstein, L., Dimitrov, D. & Martin, M. (1992). Cell-to-cell spread of HIV-1 occurs within minutes and may not involve the participation of virus particles. *Virology* 18: 712–724.

Tong et al. (1997) Biochemistry 36 (19): 5749–5757.

Wabl, M., Burrows, P. D., Gabian, A. V. & Steinberg, C. (1985). Hypermutation at the immunoglobulin heavy chain locus in a pre-B-cell line. Proc. Natl. Acad. Sci. USA. 82: 479–482.

Yu, H. & Goodman, M. F. (1992). Comparison of HIV-1 and Avian Myeloblastosis Virus reverse transcriptase fidelity on RNA and DNA templates. *J. Biol. Chem.* 267: 10888–10896.

What is claimed is:

1. A method of treating a condition involving reverse transcriptase in a subject, which comprises administering to the subject at least one nucleotide analog that is a substrate of reverse transcription, said nucleotide analog a) has a 3'—H group located on the C3' carbon of the 2'-deoxyribose, said 3'—OH group being capable of exchanging phosphodiester bonds with the chain being formed and the next nucleotide, and b) does not terminate the reverse transcription.

2. The method as claimed in claim 1, wherein the nucleotide analog makes it possible to control the fidelity of the reverse transcription.

3. The method as claimed in claim 2, wherein the nucleotide analog introduces a controlled mutation of the bases.

4. The method as claimed in claim 1, wherein the nucleotide analog makes it possible to control the processivity of the reverse transcriptase.

5. The method as claimed in claim 2, wherein said nucleotide analog:
(a) decreases, in a controlled manner, the fidelity of the reverse transcription, lowers, in a controlled manner, the processivity of the reverse transcriptase, decreases, in a controlled manner, the pause time of the reverse transcriptase, or a combination thereof;
(b) increases, in a controlled manner, the fidelity of the reverse transcription, increases, in a controlled manner, the processivity of the reverse transcriptase, extends, in a controlled manner, the pause time of the reverse transcriptase, or a combination thereof.

6. The method as claimed in claim 1, wherein the condition is caused by a retroid virus.

7. The method as claimed in claim 6, wherein said retroid may infect humans, animals, or plants.

8. The method as claimed in claim 7, wherein the retroid virus is a lentivirus, a RNA oncovirus, a spumavirus, or a hepadnavirus.

9. The method as claimed in claim 8, wherein the lentivirus is a human immunodeficiency virus (HIV) or a human T-cell leukemia virus (HTLV).

10. The method as claimed in claim 8, wherein the hepadnavirus is a hepatitis B virus (HBV).

11. The method as claimed in claim 1, wherein the nucleotide analog introduces a mismatch.

12. The method as claimed in claim 11, wherein the nucleotide analog pairs according to a pairing of the Wobble type.

13. The method as claimed in claim 11, wherein the nucleotide analog pairs according to a pairing of the ANTI-SYN type.

14. The method as claimed in claim 11, wherein the nucleotide analog pairs according to a pairing of the Hoogsteen type, the reverse Hoogsteen type, or both.

15. The method as claimed in claim 11, wherein the nucleotide analog pairs according to a pairing of the reverse Watson-Crick type.

16. The method of claim 1, wherein the nucleotide analog is an all natural modified nucleotide.

17. The method of claim 16, wherein the nucleotide analog is a modified nucleotide of prokaryotic or eukaryotic transfer RNAs (tRNAs).

18. The method of claim 17, wherein the nucleotide analog is dUTP, dITP, C7dGTP, or C7dATP.

19. The method of claim 1, wherein the nucleotide is exogenous to living cells.

20. The method of claim 19, wherein the nucleotide analog comprises a modified base selected from the group consisting of 6H, 8H-3, 4-dihydropyrimido[4,5c][1,2]oxazin-7-one (P), and $N^6$-methoxy-2,6-diaminopurine (K).

21. The method of claim 1, wherein the nucleotide analog is in the triphosphate form or the deoxytriphosphate form.

22. The method of claim 1, wherein the nucleotide analog further comprises a group which protects the functional groups.

23. The method of claim 1, wherein the nucleotide analog is in the form of a bis(S-acyl-2-thioethyl) pronucleotide.

24. A pharmaceutical composition comprising at least one nucleotide analog having a 3'-OH group located on the C3'carbon of the 2'-deoxyribose, said 3'-OH group being capable of exchanging phosphodiester bonds with the chain being formed and the next nucleotide, and does not terminate the reverse transcription reaction and a pharmaceutically acceptable vehicle.

25. The pharmaceutical composition as claimed in claim 24, and further comprising at least one antiretroviral agent selected from the group consisting of nucleotide and non-nucleotide reverse transcriptase inhibitors and viral antiproteases.

26. The pharmaceutical composition as claimed in claim 25, wherein the reverse transcriptase inhibitor is selected from the group consisting of 3'-azido-3'-deoxythymidine (AZT), 2',3'-dideoxyinosine (ddI), 2',3'-dideoxycytidine (ddC), (−)2',3'-dideoxy-3'-thiacytidine (3TC), 2',3'-didehydro-2',3'-dideoxythymidine (d4T) and (−)2'-deoxy-5-fluoro-3'-thiacytidine (FTC), TIBO (tetrahydroimidazo-(4,5, 1-1, jk)(1,4)-benzodiapezin-2(1H)-one), HEPT (1-[(2-hydroxyethoxy)methyl]-6-phenylthiothymine), TSAO ([2', 5'-bis-O-(tert-butyldimethylsilyl)-beta-D-ribofuranosyl]-3'-spiro-5"- (4"-amino-1",2"-oxathiol-2",2"-dioxide), alpha-APA (alpha-anilinophenylacetamide), nevirapine, BAHP (bis(etheroaryl)piperazine), and phosphonoformic acid (PFA).

27. The pharmaceutical composition as claimed in claim 25, wherein the viral antiprotease is indinavir or saquinavir.

28. The method of claim 3, wherein the controlled mutation is a substitution mutation, a deletion mutation, or an insertion mutation.

29. The method of claim 9, wherein the human immunodeficiency virus (HIV) is a human immunodeficiency virus type 1 (HIV-1).

30. The method of claim 16, wherein the all natural modified nucleotide is modified nucleotide of prokaryotic or eukaryotic RNAs.

* * * * *